US012606545B2

(12) United States Patent
Yun et al.

(10) Patent No.: US 12,606,545 B2
(45) Date of Patent: Apr. 21, 2026

(54) COMPOUND FOR ORGANIC ELECTRONIC ELEMENT, ORGANIC ELECTRONIC ELEMENT USING THE SAME, AND AN ELECTRONIC DEVICE THEREOF

(71) Applicant: DUK SAN NEOLUX CO., LTD., Cheonan-si (KR)

(72) Inventors: Jin Ho Yun, Cheonan-si (KR); Mi Young Chae, Cheonan-si (KR); Sun Hee Lee, Cheonan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 979 days.

(21) Appl. No.: 17/272,363

(22) PCT Filed: Jul. 25, 2019

(86) PCT No.: PCT/KR2019/009289

§ 371 (c)(1),
(2) Date: Mar. 1, 2021

(87) PCT Pub. No.: WO2020/045831

PCT Pub. Date: Mar. 5, 2020

(65) Prior Publication Data

US 2022/0123224 A1 Apr. 21, 2022

(30) Foreign Application Priority Data

Aug. 31, 2018 (KR) ........................ 10-2018-0103980

(51) Int. Cl.
*H10K 50/11* (2023.01)
*C07B 59/00* (2006.01)
(Continued)

(52) U.S. Cl.
CPC .......... *C07D 405/14* (2013.01); *C07B 59/002* (2013.01); *C07D 409/14* (2013.01);
(Continued)

(58) Field of Classification Search
CPC ..... H10K 60/11; C07D 405/14; C07D 409/14
See application file for complete search history.

(56) References Cited

U.S. PATENT DOCUMENTS

| | | | | |
|---|---|---|---|---|
| 2005/0236970 | A1* | 10/2005 | Matsudate | H10K 59/122 313/500 |
| 2020/0161563 | A1* | 5/2020 | Jang | C07F 15/0033 |
| 2021/0091314 | A1* | 3/2021 | Shin | H10K 85/654 |

FOREIGN PATENT DOCUMENTS

| | | | | |
|---|---|---|---|---|
| CN | 107619412 | A * | 1/2018 | C09K 11/06 |
| KR | 10-2013-0142967 | A | 12/2013 | |
| KR | 10-2014-0004005 | A | 1/2014 | |
| KR | 10-2014-0074925 | A | 6/2014 | |
| KR | 10-2014-0074936 | A | 6/2014 | |
| KR | 10-2015-0070860 | A | 6/2015 | |
| KR | 10-2017-0113398 | A | 10/2017 | |

(Continued)

OTHER PUBLICATIONS

Korean Office Action mailed Jan. 16, 2023 for KR 10-2018-0103980 A, 13 pages.

*Primary Examiner* — Sean M DeGuire

(74) *Attorney, Agent, or Firm* — Vorys, Sater, Seymour and Pease LLP; Mih Suhn Koh

(57) ABSTRACT

The present invention provides the compound represented by Formula 1, an organic electric element comprising a first electrode, a second electrode, and an organic material layer formed between the first electrode and the second electrode, and an electronic device comprising the organic electric element, and by employing the compound represented by Formula 1 in the organic material layer, the driving voltage of the organic electric element can be lowered, and the luminous efficiency and life time of the electric element can be improved.

9 Claims, 1 Drawing Sheet

(51) Int. Cl.

| | |
|---|---|
| ***C07D 405/14*** | (2006.01) |
| ***C07D 409/14*** | (2006.01) |
| ***C09K 11/06*** | (2006.01) |
| ***H10K 50/17*** | (2023.01) |
| ***H10K 85/60*** | (2023.01) |
| ***H10K 101/10*** | (2023.01) |

(52) U.S. Cl.

CPC ............ *C09K 11/06* (2013.01); *H10K 85/654* (2023.02); *H10K 85/6572* (2023.02); *H10K 85/6574* (2023.02); *H10K 85/6576* (2023.02); *C09K 2211/1018* (2013.01); *H10K 50/11* (2023.02); *H10K 50/17* (2023.02); *H10K 2101/10* (2023.02)

(56) References Cited

FOREIGN PATENT DOCUMENTS

| | | | | | |
|---|---|---|---|---|---|
| KR | 2017134264 | A | * | 12/2017 | ........... C07C 13/567 |
| KR | 10-2018-0008279 | A | | 1/2018 | |
| KR | 10-2018-0061074 | A | | 6/2018 | |
| KR | 10-2019-0010350 | A | | 1/2019 | |
| KR | 10-2019-0020930 | A | | 3/2019 | |
| KR | 10-2019-0030963 | A | | 3/2019 | |
| KR | 10-2020-0018321 | A | | 2/2020 | |
| KR | 10-2020-0018322 | A | | 2/2020 | |

* cited by examiner

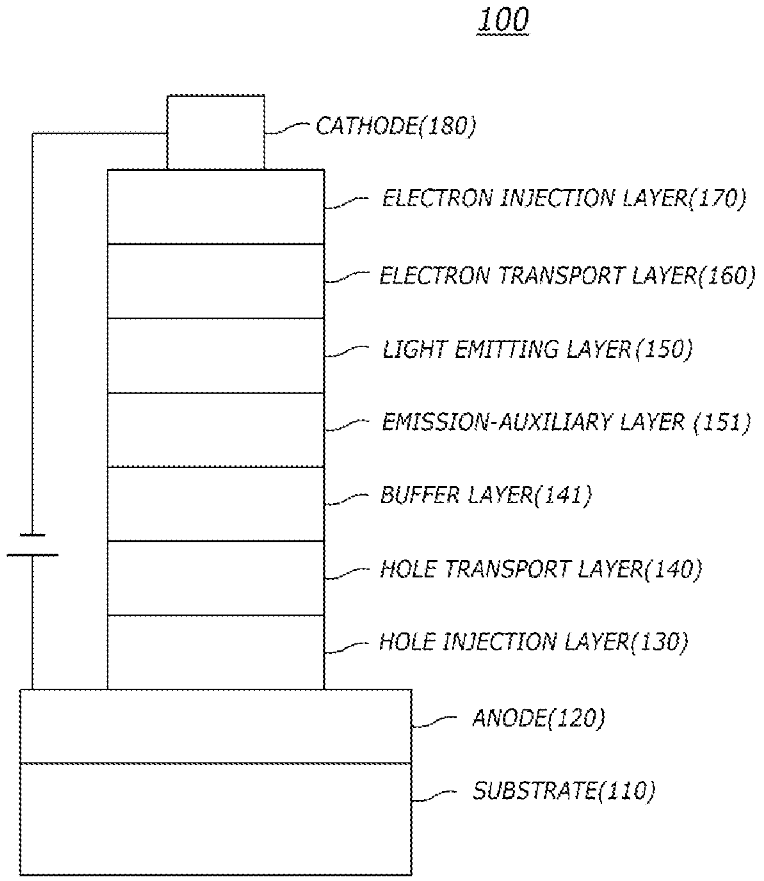
100
CATHODE(180)
ELECTRON INJECTION LAYER(170)
ELECTRON TRANSPORT LAYER(160)
LIGHT EMITTING LAYER(150)
EMISSION-AUXILIARY LAYER (151)
BUFFER LAYER(141)
HOLE TRANSPORT LAYER(140)
HOLE INJECTION LAYER(130)
ANODE(120)
SUBSTRATE(110)

COMPOUND FOR ORGANIC ELECTRONIC ELEMENT, ORGANIC ELECTRONIC ELEMENT USING THE SAME, AND AN ELECTRONIC DEVICE THEREOF

CROSS-REFERENCE TO RELATED APPLICATION

This patent application claims priority from and the benefit under 35 U.S.C. § 119 to § 121, and § 365 of Korean Patent Application No. 10-2018-0103980, filed on Aug. 31, 2018 which is hereby incorporated by reference for all purposes as if fully set forth herein. Further, this application claims the benefit of priority in countries other than U.S., which is hereby incorporated by reference herein.

BACKGROUND

Technical Field

The present invention relates to compound for an organic electric element, an organic electric element using the same and an electronic device thereof.

Background Art

In general, an organic light emitting phenomenon refers to a phenomenon in which electric energy is converted into light energy of an organic material. An organic electric element utilizing the organic light emitting phenomenon usually has a structure including an anode, a cathode, and an organic material layer interposed therebetween. In many cases, the organic material layer has a multi-layered structure having respectively different materials in order to improve efficiency and stability of an organic electric element, and for example, may comprise a hole injection layer, a hole transport layer, a light emitting layer, an electron transport layer, an electron injection layer, or the like.

Materials used as an organic material layer in an organic electric element may be classified into a light emitting material and a charge transport material, for example, a hole injection material, a hole transport material, an electron transport material, an electron injection material, and the like according to its function. Further, the light emitting material may be divided into a high molecular weight type and a low molecular weight type according to its molecular weight, and may also be divided into a fluorescent material derived from excited singlet states of electron and a phosphorescent material derived from excited triplet states of electron according to its light emitting mechanism. Further, the light emitting material may be divided into blue, green, and red light emitting material and yellow and orange light emitting material required for better natural color reproduction according to its light emitting color.

Meanwhile, when only one material is used as a light emitting material, there occur problems of shift of a maximum luminescence wavelength to a longer wavelength due to intermolecular interactions and lowering of the efficiency of a corresponding element due to deterioration in color purity or a reduction in luminous efficiency. On account of this, a host/dopant system may be used as the light emitting material in order to enhance the color purity and increase the luminous efficiency through energy transfer. This is based on the principle that if a small amount of dopant having a smaller energy band gap than a host forming a light emitting layer is mixed in the light emitting layer, then excitons generated in the light emitting layer are transported to the dopant, thus emitting light with high efficiency. With regard to this, since the wavelength of the host is shifted to the wavelength band of the dopant, light having a desired wavelength can be obtained according the type of the dopant.

Currently, the power consumption is required more than more as size of display becomes larger and larger in the portable display market. Therefore, the power consumption is very important factor in the portable display with a limited power source of the battery, and efficiency and life span issues are also solved.

Efficiency, life span, driving voltage, and the like are correlated with each other. If efficiency is increased, then driving voltage is relatively lowered, and the crystallization of an organic material due to Joule heating generated during operation is reduced as driving voltage is lowered. As a result, life span tens to increase. However, efficiency cannot be maximized only by simply improving the organic material layer. This is because long life span and high efficiency can be simultaneously achieved when an optimal combination of energy levels and $T_1$ values, inherent material properties (mobility, interfacial properties, etc.), and the like among the respective layers included in the organic material layer is given.

Therefore, there is a need to develop a light emitting material that has high thermal stability and can efficiently a charge balance in the light-emitting layer. That is, in order to allow an organic electric element to fully exhibit excellent features, it should be prerequisite to support a material constituting an organic material layer in the element, for example, a hole injection material, a hole transport material, a light emitting material, an electron transport material, an electron injection material, or the like, by a stable and efficient material. However, the stable and efficient material of organic material layer for an organic electronic element has not been fully developed yet, in particular, it is strongly required to develop host material of the light emitting layer.

Object, Technical Solution and Effects of the Invention

The present invention is to provide compound lowering a driving voltage, improving luminous efficiency and lifetime of the element, an organic electric element comprising the same, and an electronic device thereof.

In an aspect of the present invention, the present invention provides the compound represented by the following formula.

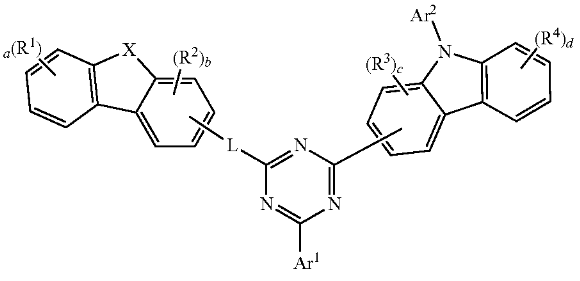

In another aspect of the present invention, the present invention provides an organic electric element using the compound represented by formula above and an electric device thereof.

By using the compound according to embodiment of the present invention, a driving voltage of element can be lowered and the luminous efficiency and lifetime of the element can be significantly improved.

BRIEF DESCRIPTION OF THE DRAWINGS

FIGURE illustrate an example of an organic electroluminescent element according to the present invention: 100 is an organic electric element, 110 is a substrate, 120 is a first electrode, 130 is a hole injection layer, 140 is a hole transport layer, 141 is a buffer layer, 150 is a light emitting layer, 151 is an emission-auxiliary layer, 160 is an electron transport layer, 170 is an electron injection layer, and 180 is a second electrode.

DETAILED DESCRIPTION

Unless otherwise stated, the term "aryl group" or "arylene group" as used herein has, but not limited to, 6 to 60 carbon atoms. The aryl group or arylene group in the present invention may comprise a monocyclic ring, ring assemblies, a fused polycyclic system, spiro-compounds and the like.

The term "heterocyclic group" used in the specification comprises a non-aromatic ring as well as an aromatic ring like "heteroaryl group" or "heteroarylene group". Unless otherwise stated, the term "heterocyclic group" means, but not limited to, a ring containing one or more heteroatoms and having 2 to 60 carbon atoms. Unless otherwise stated, the term "heteroatom" as used herein represents N, O, S, P or Si and the heterocyclic group means a monocyclic, ring assemblies, fused polycyclic system or spiro compound containing a heteroatom.

The term "heterocyclic group" used in the specification means a ring containing heteroatom such as N, O, S, P, Si and so on, it comprises a non-aromatic ring as well as an aromatic ring like "heteroaryl group" or "heteroarylene group". In addition, heterocyclic group comprises the compound comprising the heteroatom group such as $SO_2$, P═O etc. instead of carbon forming a ring like the following compound.

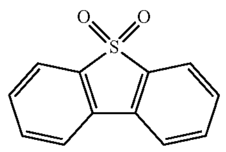 [SMILES: O=S1(=O)c2ccccc2-c2ccccc21]

Unless otherwise stated, the term "fluorenyl group" or "fluorenylene group" as used herein means univalent or bivalent functional group of fluorene in which R, R' and R" are all hydrogen in the following structure, "substituted fluorenyl group", "substituted fluorenylene group" or "substituted fluorenylenetriyl group" means that at least any one of R, R' and R" is a substituent other than hydrogen. The term "fluorenyl group" or "fluorenylene group" comprises the case where R and R' are bonded to each other to form the spiro compound together with the carbon bonded to them.

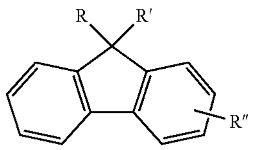

The term "spiro compound" as used herein has a spiro union which means union having one atom as the only common member of two rings. The common atom is designated as 'spiro atom'. The compounds are defined as 'monospiro-', 'dispiro-' or 'trispiro-' depending on the number of spiro atoms contained in compound.

In this specification, a 'group name' corresponding to an aryl group, an arylene group, a heterocyclic group, and the like exemplified for each symbol and its substituent may be written in the name of functional group reflecting the valence, and may also be described as the name of a parent compound. For example, in the case of phenanthrene which is a kind of aryl group, it may be described by distinguishing valence such as 'phenanthryl (group)' when it is 'monovalent group', and 'phenanthrylene (group)' when it is 'divalent group', and regardless of its valence, it may also be described as 'phenanthrene' which is a parent compound name. Similarly, in the case of pyrimidine, it may be described as 'pyrimidine' regardless of its valence, and it may also be described as the name of corresponding functional group such as pyrimidinyl (group) when it is 'monovalent group', and 'pyrimidinylene (group)' when it is 'divalent group'.

In addition, unless otherwise expressed, where any formula of the present invention is represented by the following formula, the substituent according to the index may be defined as follows.

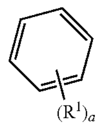

Here, the substituent $R^1$ is absent when a is an integer of zero, the sole $R^1$ is bonded to any one of the carbon atoms constituting the benzene ring when a is an integer of 1, when a is an integer of 2 or 3, the substituent $R^1$s may be bonded as follows and the substituents $R^1$s may be the same or different each other, and the substituent $R^1$s may be bonded to the carbon of the benzene ring in a similar manner when a is an integer of 4 to 6. Herein, the indication of the hydrogen bonded to the carbon which forms the benzene ring is omitted.

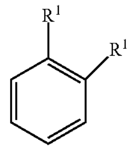

(a = 2)

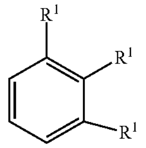

(a = 3)

Hereinafter, a laminated structure of the electric element comprising the compound of the present invention will be described with reference to FIGURE.

In the following description of the present invention, a detailed description of known configurations and functions incorporated herein will be omitted when it may make the subject matter of the present invention rather unclear.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

FIGURE illustrates an example of an organic electric element according to an embodiment of the present invention.

Referring to the FIGURE, an organic electric element 100 according to an embodiment of the present invention includes a first electrode 120 formed on a substrate 110, a second electrode 180, and an organic material layer formed between the first electrode 120 and the second electrode 180 and comprising the compound of the present invention. Here, the first electrode 120 may be an anode (positive electrode), and the second electrode 180 may be a cathode (negative electrode). In the case of an inverted organic electroluminescent element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, or a hole blocking layer, an electron blocking layer, an emission-auxiliary layer 151, an electron transport-auxiliary layer, a buffer layer 141, etc. may be further included in the organic material layer, and the electron transport layer 160 or the like may serve as a hole blocking layer.

In addition, although not shown, the organic electric element according to an embodiment of the present invention may further include a protective layer or a layer for improving luminous efficiency. The layer for improving luminous efficiency may be formed on one side of sides of the first electrode or one side of sides of the second electrode, wherein the one side is not facing the organic material layer.

The inventive compound employed in the organic material layer may be used as a material of a hole injection layer 130, a hole transport layer 140, an emission-auxiliary layer 151, an electron transport-auxiliary layer, an electron transport layer 160 or an electron injection layer 170, as host or dopant of a light emitting layer 150, or as a material of a layer for improving luminous efficiency. Preferably, compound according to Formula 1 of the present invention can be used as host of a light emitting layer.

On the other hand, even if the core is same or similar, the band gap, the electrical characteristics, the interface characteristics and the like may be different depending on which substituent is bonded at which position. Therefore, there is a need to study the selection of the core and the combination of the core and the sub-substituent bonded to the core. In particular, long life span and high efficiency can be simultaneously achieved when the optimal combination of energy levels and $T_1$ values, inherent material properties (mobility, interfacial properties, etc.) and the like among the respective layers of an organic material layer is achieved.

Therefore, the energy level and $T_1$ value between the respective layers of the organic material layer, inherent material properties (mobility, interfacial properties, etc.) and the like can be optimized by using compound represented by Formula 1 as host of a light emitting layer in the present invention.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or alloy on the substrate to form the anode 120, forming the organic material layer including the hole injection layer 130, the hole transport layer 140, the light emitting layer 150, the electron transport layer 160, and the electron injection layer 170 thereon, and then depositing a material which can be used as the cathode 180, thereon. In addition, an emitting auxiliary layer 151 may be formed between a hole transport layer 140 and a light emitting layer 150, and an electron transport-auxiliary layer may be formed between a light emitting layer 150 and an electron transport layer 160.

In addition, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

In addition, the organic electric element according to the present invention may be selected from group consisting of an organic electroluminescent element, an organic solar cell, an organic photo conductor, an organic transistor, an element for monochromatic or white illumination and an element quantum dot display.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electric dictionary, a point-to-multipoint (PMP), a remote controller, a navigation unit, a game player, various kinds of TVs, various kinds of computers and so on.

Hereinafter, the compound according to an aspect of the present invention will be described.

Compound according to one aspect of the present invention may be represented by Formula 1.

<Formula 1>

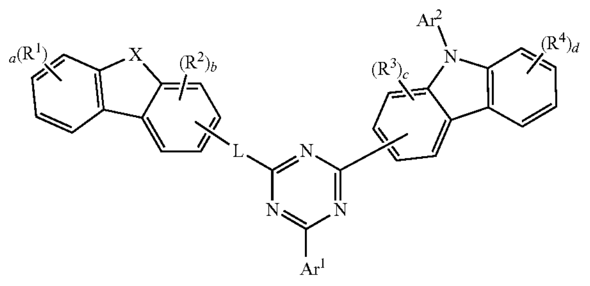

In formula 1, each of symbols may be defined as follows.

X is O, S or N($Ar^3$). Here, $Ar^3$ is selected from the group consisting of a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group and a $C_1$-$C_{50}$ alkyl group.

Where $Ar^3$ is an aryl group, the aryl group may be preferably a $C_6$-$C_{30}$ aryl group, more preferably a $C_6$-$C_{18}$ aryl group, for example, phenyl, naphthyl, biphenyl, terphenyl and the like. Where $Ar^3$ is an alkyl group, the alkyl group may be preferably a $C_1$-$C_{20}$ alkyl group, more preferably a $C_1$-$C_{10}$ alkyl group, for example, methyl, t-butyl and the like.

$R^1$ to $R^4$ are each independently selected from the group consisting of hydrogen, deuterium, halogen, a cyano group, a nitro group, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group, a $C_1$-$C_{50}$ alkyl group, a $C_2$-$C_{20}$ alkenyl group, a $C_2$-$C_{20}$ alkynyl group, a $C_1$-$C_{30}$ alkoxy group, a $C_6$-$C_{30}$ aryloxy group and -L'-N($R_a$)($R_b$), and where X is O or S, adjacent $R^1$ groups or adjacent $R^2$ groups together may be bonded to each other to form a ring. Here, the ring is selected from the group consisting of a $C_6$-$C_{60}$ aromatic ring, a $C_2$-$C_{60}$ heterocyclic group containing at least one heteroatom of O, N, S, Si, and P, a $C_3$-$C_{60}$ aliphatic ring group and a combination thereof.

a and d are each an integer of 0 to 4, b and c are each an integer of 0 to 3, where they are each an integer of 2 or more, each of a plurality of $R^1$s, each of a plurality of $R^2$s, each of a plurality of $R^3$s, each of a plurality of $R^4$s is the same or different from each other.

The case where adjacent $R^3$ groups together are bonded to each other to form a ring, the case where adjacent $R^4$ groups together are bonded to each other to form a ring, and the case where $R^3$ and $Ar^2$ together, or $R^4$ and $Ar^2$ together are bonded to each other to form a ring are excluded. For example, benzocarbazole which is formed as a result of the bonding of adjacent $R^3$ groups to each other to form a benzene ring, and compound being formed as a result of the bonding $R^2$ and $R^4$ to each other to form a ring are excluded. This is because the characteristics of the device are better when compound of the present invention is used as a host than when the ring-formed compound is used, as in the description of Examples and Comparative Examples to be described later, Where $R^1$ to $R^4$ are independently an aryl group, the aryl group may be preferably a $C_6$-$C_{30}$ aryl group, more preferably a $C_6$-$C_{18}$ aryl group, for example, phenyl, naphthyl, biphenyl, terphenyl and the like. Where $R^1$ to $R^4$ are independently a heterocyclic group, the heterocyclic group may be preferably a $C_2$-$C_{30}$ heterocyclic group, more preferably a $C_2$-$C_{18}$ heterocyclic group, for example, dibenzothiophene, dibenzofuran, carbazole, phenylcarbazole and the like. Where $R^1$ to $R^4$ are independently an alkyl group, the alkyl group may be preferably a $C_1$-$C_{20}$ alkyl group, more preferably a $C_1$-$C_{10}$ alkyl group, for example, methyl, t-butyl and the like.

Where adjacent $R^1$ groups or adjacent $R^2$ groups together may be bonded to each other to form an aromatic ring, the aromatic ring may be a $C_6$-$C_{30}$ aromatic ring, more preferably a $C_6$-$C_{14}$ aromatic ring, for example, a ring such as benzene, naphthalene or phenanthrene.

Preferably, at least one of $R^1$ to $R^4$ may be a $C_6$-$C_{60}$ aryl group or a $C_2$-$C_{60}$ heterocyclic group, more preferably, $R^1$ may be a $C_6$-$C_{60}$ aryl group or a $C_2$-$C_{60}$ heterocyclic group, more preferably, $R^1$ may be a $C_6$-$C_{60}$ aryl group.

$Ar^1$ is a $C_6$-$C_{12}$ aryl group. For example, $Ar^1$ is phenyl, naphthalene, biphenyl and the like.

$Ar^2$ is selected from the group consisting of a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group and a $C_1$-$C_{50}$ alkyl group.

Where $Ar^2$ is an aryl group, the aryl group may be preferably a $C_6$-$C_{30}$ aryl group, more preferably a $C_6$-$C_{18}$ aryl group, for example, phenyl, naphthyl, biphenyl, terphenyl and the like.

L is selected from the group consisting of a $C_6$-$C_{60}$ arylene group, a fluorenylene group, a $C_2$-$C_{60}$ heterocyclic group containing at least one heteroatom of O, N, S, Si, and P, a $C_3$-$C_{60}$ aliphatic ring group and a combination thereof.

Where L is an arylene group, the arylene group may be preferably a $C_6$-$C_{30}$ arylene group, more preferably a $C_6$-$C_{18}$ arylene group, for example, phenyl, biphenyl, naphthyl, phenyl substituted with naphthyl, terphenyl and the like. Where L is a heterocyclic group, the heterocyclic group may be preferably a $C_2$-$C_{30}$ heterocyclic group, more preferably a $C_2$-$C_{22}$ heterocyclic group, for example, dibenzothiophene, dibenzofuran, carbazole, phenylcarbazole, benzocarbazole, phenyl substituted benzocarbazole and the like. Where L is a fluorenylene group, the fluorenylene group may be 9,9-dimethylfluorene, 9,9-diphenylfluorene, 9,9'-spirobifluorene and the like.

L' is selected from the group consisting of a single bond, a $C_6$-$C_{60}$ arylene group, a fluorenylene group, a $C_3$-$C_{60}$ aliphatic ring, a $C_2$-$C_{60}$ heterocyclic group containing at least one heteroatom of O, N, S, Si, and P and a combination thereof.

$R_a$ and $R_b$ are each independently selected from the group consisting of a $C_6$-$C_{60}$ aryl group, a fluorenyl group, a $C_3$-$C_{60}$ aliphatic ring group, a $C_2$-$C_{60}$ heterocyclic group containing at least one heteroatom of O, N, S, Si, and P and a combination thereof.

$R^1$ to $R^4$, $Ar^1$ to $Ar^3$, L, L', $R_a$, $R_b$, and the ring formed by bonding adjacent groups to each other may be each optionally substituted with one or more substituents selected from the group consisting of deuterium, halogen, a silane group unsubstituted or substituted with a $C_1$-$C_{20}$ alkyl group or a $C_6$-$C_{20}$ aryl group, a siloxane group, a boron group, a germanium group, a cyano group, a nitro group, a $C_1$-$C_{20}$ alkylthio group, a $C_1$-$C_{20}$ alkoxy group, a $C_6$-$C_{20}$ arylalkoxy group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom of O, N, S, Si, and P, a $C_3$-$C_{20}$ aliphatic ring, a $C_7$-$C_{20}$ arylalkyl group, $C_8$-$C_{20}$ arylalkenyl group and a combination thereof.

Formula 1 may be represented by one of Formula 2 to Formula 5.

<Formula 2>

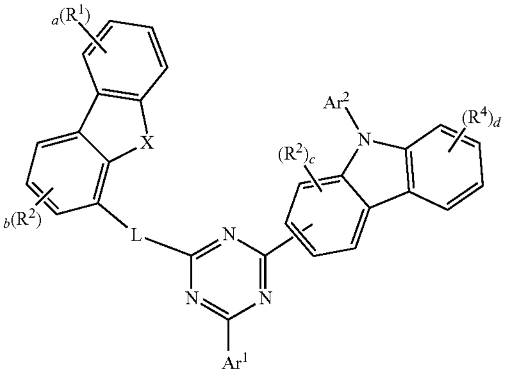

<Formula 3>

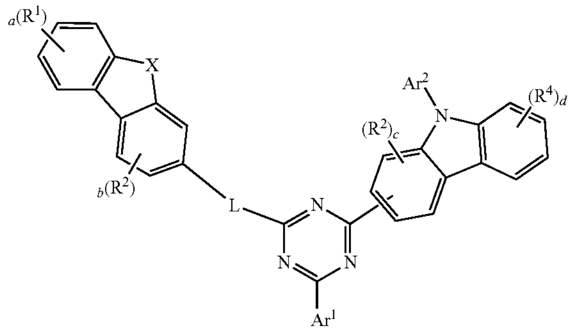

<Formula 4>

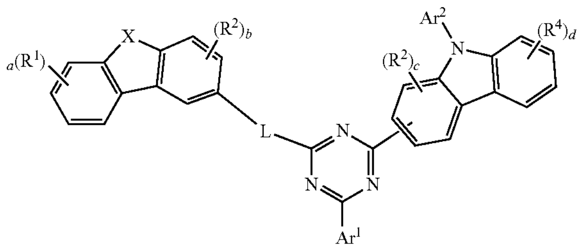

<Formula 5>

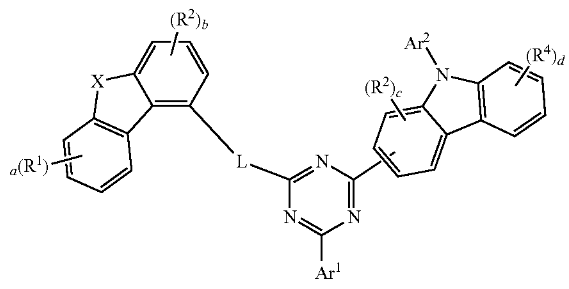

In Formulas 2 to 5, X, $R^1$ to $R^4$, a to d, $Ar^1$, $Ar^2$ and L are the same as defined in Formula 1.

In addition, Formula 1 may be represented by one of Formula 6 to Formula 9.

<Formula 6>

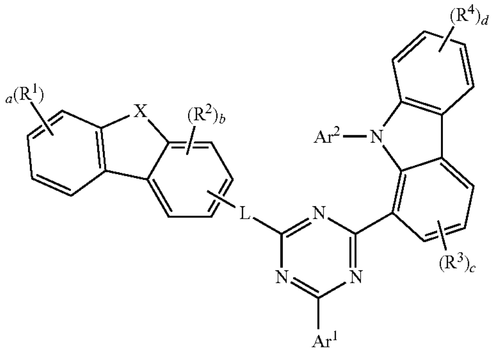

<Formula 7>

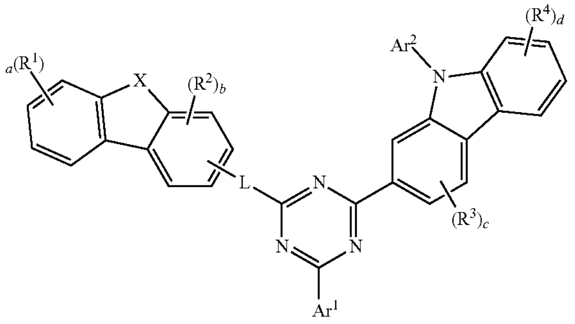

<Formula 8>

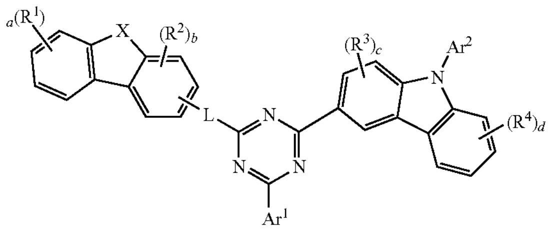

<Formula 9>

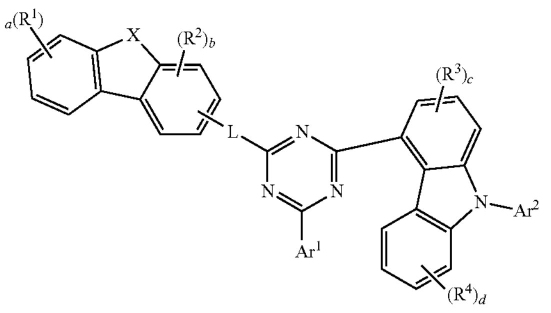

In Formulas 6 to 9, X, $R^1$ to $R^4$, a to d, $Ar^1$, $Ar^2$ and L are the same as defined in Formula 1.

Preferably, L may be selected from the group consisting of Formula a1 to Formula a37.

<Formula a1>
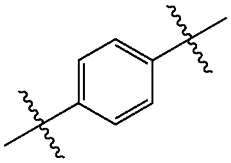
<Formula a2>
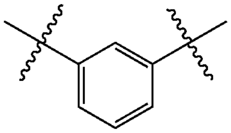
<Formula a3>
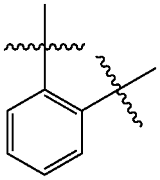
<Formula a4>
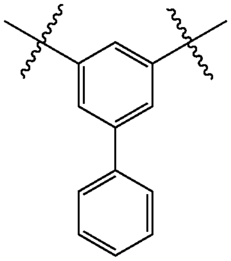
<Formula a5>
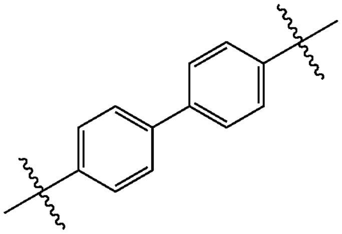
<Formula a6>
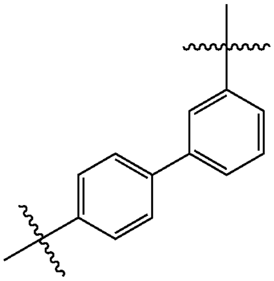
<Formula a7>
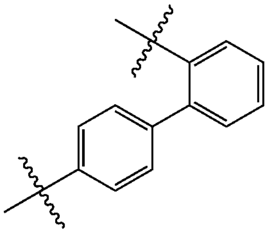
-continued
<Formula a8>
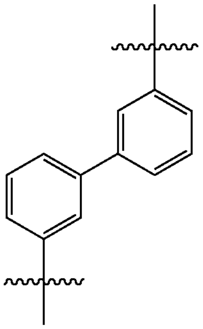
<Formula a9>
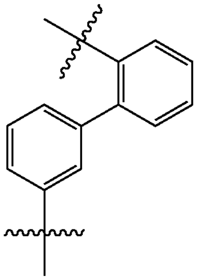
<Formula a10>
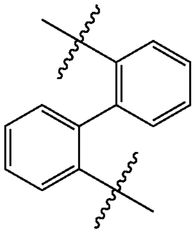
<Formula a11>
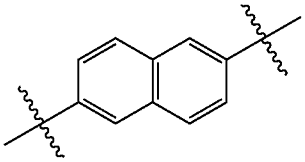
<Formula a12>
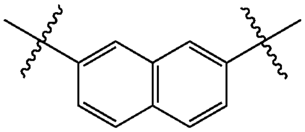
<Formula a13>
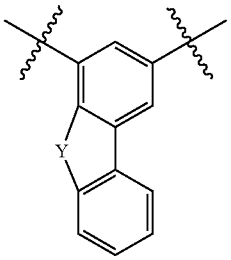

-continued
<Formula a14>
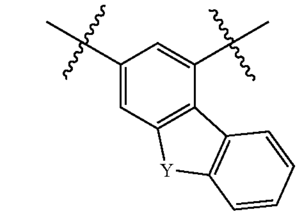
<Formula a15>
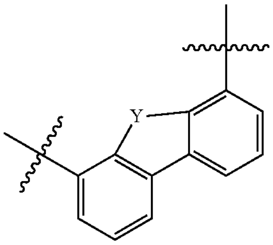
<Formula a16>
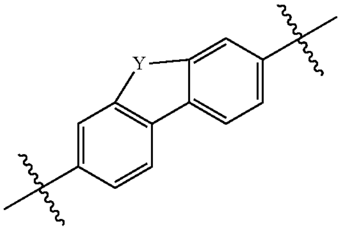
<Formula a17>
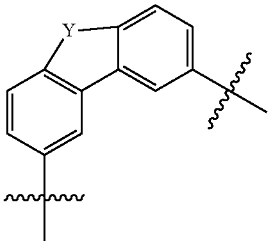
<Formula a18>
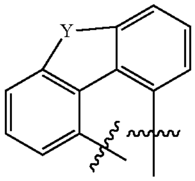
<Formula a19>
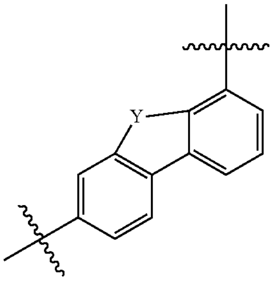
-continued
<Formula a20>
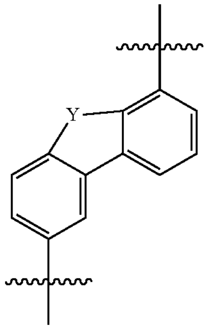
<Formula a21>
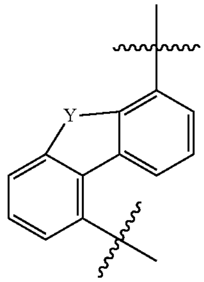
<Formula a22>
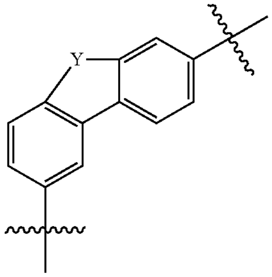
<Formula a23>
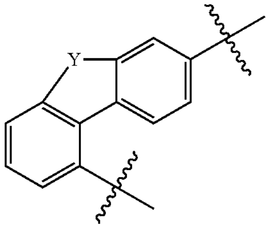
<Formula a24>
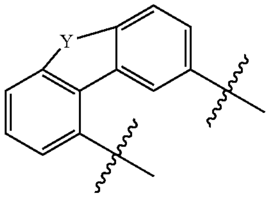
<Formula a25>
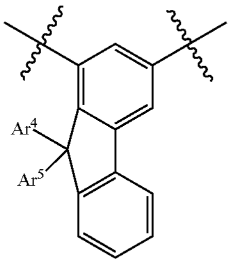

-continued
<Formula a26>
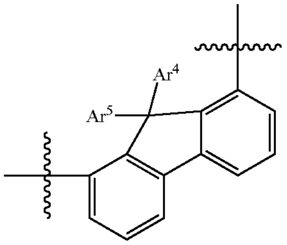
<Formula a27>
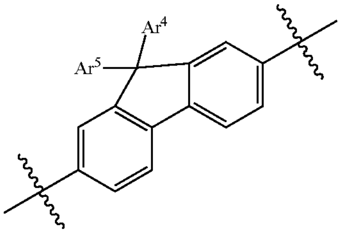
<Formula a28>
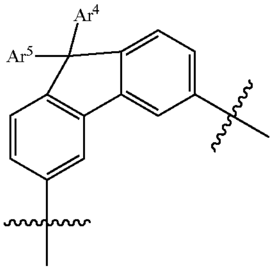
<Formula a29>
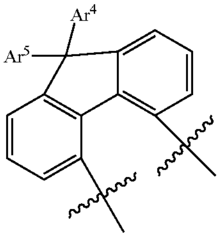
<Formula a30>
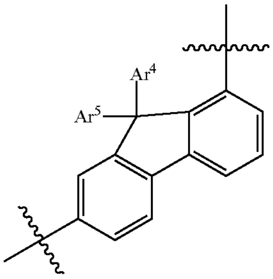
<Formula a31>
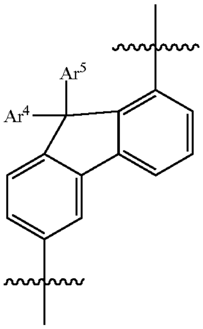
-continued
<Formula a32>
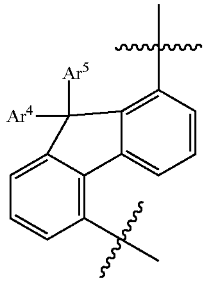
<Formula a33>
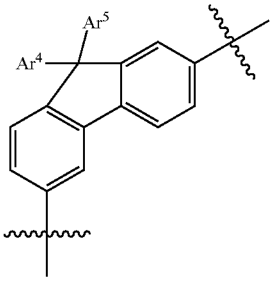
<Formula a34>
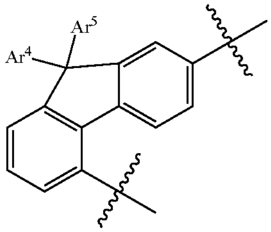
<Formula a35>
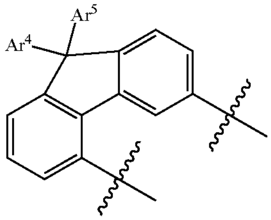
<Formula a36>
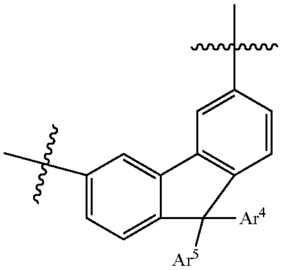
<Formula a37>
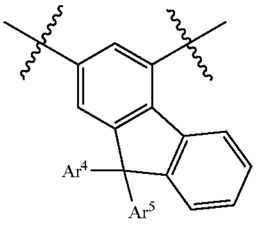
In the above Formulas, Y is O, S or N($Ar^6$), wherein $Ar^6$ is selected from the group consisting of a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group and a $C_1$-$C_{50}$ alkyl group. Preferably, $Ar^6$ is selected from the group consisting of a $C_6$-$C_{20}$ aryl group, a fluorenyl group, a $C_2$-$C_{20}$ heterocyclic group containing at least one heteroatom of O, N, S, Si, and P, a $C_3$-$C_{20}$ aliphatic ring group and a $C_1$-$C_{20}$ alkyl group.

Where $Ar^6$ is an aryl group, the aryl group may be preferably a $C_6$-$C_{20}$ aryl group, more preferably a $C_6$-$C_{18}$ aryl group, for example, phenyl, naphthyl, biphenyl, terphenyl and the like.

$Ar^4$ and $Ar^5$ may be each independently selected from the group consisting of hydrogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group, a $C_1$-$C_{50}$ alkyl group and a combination thereof, and $Ar^4$ and $Ar^5$ together may be bonded to each other to form a ring. Where $Ar^4$ and $Ar^5$ together are bonded to each other to form a ring, a compound such as spirobifluorene may be formed. Preferably, $Ar^4$ and $Ar^5$ may be each independently selected from the group consisting of hydrogen, a $C_6$-$C_{20}$ aryl group, a fluorenyl group, a $C_2$-$C_{20}$ heterocyclic group containing at least one heteroatom of O, N, S, Si, and P, a $C_3$-$C_{20}$ aliphatic ring group and a $C_1$-$C_{20}$ alkyl group.

Where $Ar^4$ and $Ar^5$ are independently an aryl group, the aryl group may be preferably a $C_6$-$C_{30}$ aryl group, more preferably a $C_6$-$C_{18}$ aryl group, for example, phenyl, naphthyl, biphenyl, terphenyl and the like. Where $Ar^4$ and $Ar^5$ are independently an alkyl group, the alkyl group may be preferably a $C_1$-$C_{20}$ alkyl group, more preferably a $C_1$-$C_{10}$ alkyl group, for example, methyl, ethyl, t-butyl and the like.

Specifically, compound represented by formula 1 may be one of the following compounds, but there is no limitation thereto.

P 1-1

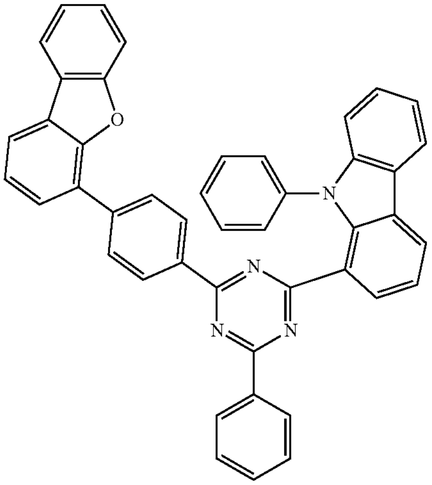

-continued

P 1-2

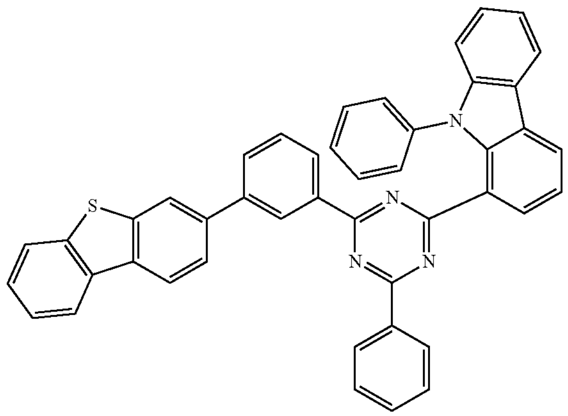

P 1-3

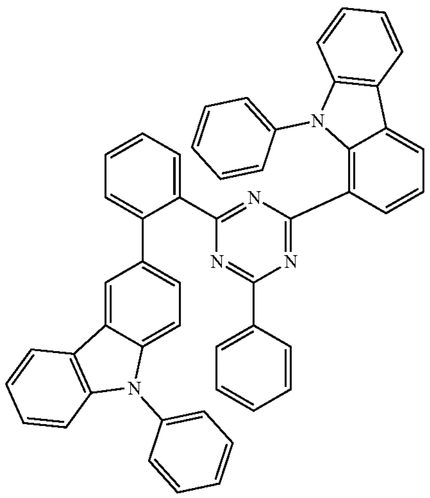

P 1-4

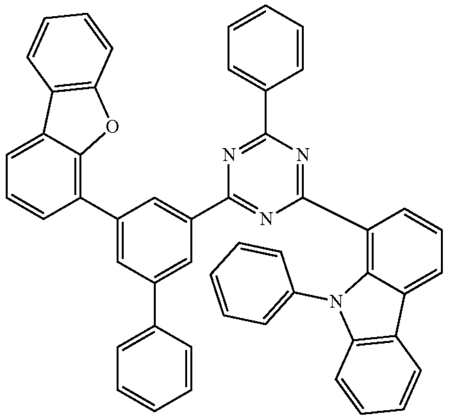

-continued
P 1-5
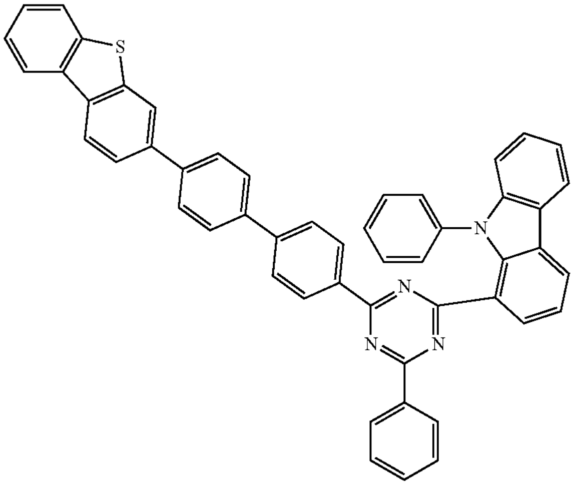
P 1-6
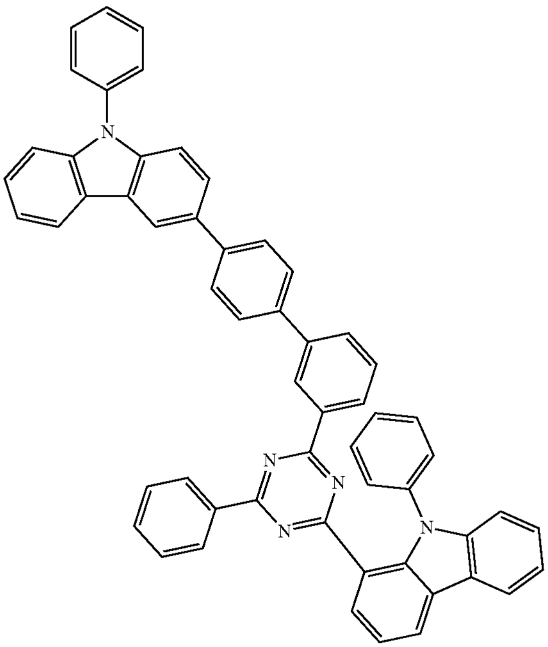
P 1-7
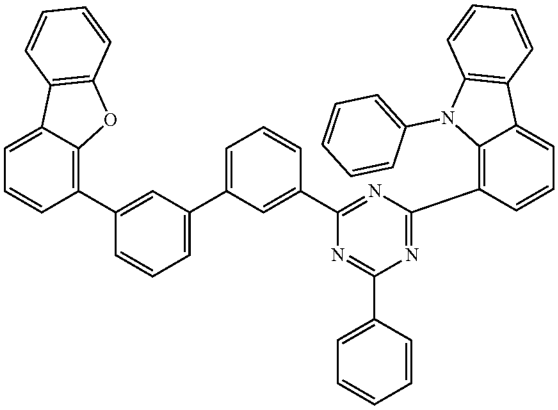
-continued
P 1-8
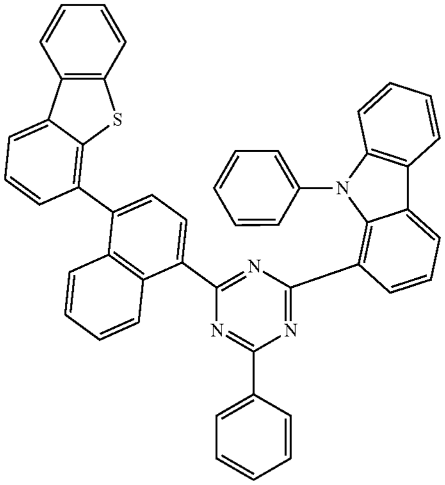
P 1-9
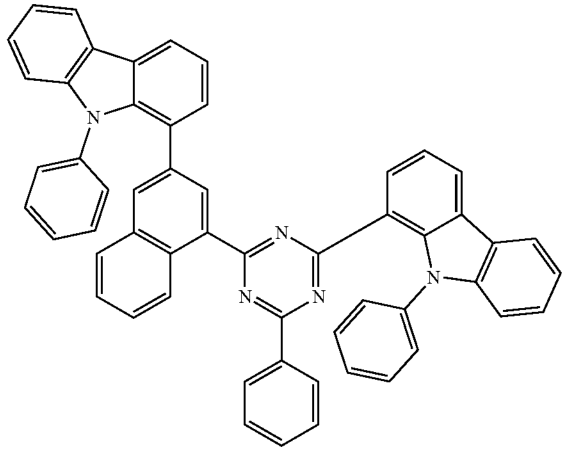
P 1-10
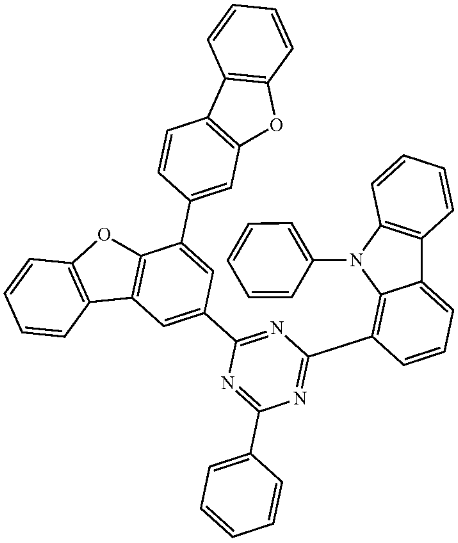

-continued
P 1-11
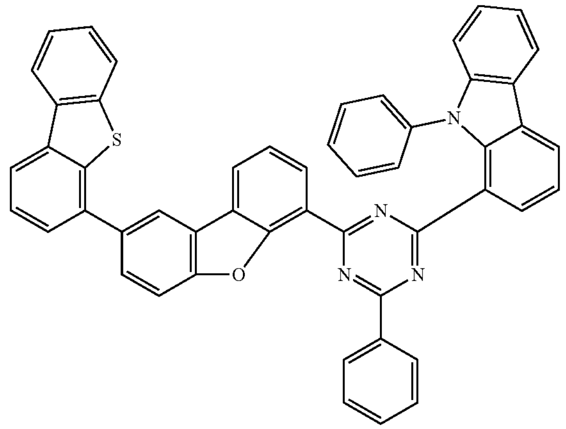
P 1-12
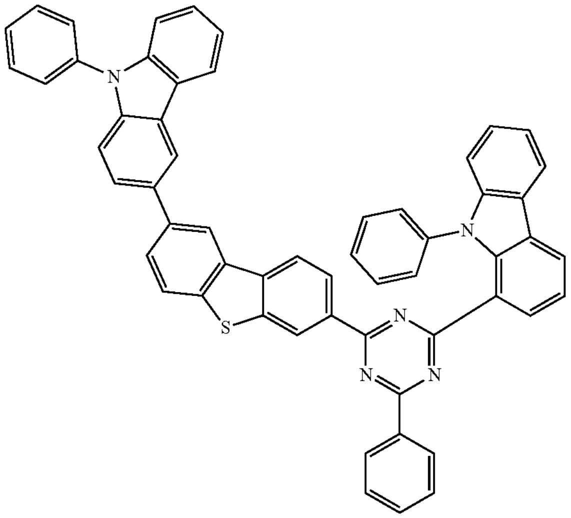
P 1-13
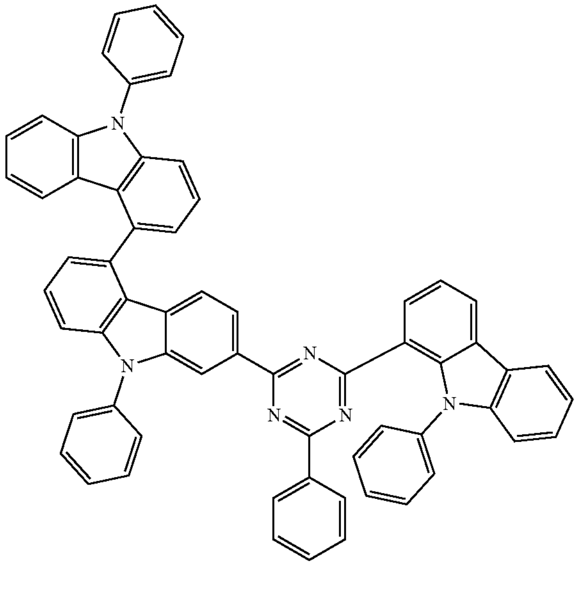
-continued
P 1-14
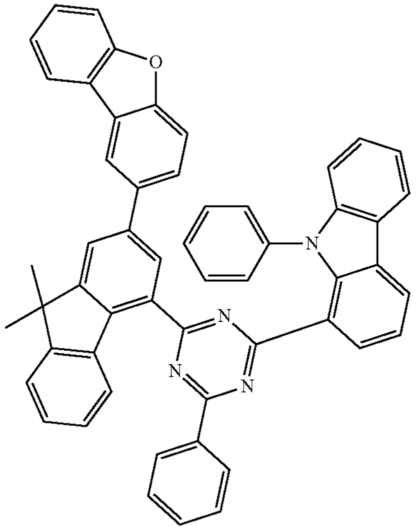
P 1-15
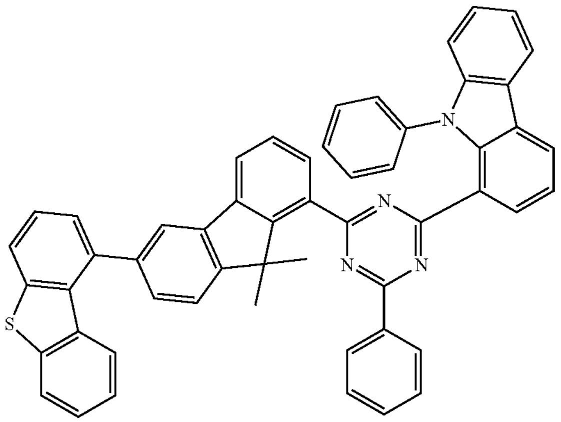
P 1-16
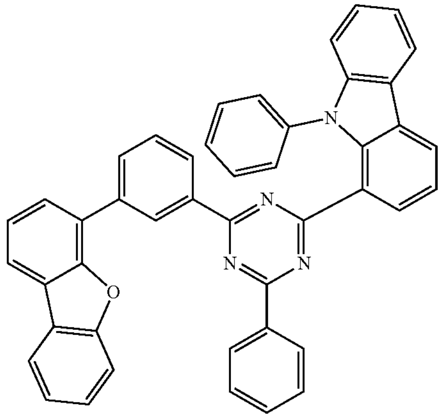

-continued
P 1-17
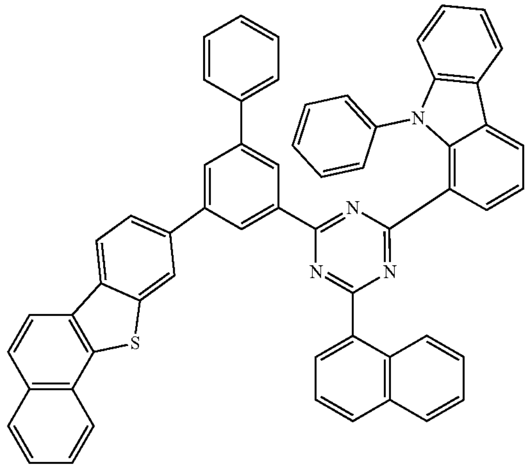
P 1-18
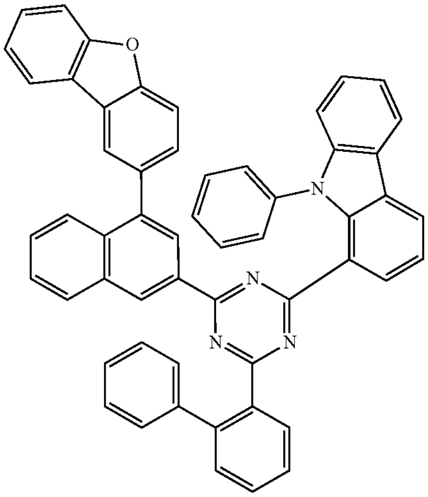
P 1-19
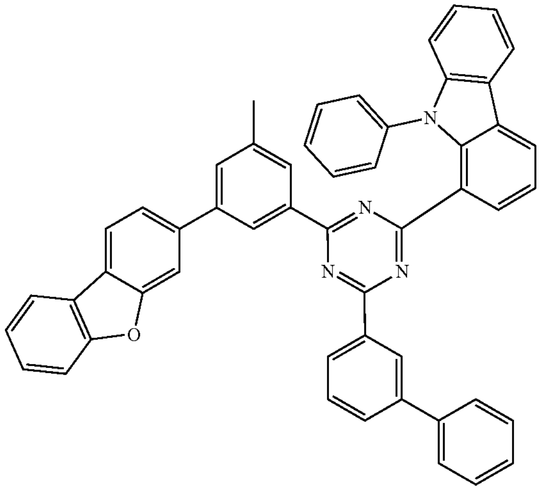
-continued
P 1-20
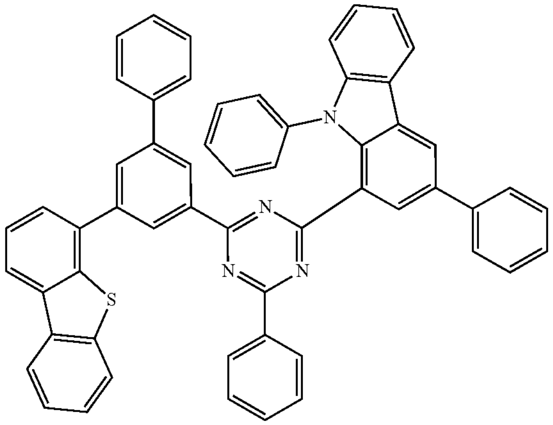
P 1-21
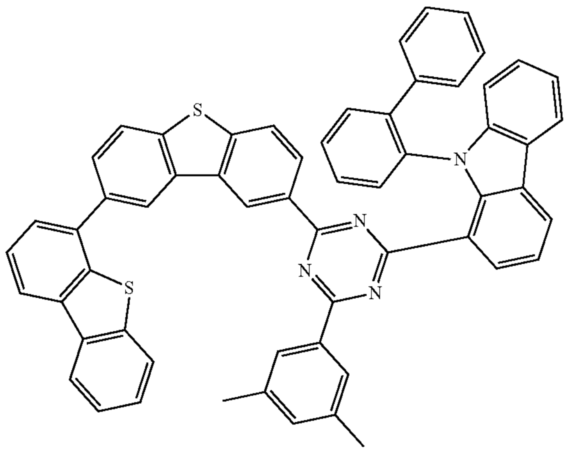
P 1-22
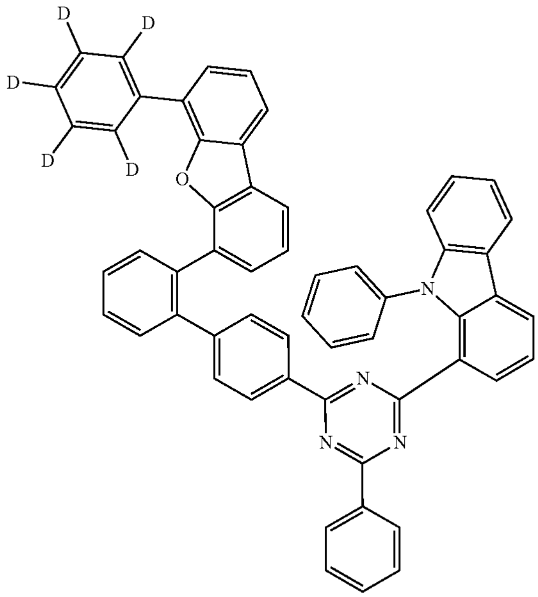

-continued
P 1-23
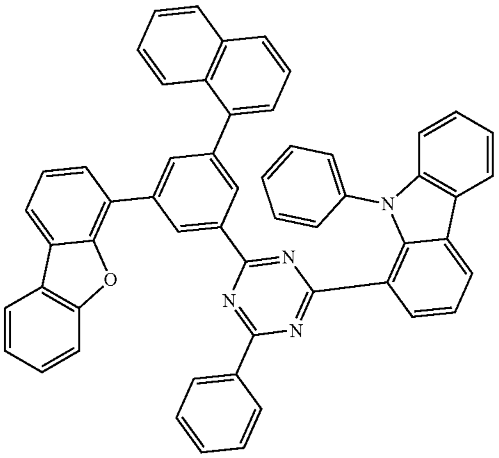
P 1-24
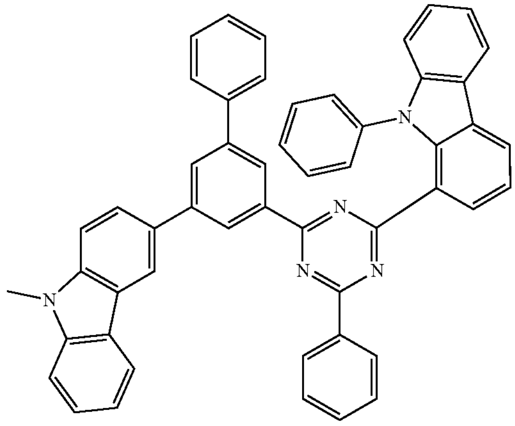
P 1-25
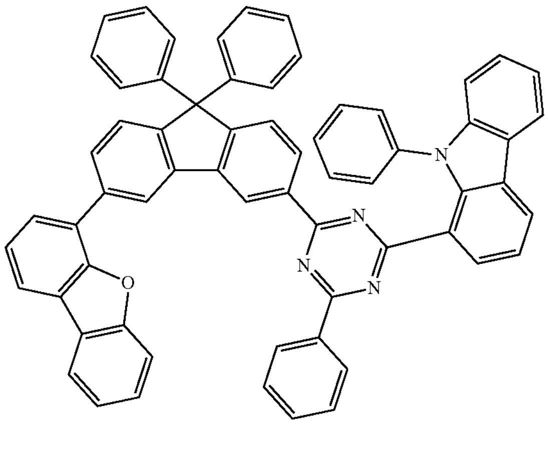
-continued
P 1-26
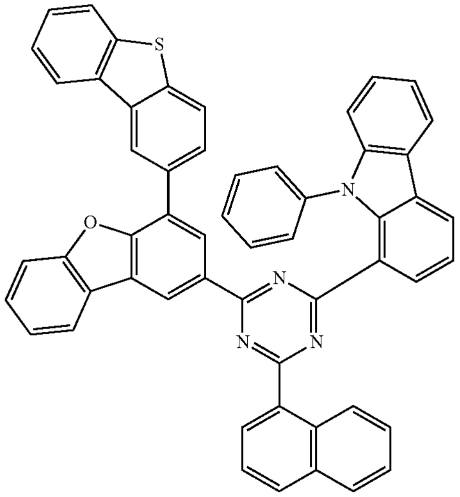
P 1-27
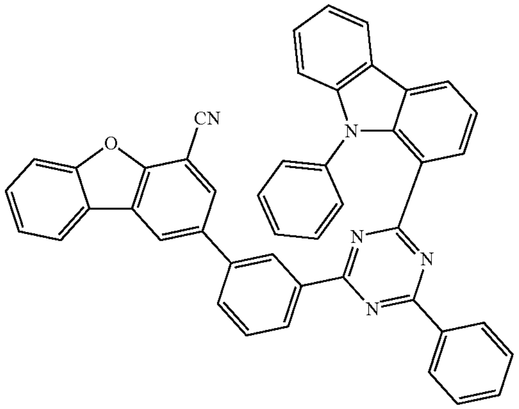
P 1-28
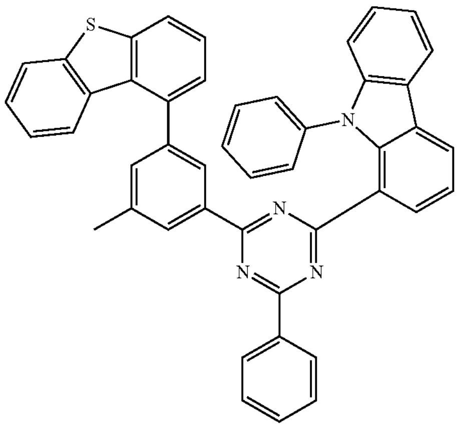

-continued
P 1-29
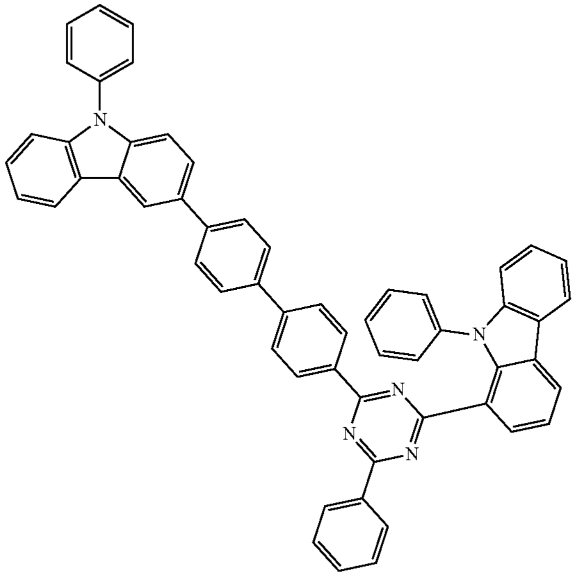
P 1-30
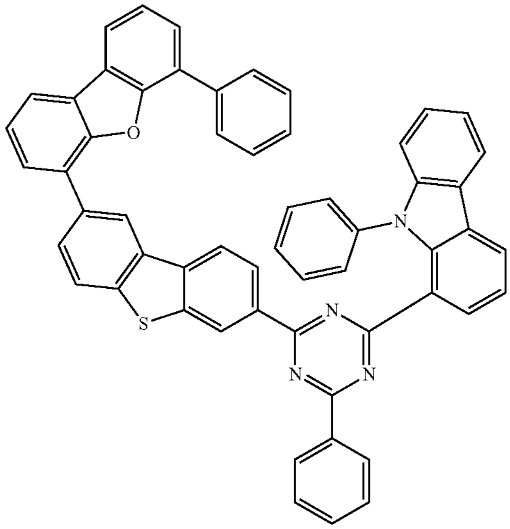
P 2-1
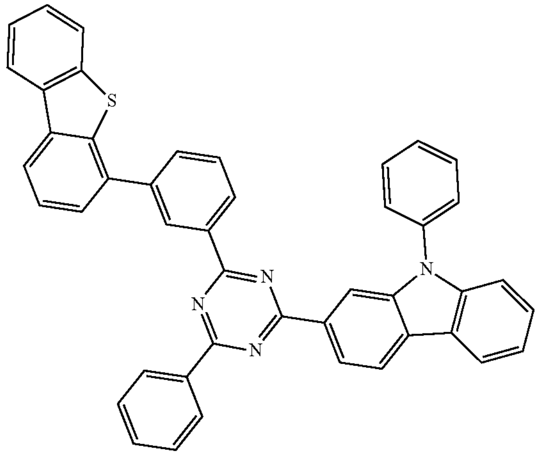
-continued
P 2-2
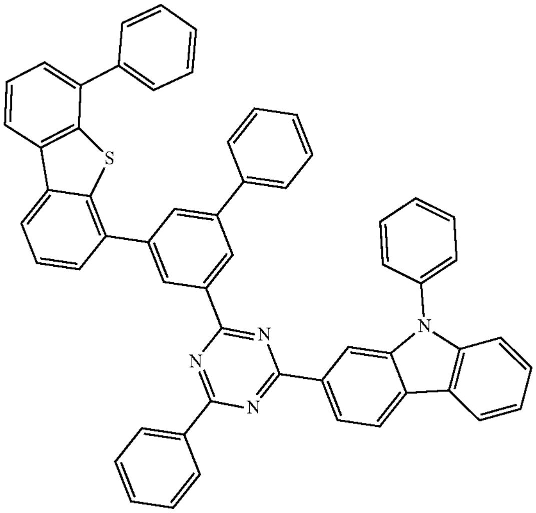
P 2-3
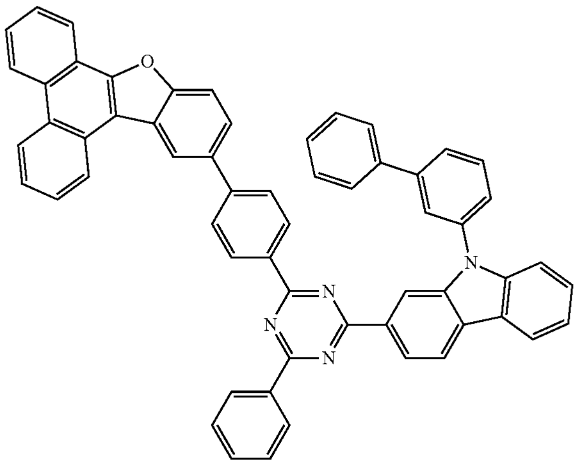
P 2-4
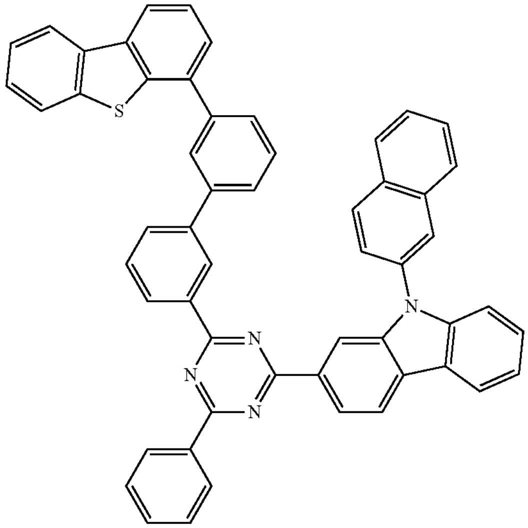

-continued
P 2-5
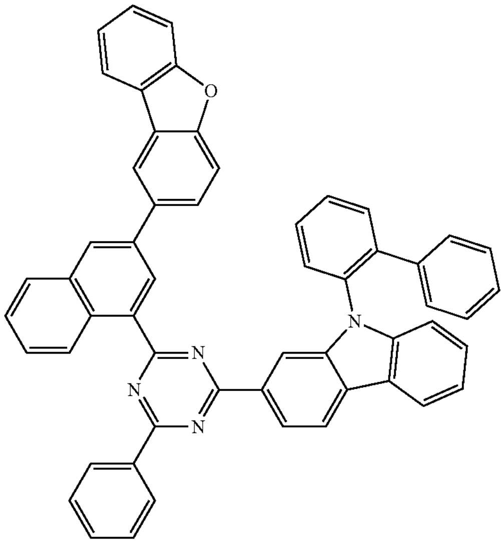
P 2-6
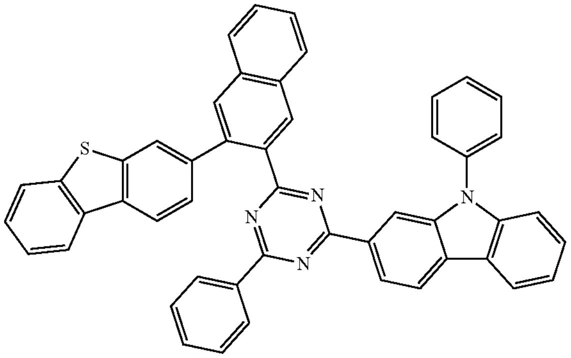
P 2-7
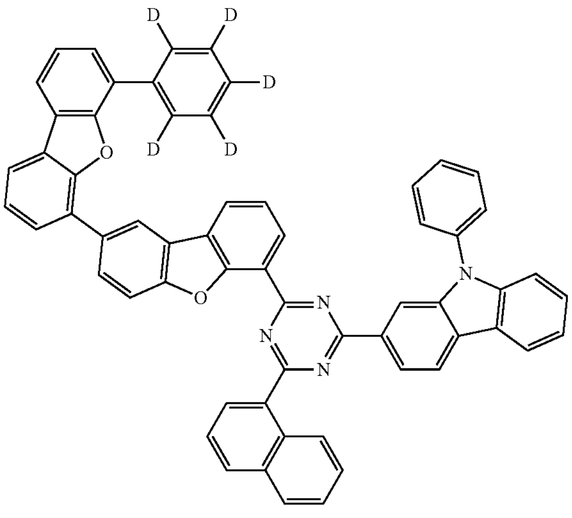
-continued
P 2-8
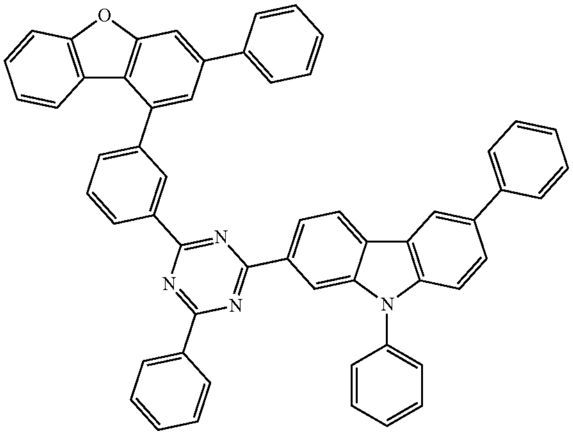
P 2-9
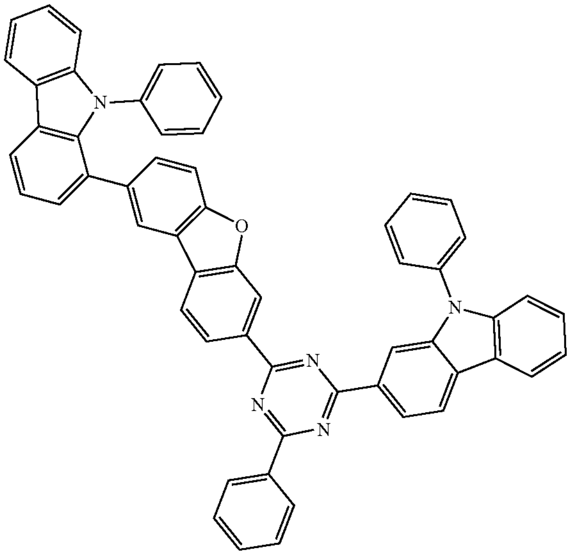
P 2-10
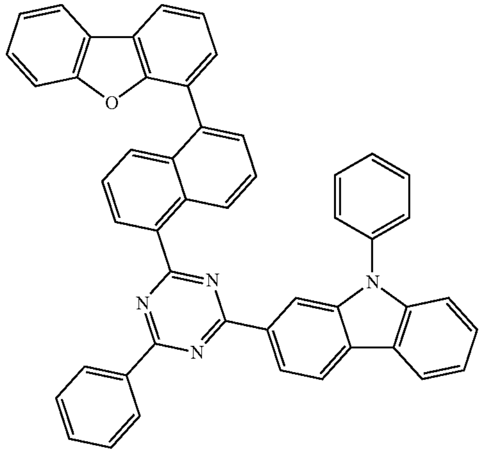

-continued
P 2-11
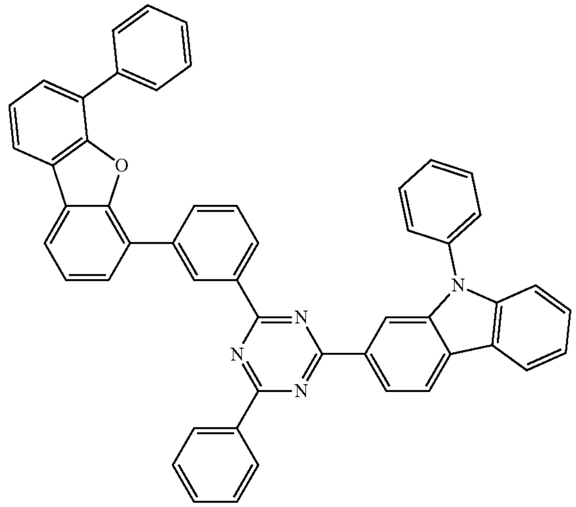
P 2-12
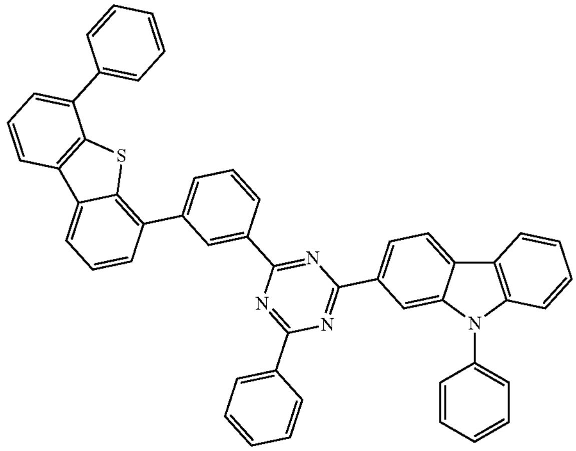
P 2-13
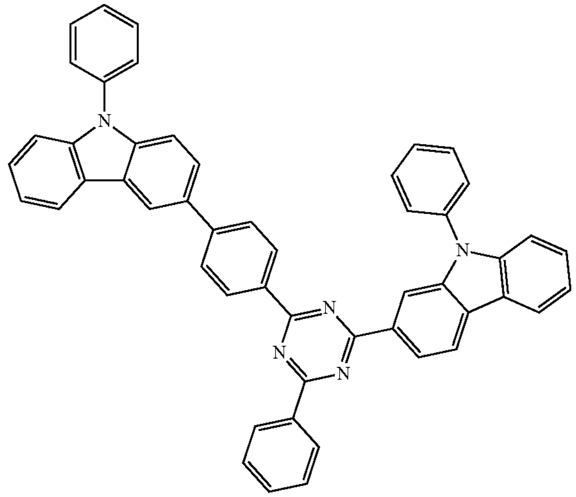
-continued
P 2-14
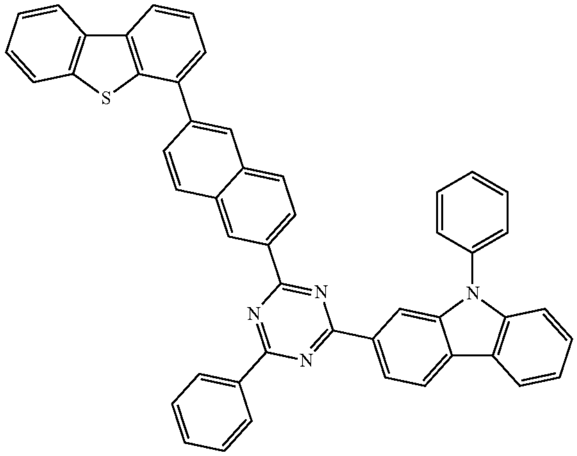
P 2-15
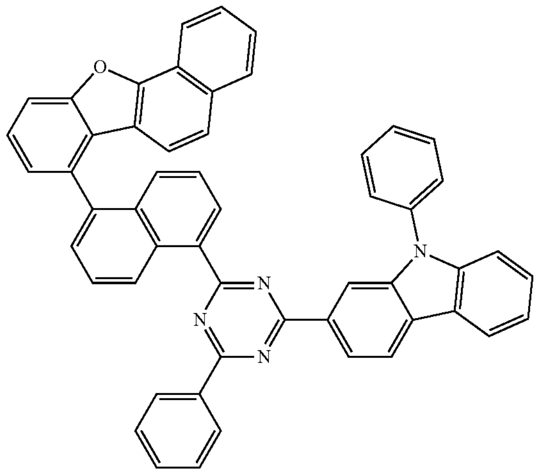
P 2-16
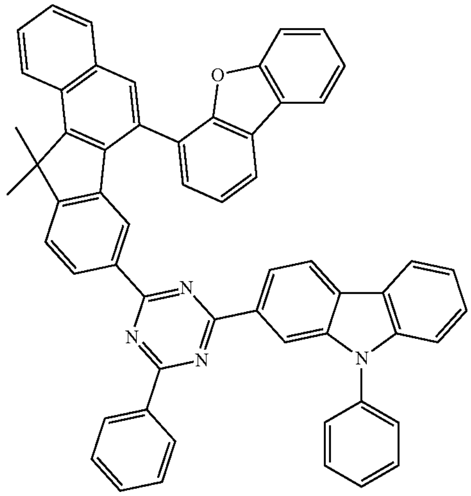

-continued
P 2-17
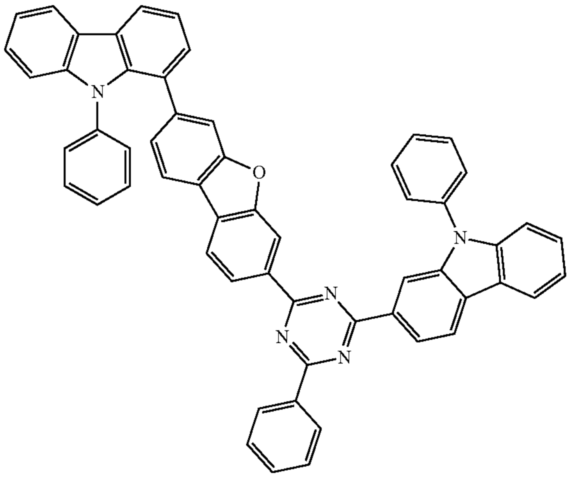
P 2-18
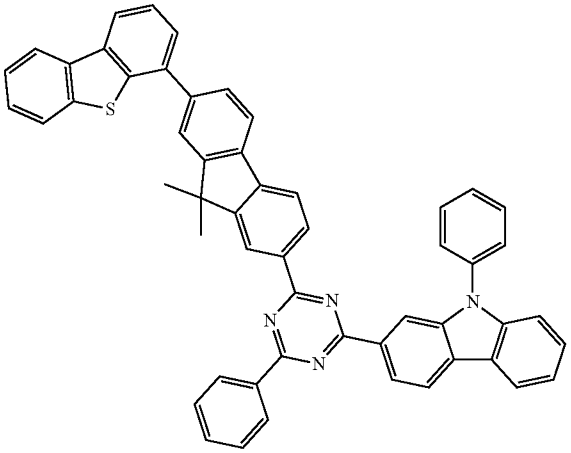
P 2-19
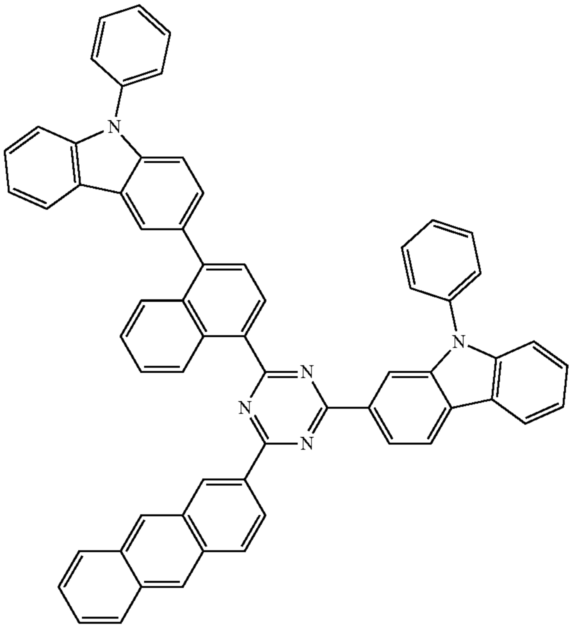
-continued
P 2-20
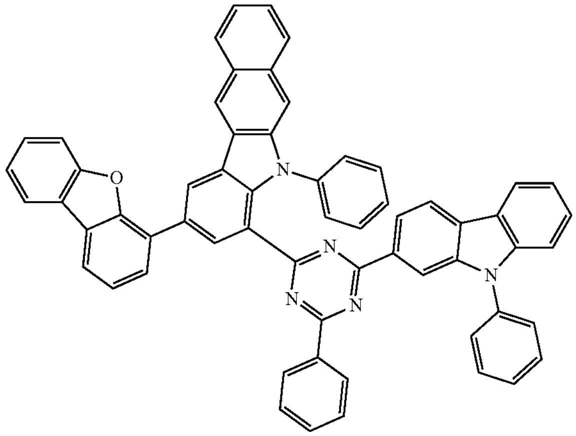
P 2-21
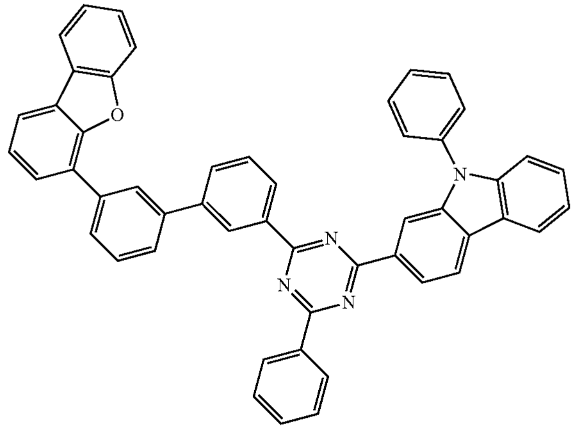
P 2-22
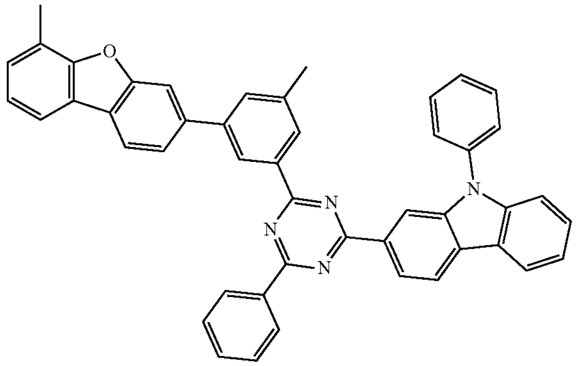

-continued
P 2-23
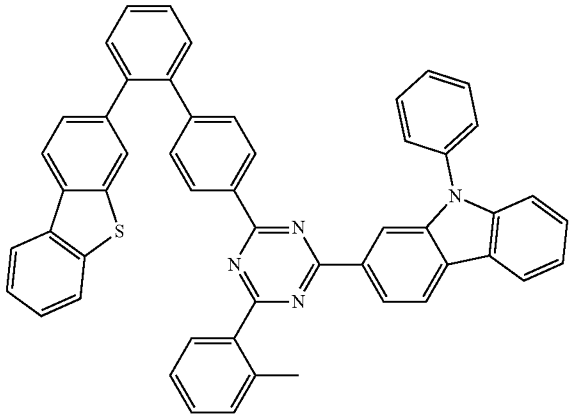
P 2-24
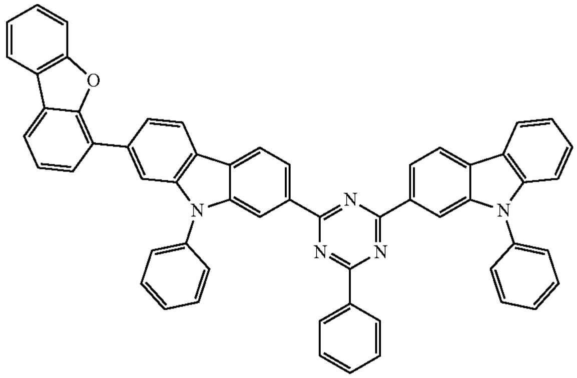
P 2-25
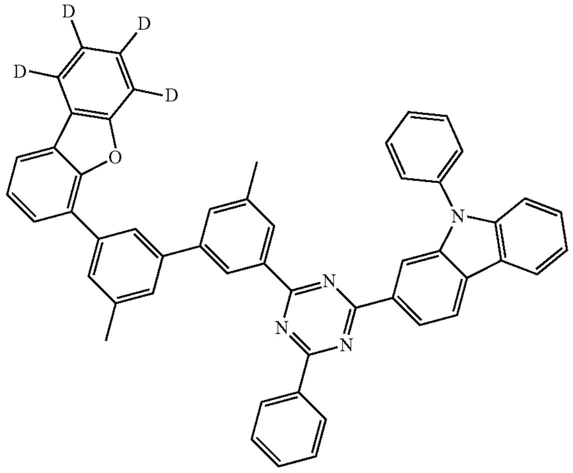
-continued
P 2-26
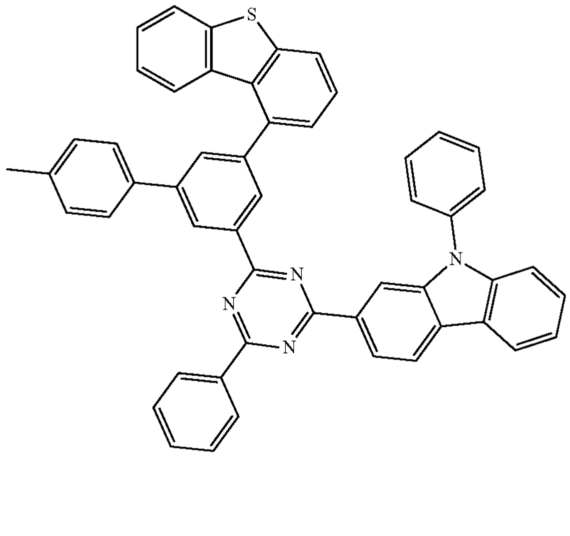
P 2-27
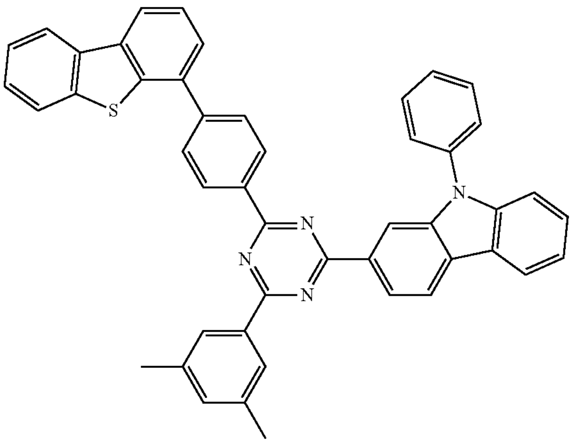
P 2-28
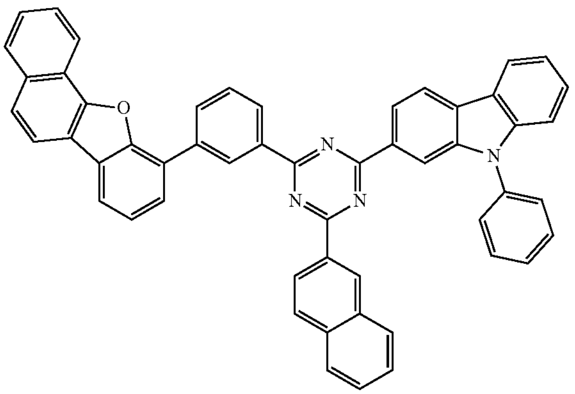

-continued
P 2-29
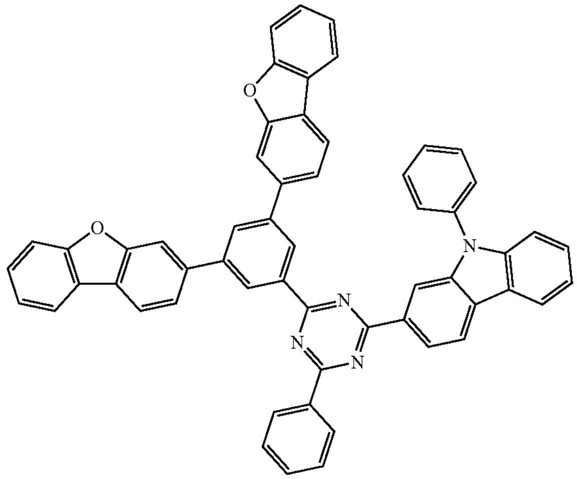
P 2-30
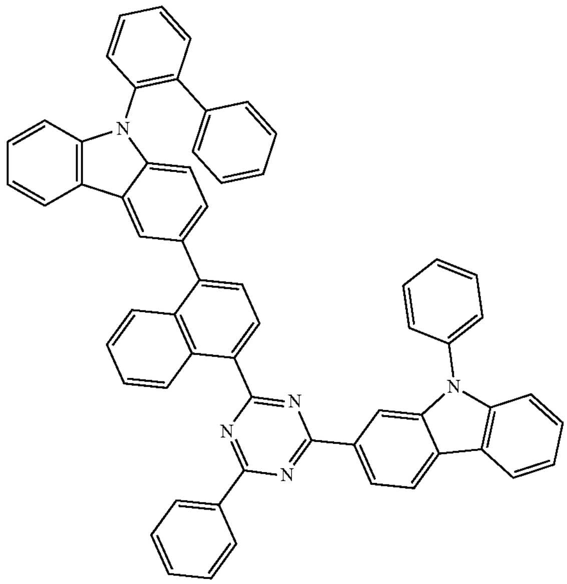
P 3-1
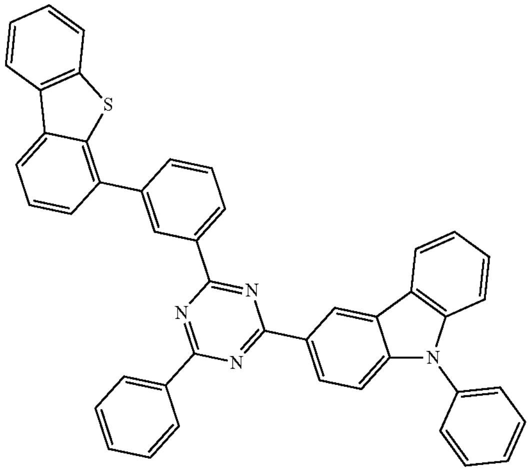
-continued
P 3-2
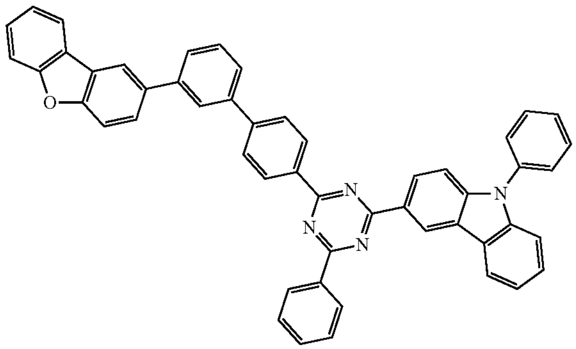
P 3-3
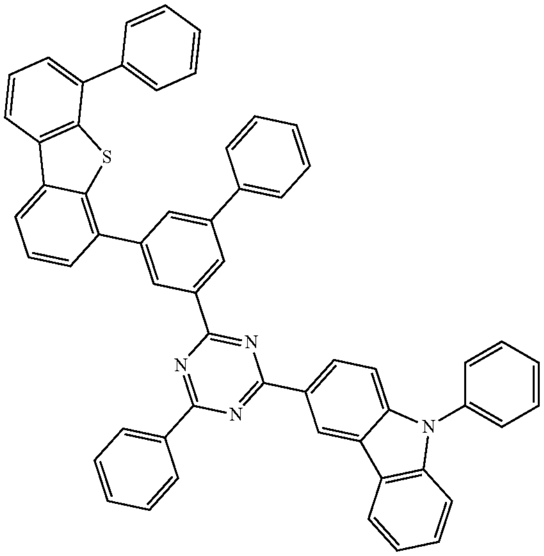
P 3-4
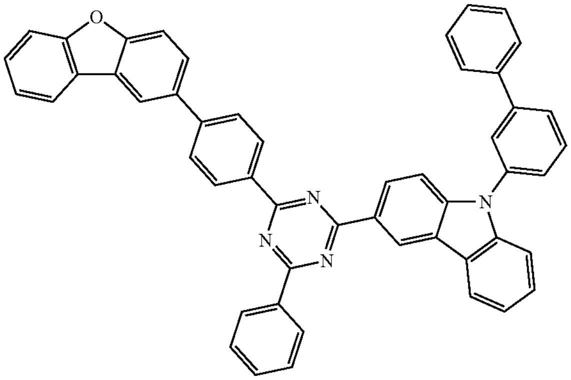

-continued
P 3-5
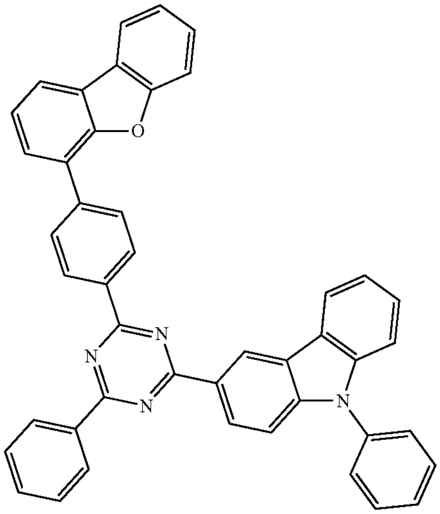
P 3-6
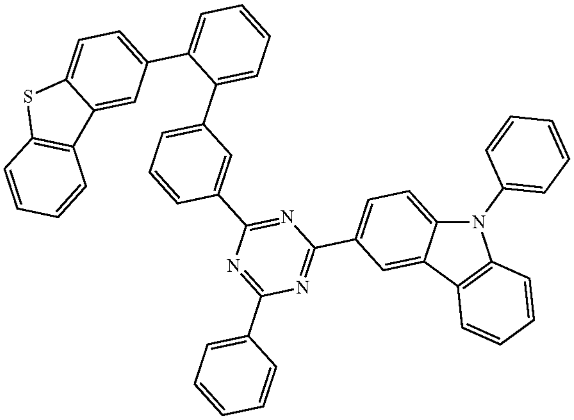
P 3-7
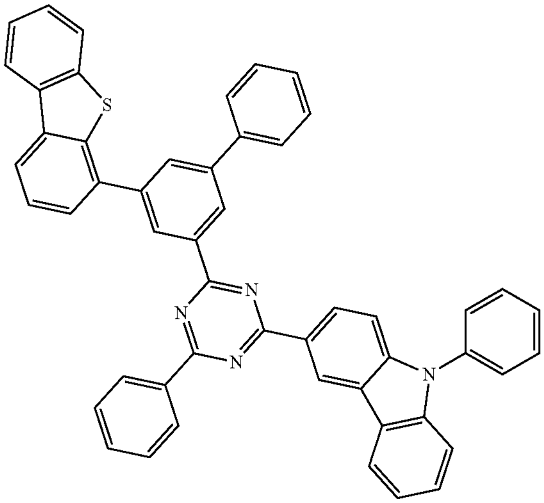
-continued
P 3-8
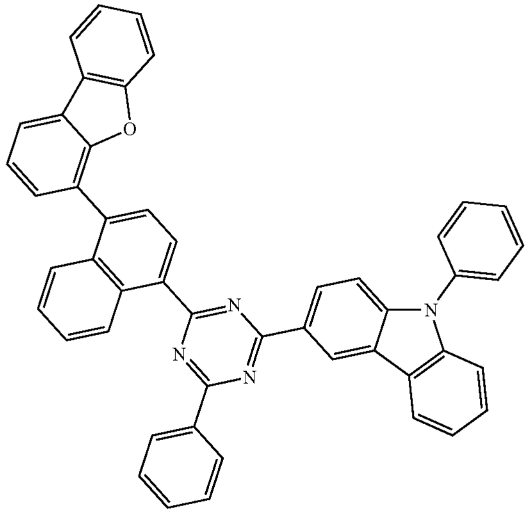
P 3-9
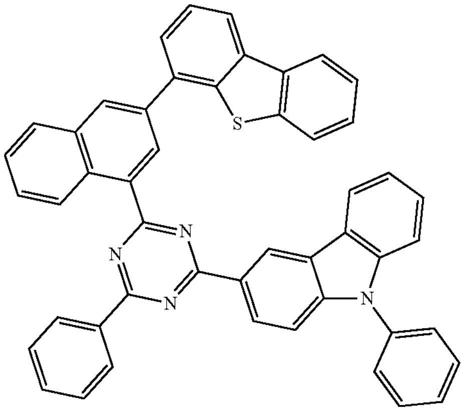
P 3-10
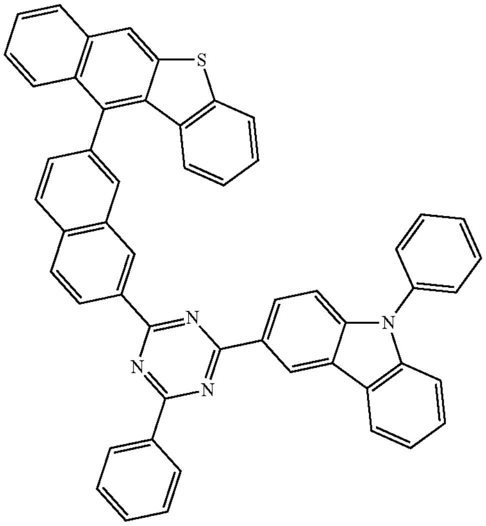

-continued
P 3-11
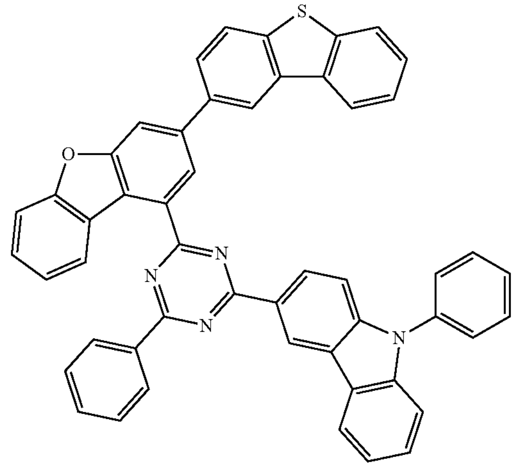
P 3-12
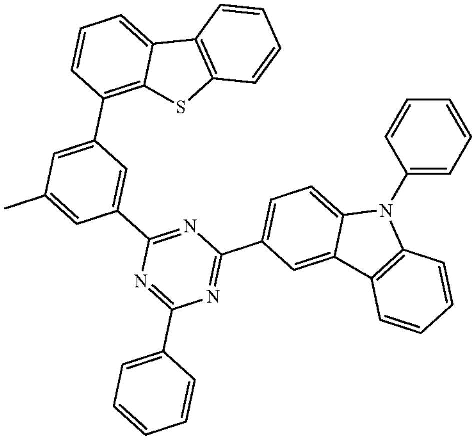
P 3-13
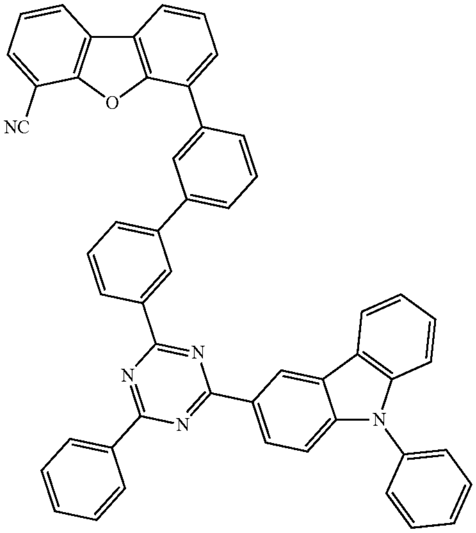
-continued
P 3-14
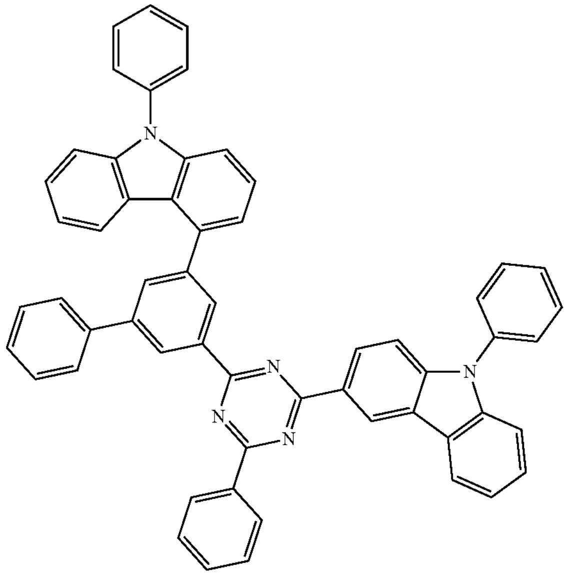
P 3-15
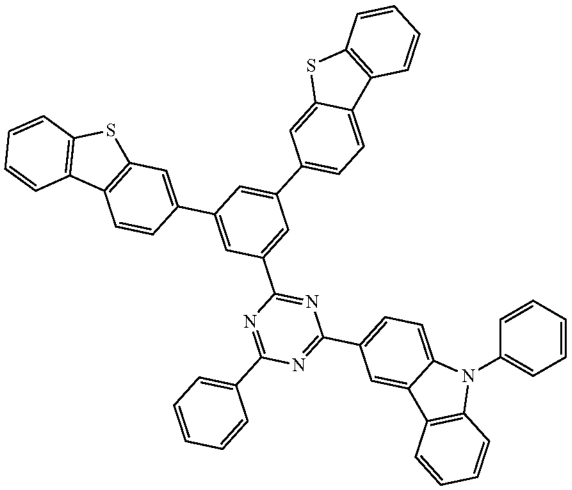
P 3-16
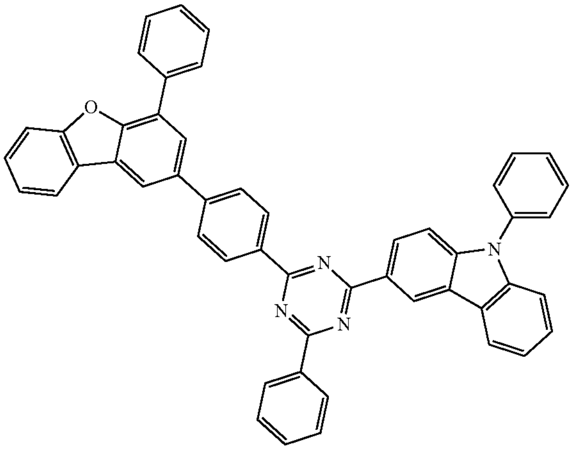

-continued
P 3-17
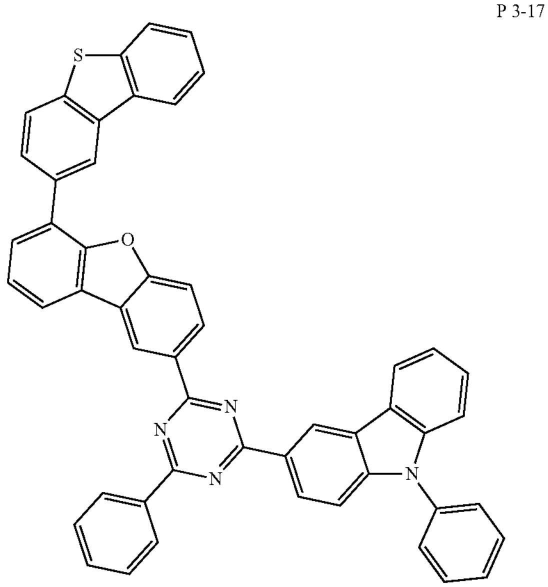
P 3-18
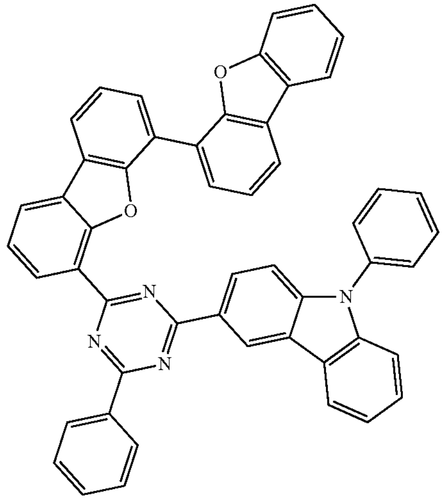
-continued
P 3-19
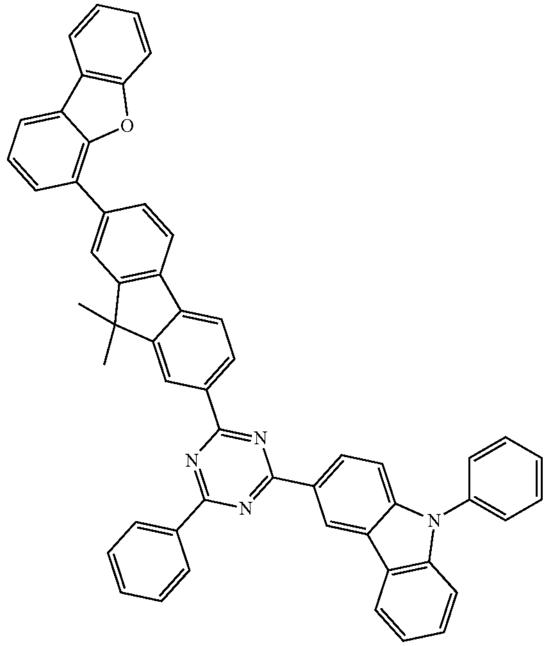
P 3-20
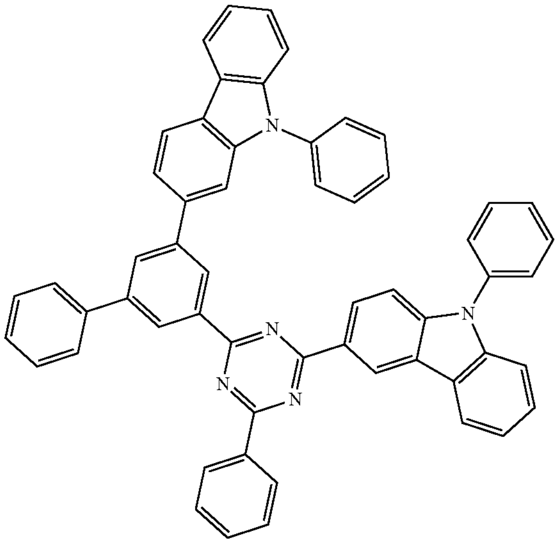
P 3-21
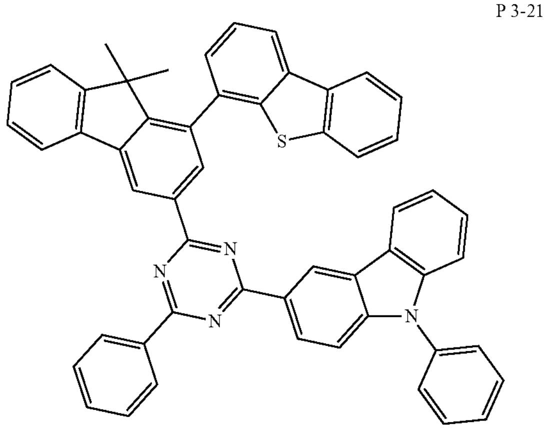

-continued
P 3-22
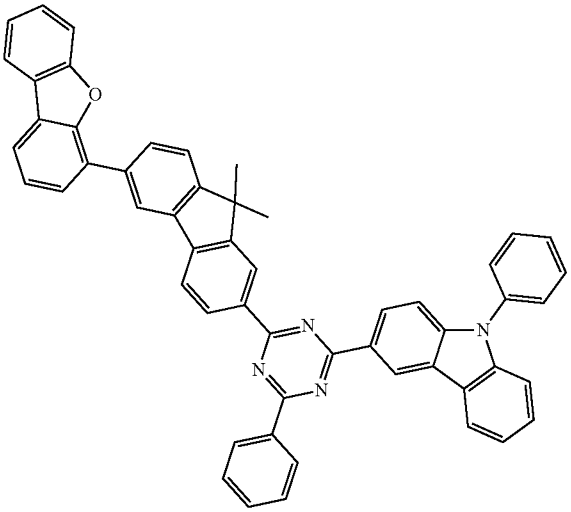
P 3-23
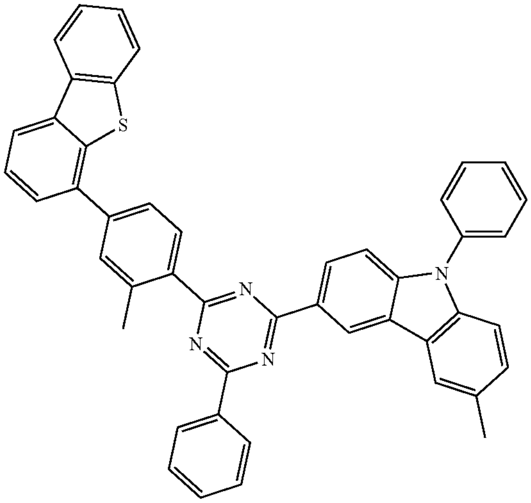
P 3-24
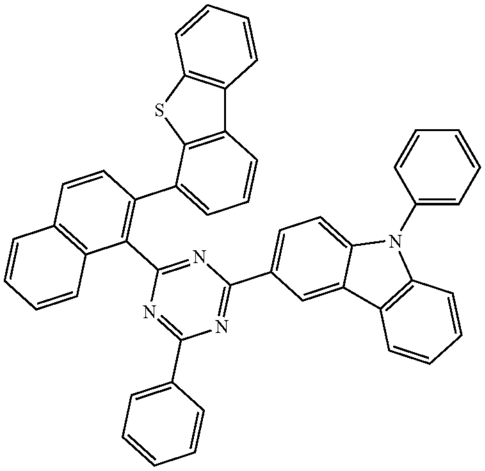
-continued
P 3-25
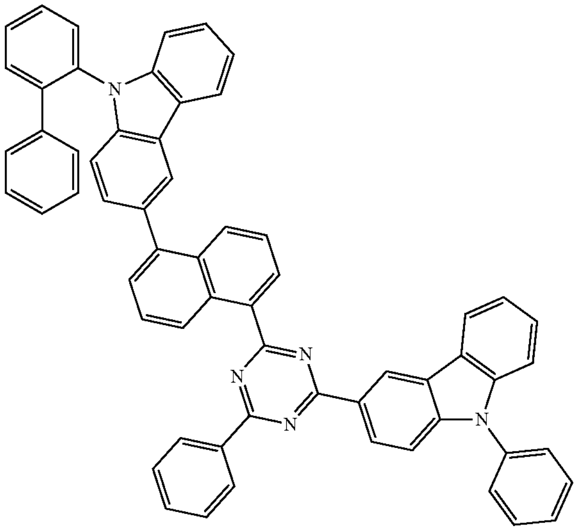
P 3-26
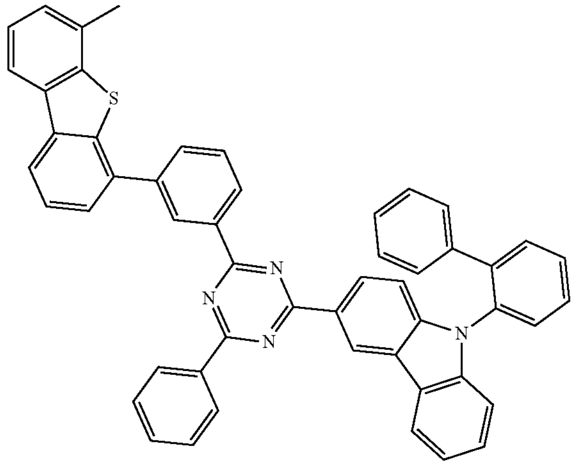
P 3-27
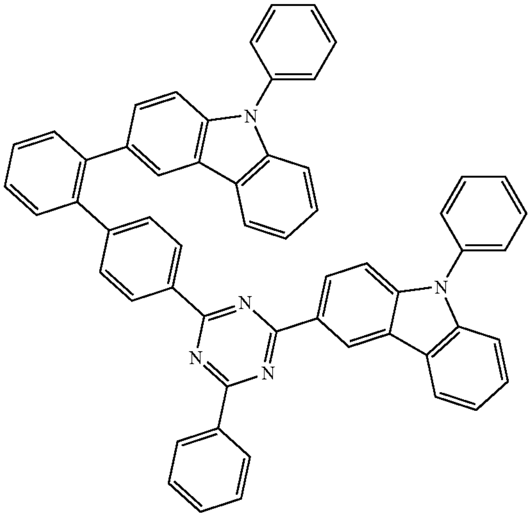

-continued
P 3-28
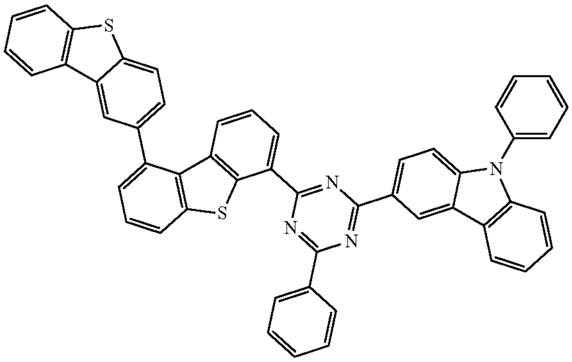
P 3-29
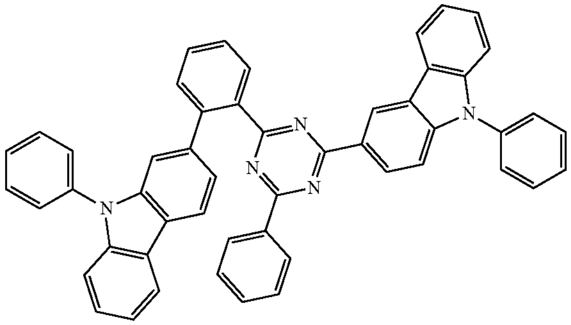
P 3-30
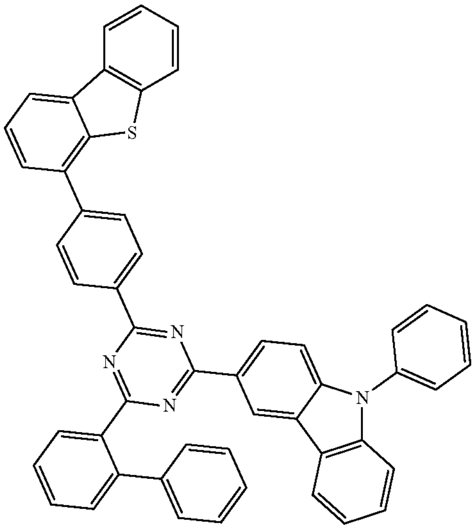
-continued
P 4-1
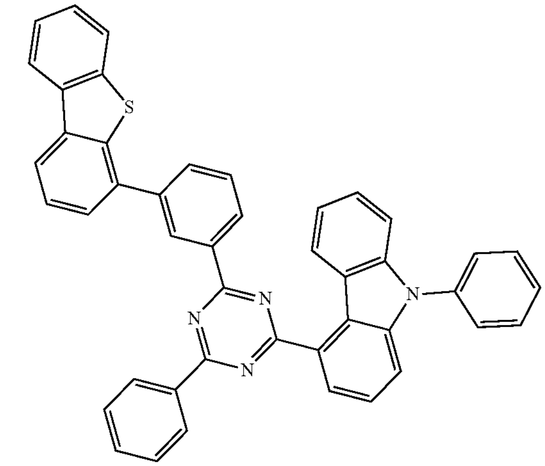
P 4-2
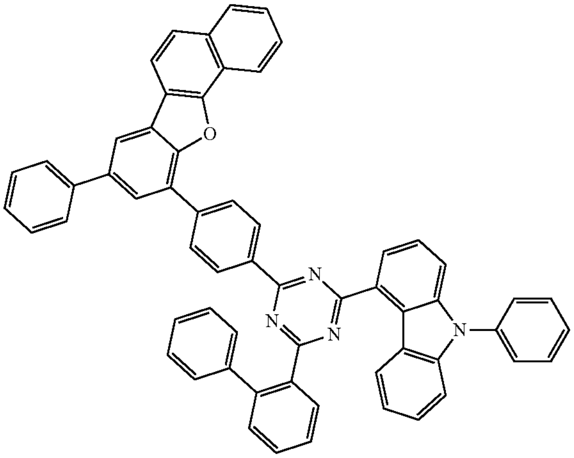
P 4-3
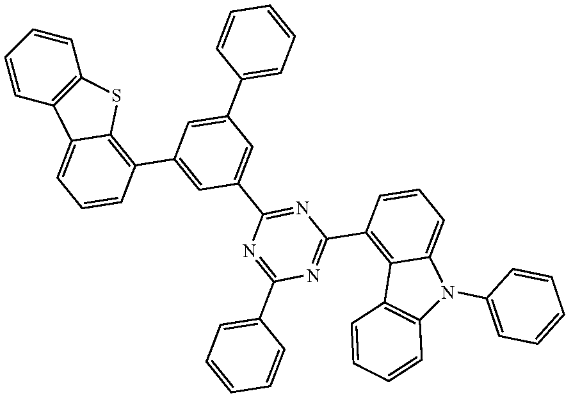

-continued
P 4-4
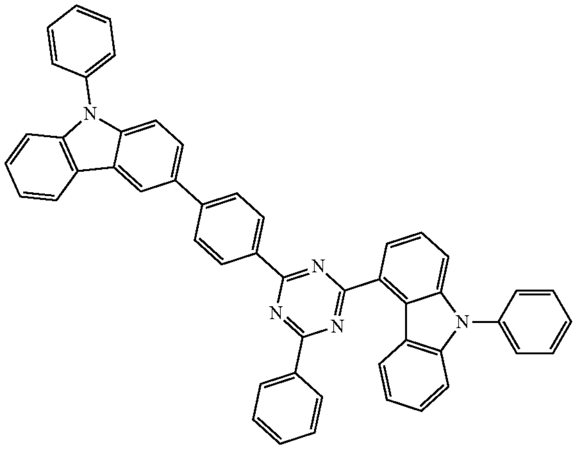
P 4-5
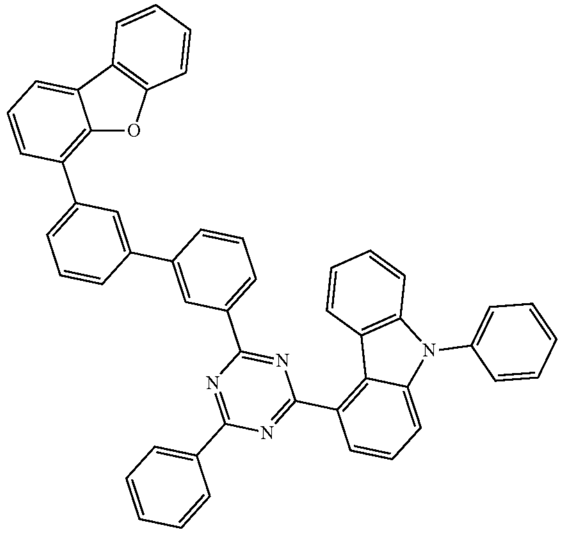
P 4-6
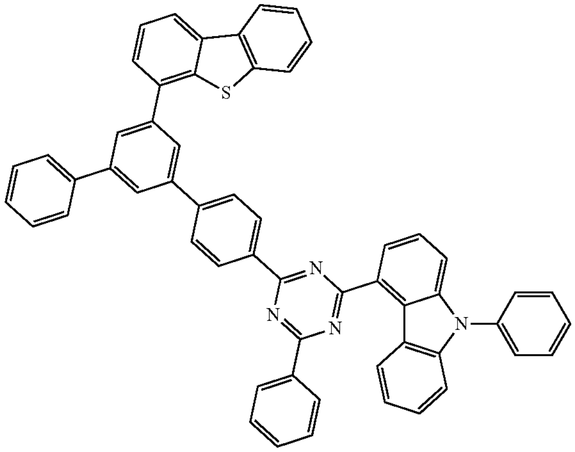
-continued
P 4-7
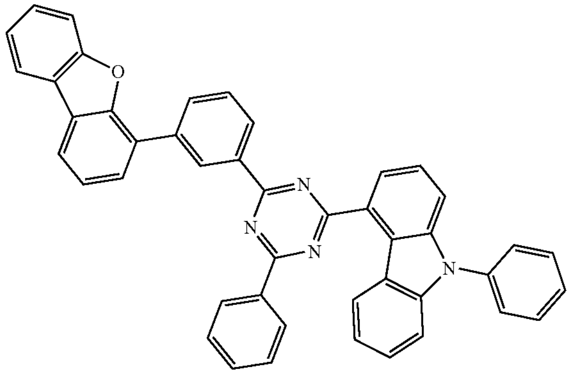
P 4-8
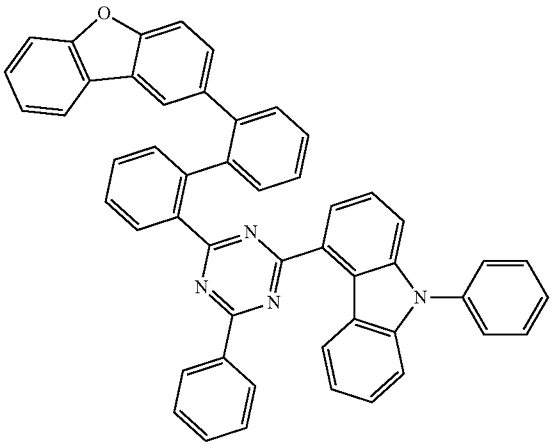
P 4-9
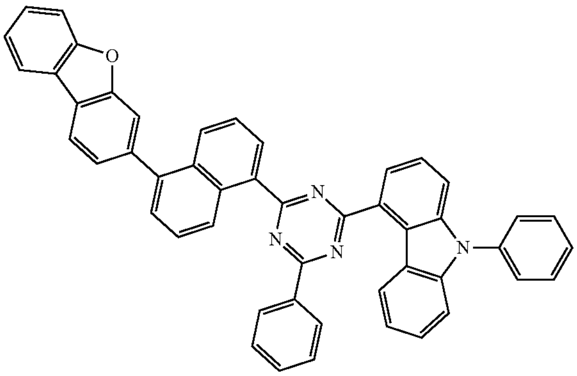

-continued
P 4-10
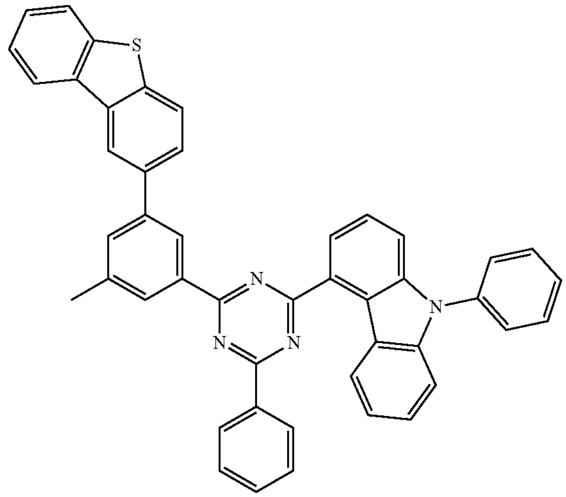
P 4-11
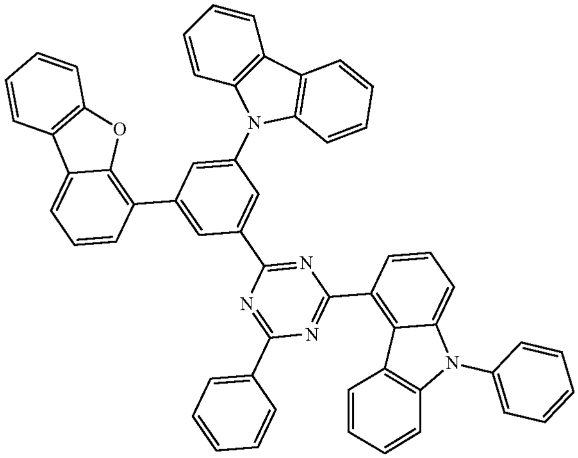
P 4-12
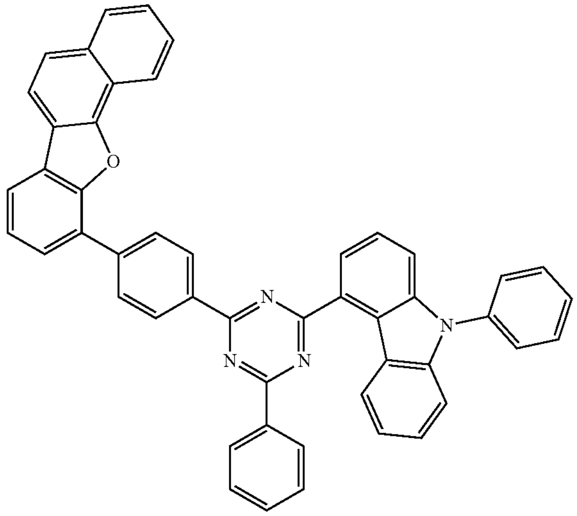
-continued
P 4-13
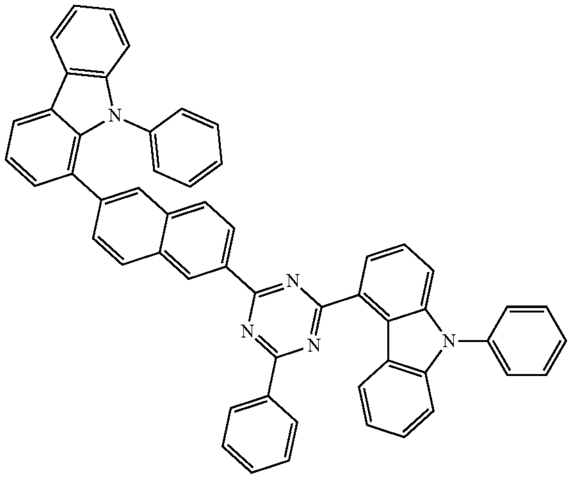
P 4-14
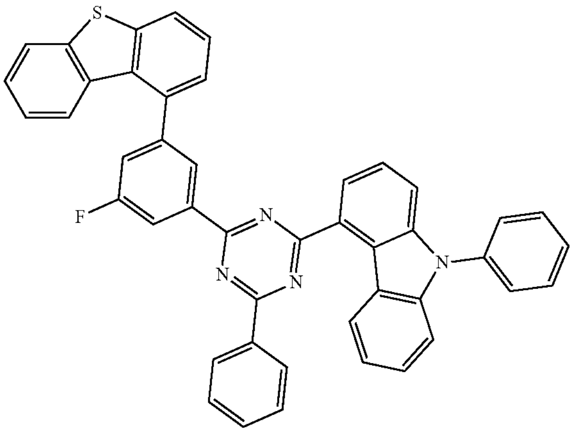
P 4-15
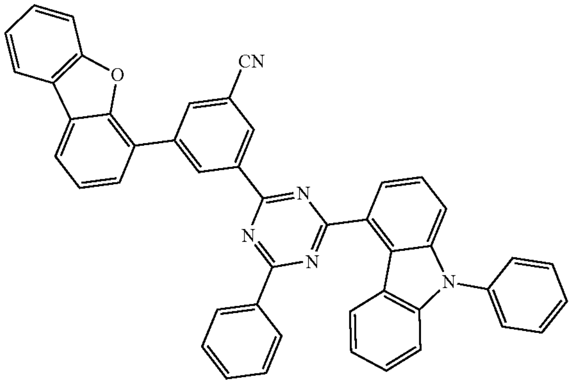

P 4-16
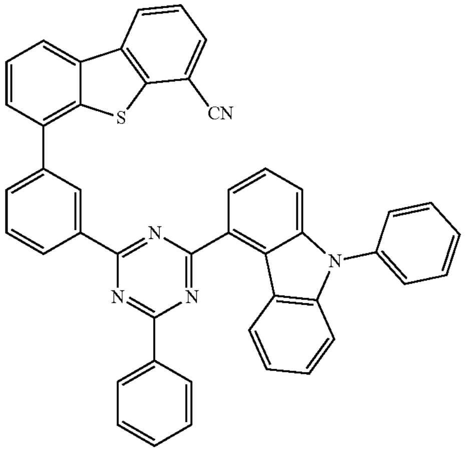
P 4-17
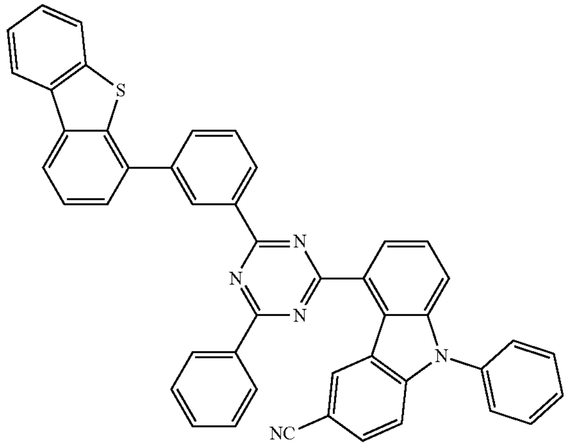
P 4-18
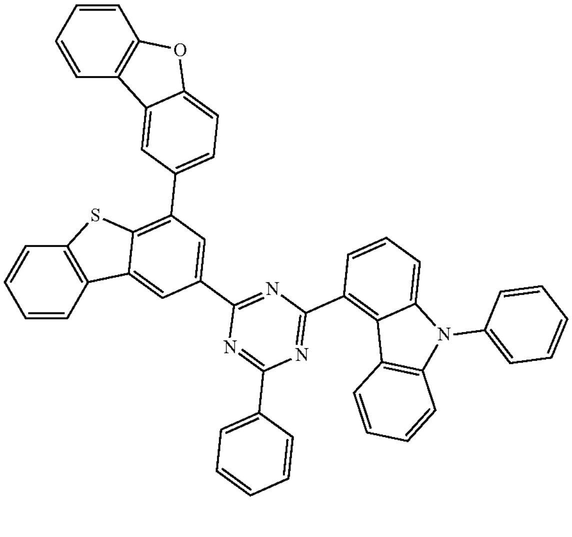
P 4-19
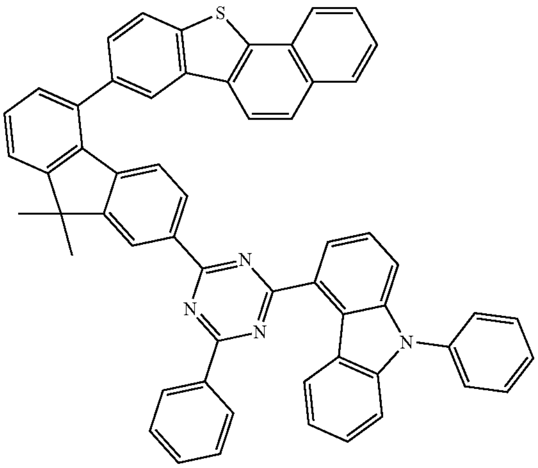
P 4-20
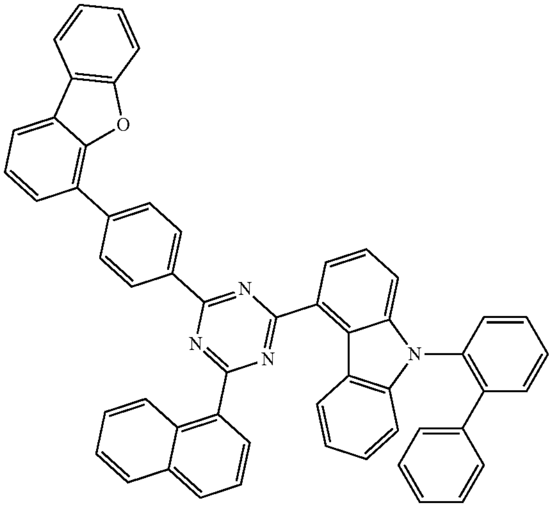
P 4-21
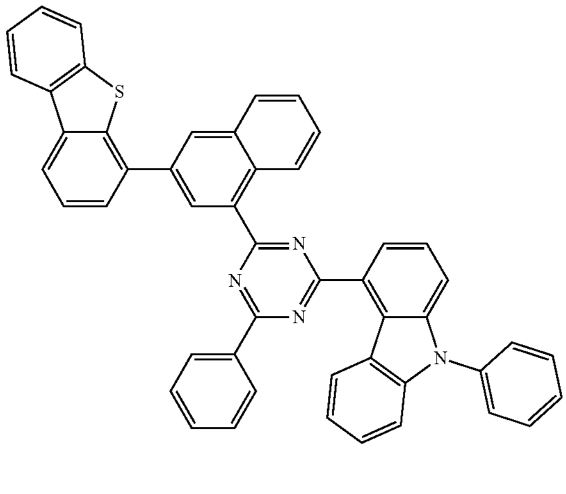

-continued
P 4-22
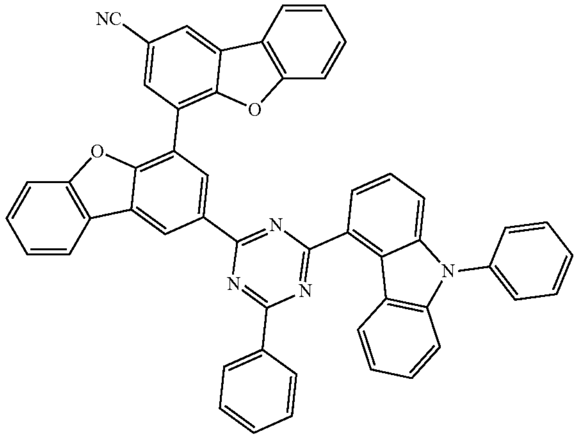
P 4-23
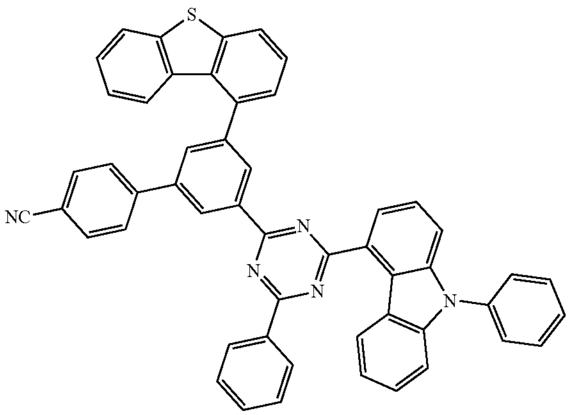
P 4-24
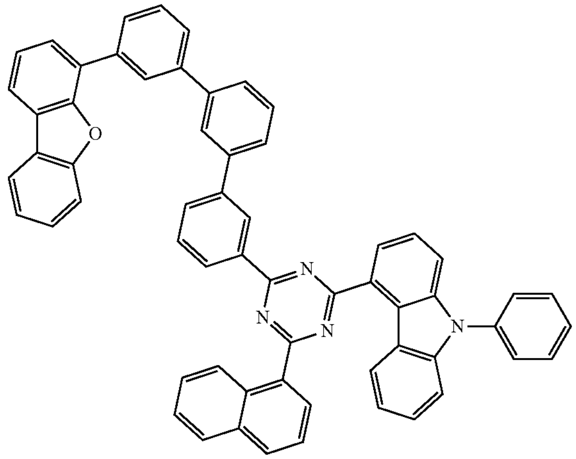
-continued
P 4-25
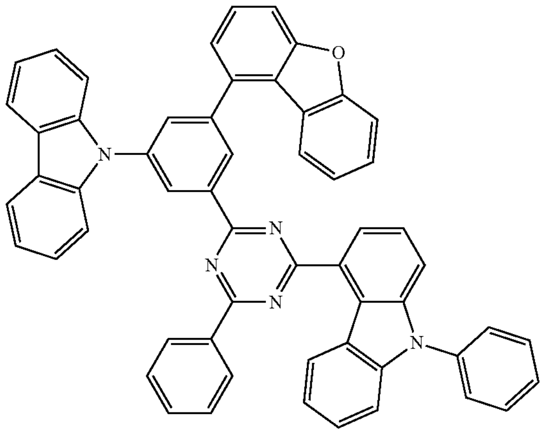
P 4-26
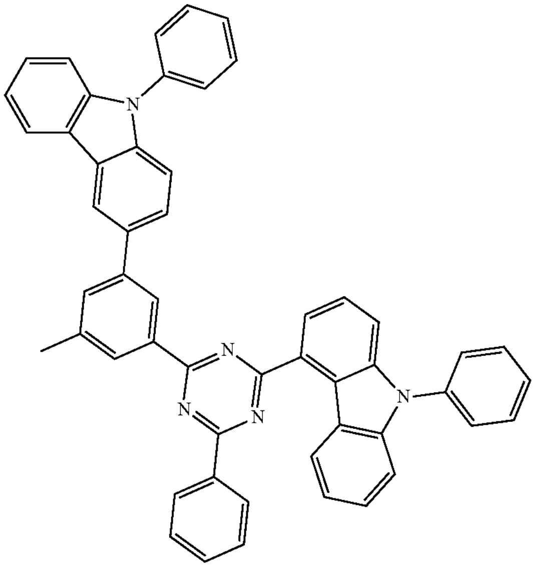
P 4-27
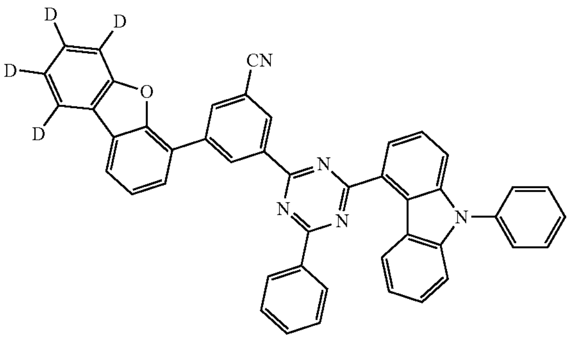

-continued

P 4-28

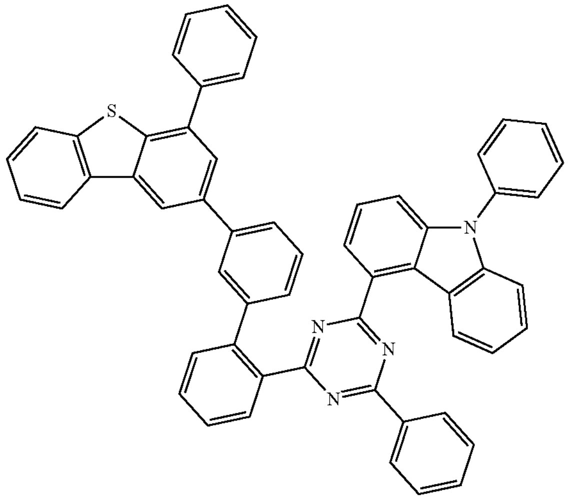

P 4-29

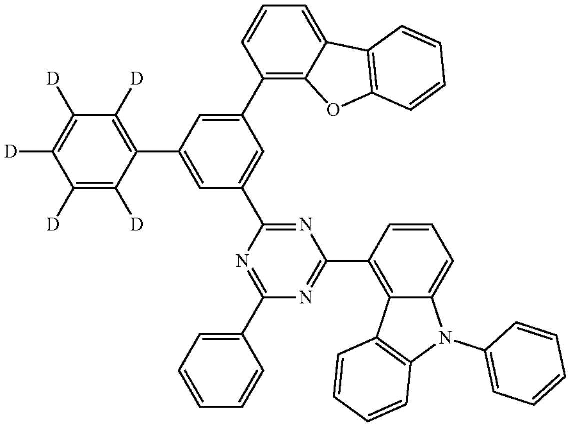

P 4-30

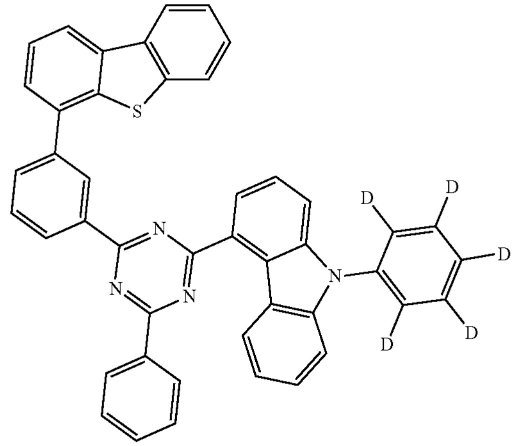

In another aspect of the present invention, the present invention provides an organic electric element comprising a first electrode, a second electrode, and an organic material layer formed between the first electrode and the second electrode, wherein the organic material layer comprises a single compound two or more compounds represented by Formula 1.

The organic material layer comprises at least one of a hole injection layer, a hole transport layer, an emission-auxiliary layer, a light emitting layer, an electron transport-auxiliary layer, an electron transport layer and an electron injection layer, preferably, the compound is comprised in the light emitting layer, more preferably the compound is used as host material of the light emitting layer.

In another aspect of the present invention, the present invention provides an electronic device comprising a display device and a control unit for driving the display device, wherein the display device comprises the organic electric element comprising compound represented by Formula 1.

Hereinafter, synthesis example of the compound represented by Formula 1 and preparation method of an organic electroluminescent element according to the present invention will be described in detail by way of examples. However, the present invention is not limited to the following examples.

Synthesis Example

The compound (final products) represented by Formula 1 according to the present invention can be synthesized by reacting Core 1 with Core 2 by the reaction route of Reaction Scheme 3 below, but there is no limitation thereto, wherein Core 1 is manufactured according to the following Reaction Scheme 1 and Core 2 is manufactured according to the following Reaction Scheme 2.

<Reaction Scheme 1>

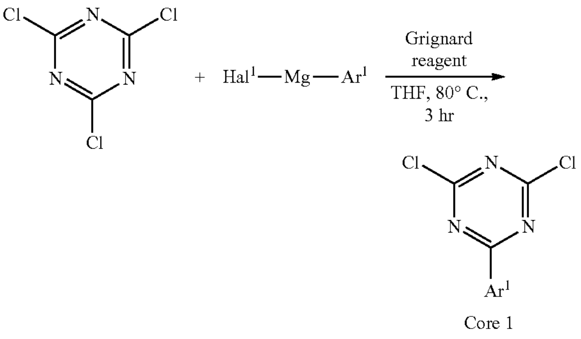

(Hal[1] is I, Br or Cl.)

<Reaction Scheme 2>

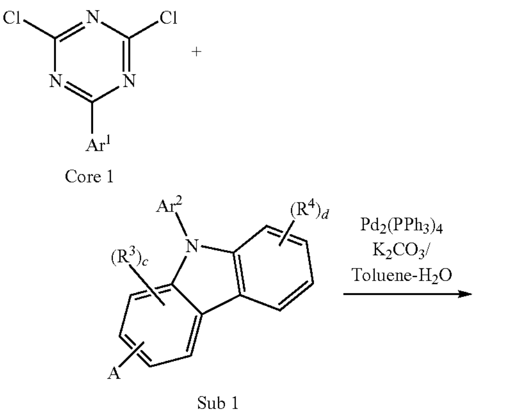

-continued

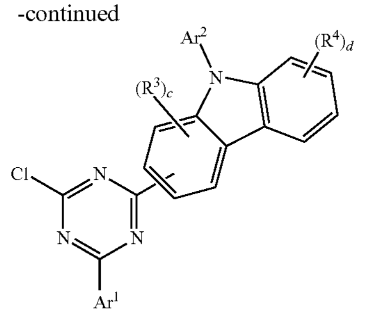

Core 2

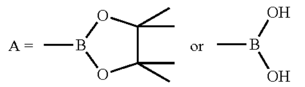

<Reaction Scheme 3>

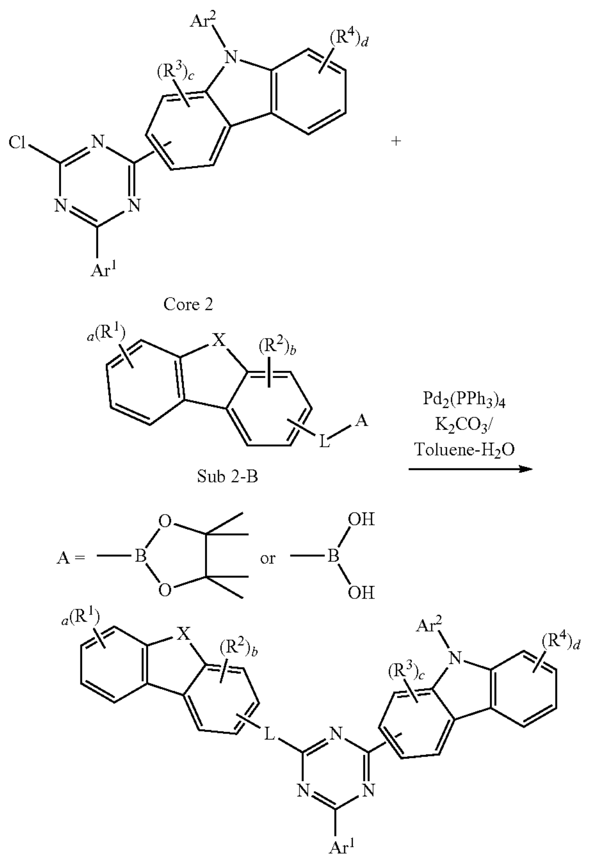

Core 2

Sub 2-B

Product

I. Synthesis of Core 1 and Core 2

Compounds belonging to Core 1 and Core 2 may be synthesized by the reaction route of the following Reaction Scheme, but are not limited thereto.

1. Synthesis Example of Core 1

(1) Synthesis of Core 1-1

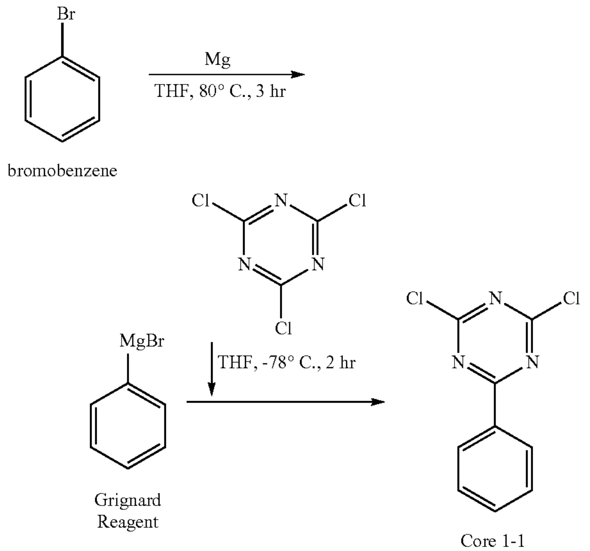

bromobenzene

Grignard Reagent

Core 1-1

Mg (26.89 g, 1106.3 mmol) was placed in a round bottom flask, and the inside of the reactor was vacuumed by connecting the dropping funnel and the reflux condenser. After that, the internal moisture is removed through flame drying and THF (2,000 mL) was placed in the reactor. Then, the mixture of bromobenzene (173.7 g, 1106.3 mmol) and THF (500 mL) was slowly dropped. At this time, the temperature of the reactor is set to reflux at 80° C. After about 3 hr, the Grignard reagent was putted through the dropping funnel of a round bottom flask containing cyanuric chloride (120.0 g, 650.8 mmol) and THF (2,500 mL). At this time, $N_2$ purging is performed so as not to meet oxygen as much as possible. After that, while slowly dropping the Grignard reagent, the temperature of the reactor is maintained at −78° C., and the reaction proceeds overnight. When the reaction was completed, the reaction product was quenched by adding water and then water in the reaction product was removed. Then, the reaction product was filtered under reduced pressure. An organic layer was dried over $MgSO_4$ and concentrated. Then, impurities were removed from the concentrate by applying a silica gel column and recrystallization to obtain 102.98 g (yield: 70%) of the product.

(2) Synthesis of Core 1-2

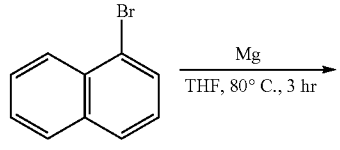

1-bromonaphthalene

-continued

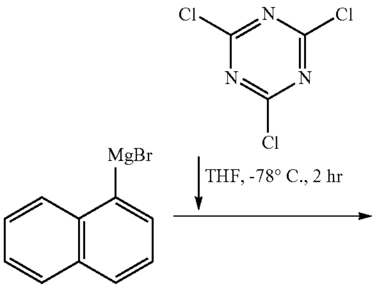

Grignard Reagent

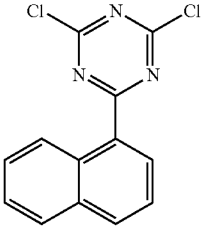

Core 1-2

Except that 1-bromonaphthalene (229.08 g, 1106.3 mmol) was used instead of bromobenzene, the synthesis was carried out in the same manner as in the synthesis method of Core 1-1 to obtain 125.78 g (yield: 70%) of the product.

(3) Synthesis of Core 1-3

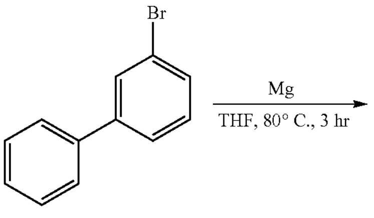

3-bromo-1,1′-biphenyl

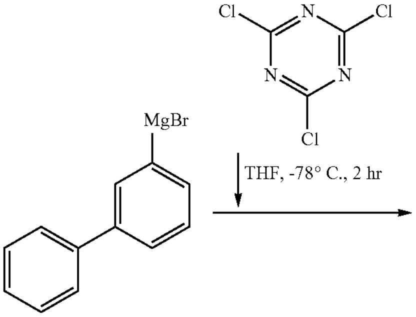

Grignard Reagent

-continued

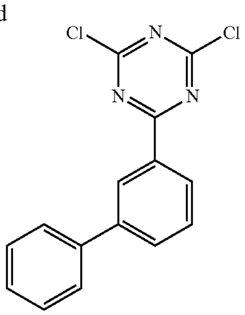

Core 1-3

Except that 3-bromo-1,1-biphenyl (257.89 g, 1106.3 mmol) was used instead of bromobenzene, the synthesis was carried out in the same manner as in the synthesis method of Core 1-1 to obtain 137.64 g (yield: 70%) of the product.

(4) Synthesis of Core 1-4

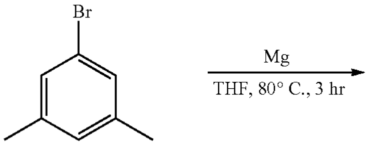

1-bromo-3,5-dimethylbenzene

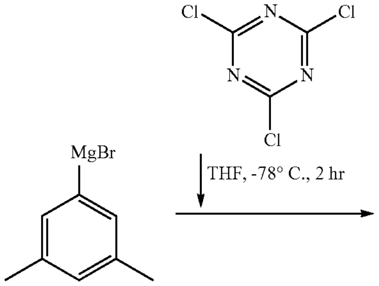

Grignard Reagent

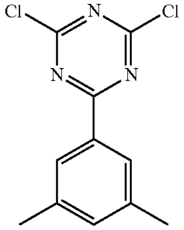

Core 1-4

Except that 1-bromo-3,5-dimethylbenzene (204.73 g, 1106.3 mmol) was used instead of bromobenzene, the synthesis was carried out in the same manner as in the synthesis method of Core 1-1 to obtain 115.76 g (yield: 70%) of the product.

2. Synthesis Example of Core 2

(1) Synthesis of Core 2-1

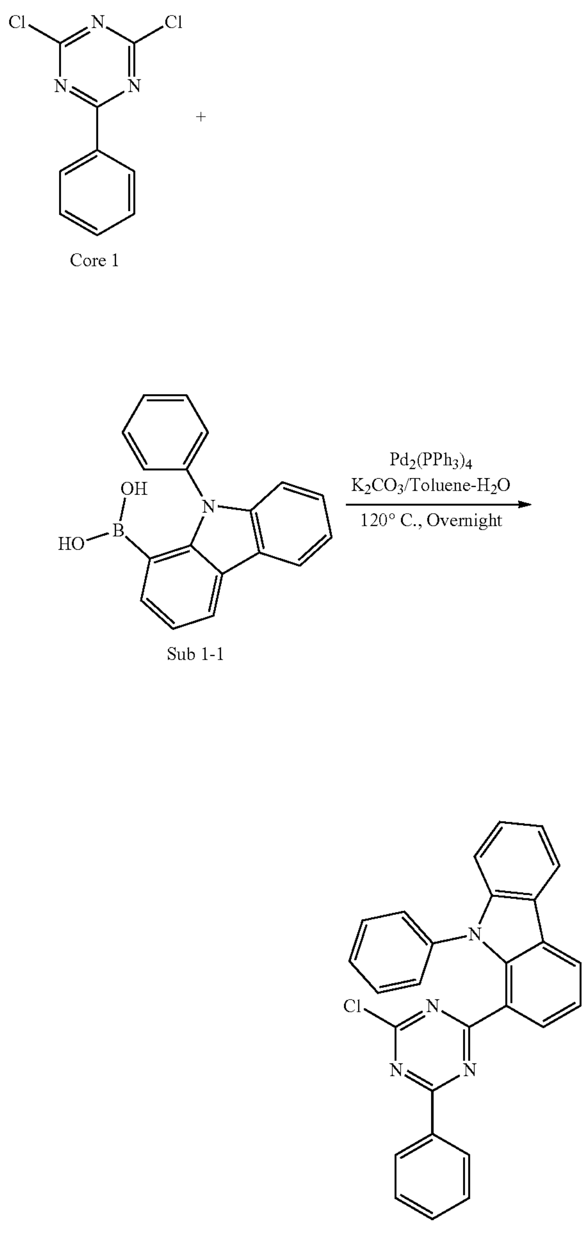

Core 1

Sub 1-1

Core 2-1

Core 1-1 (10.0 g, 44.2 mmol), Sub 1-1 ((9-phenyl-9H-carbazol-1-yl)boronic acid) (12.70 g, 44.2 mmol), $Pd_2(PPh\text{-}_3)_4$ (1.53 g, 1.3 mmol) and $K_2CO_3$ (18.34 ml, 132.7 mmol) were placed in a round bottom flask and the mixture was dissolved in toluene (200 mL) and $H_2O$ (100 mL). Then, the solution was stirred at 110° C. When the reaction was completed, water in the reaction product was removed and the reaction product was filtered under reduced pressure. After that, an organic layer was dried over $MgSO_4$ and concentrated. Then, impurities were removed from the concentrate by applying a silica gel column and recrystallization to obtain 12.45 g (yield: 65%) of the product.

(2) Synthesis of Core 2-2

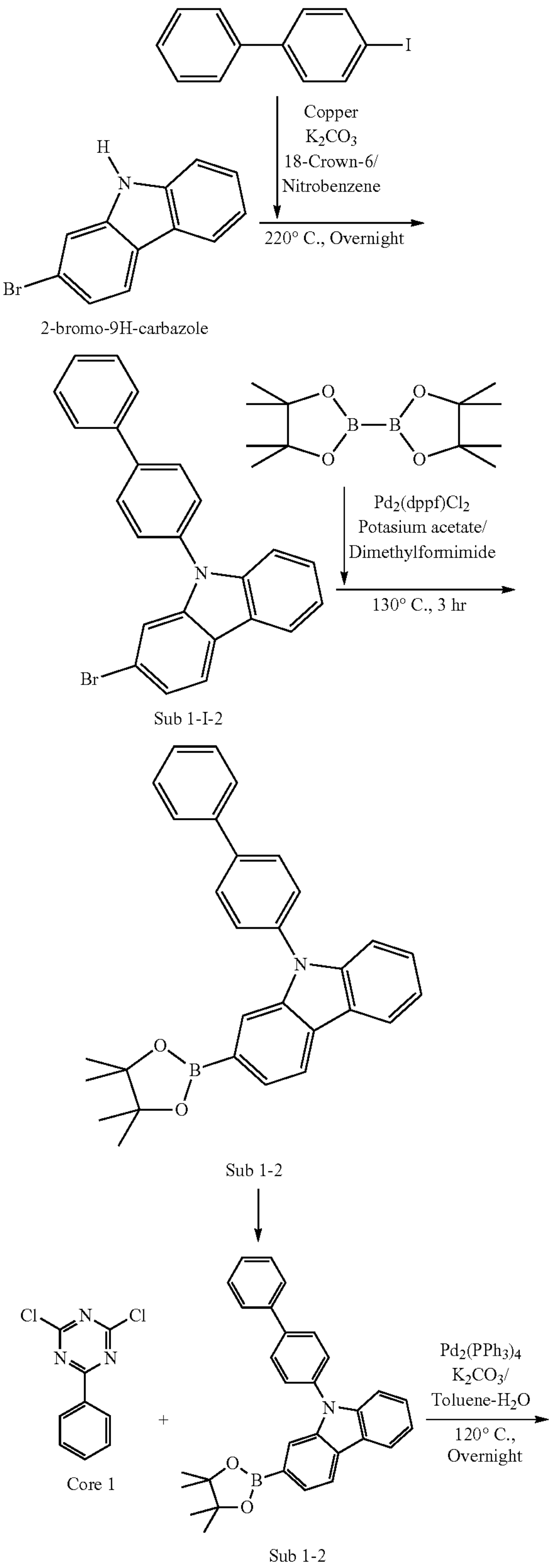

2-bromo-9H-carbazole

Sub 1-I-2

Sub 1-2

Core 1

Sub 1-2

-continued

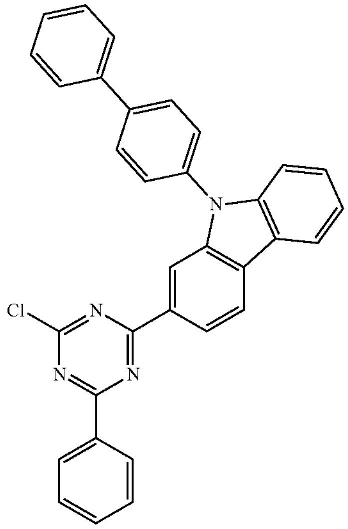

Core 2-2

Synthesis of Sub 1-I-2

2-bromo-9H-carbazole (50.0 g, 203.2 mmol), iodobiphenyl (68.29 g, 243.8 mmol), Copper (1.29 g, 20.3 mmol), 18-Crown-6 (3.66 g, 10.2 mmol), $K_2CO_3$ (84.24 g, 609.5 mmol) and nitrobenzene (1,000 mL) were placed in a round bottom flask. After raising the temperature of the mixture to 220° C., the mixture was stirred for 6 hours in a dissolved state. Upon completion of the reaction, the reaction product was concentrated under reduced pressure and quenched with water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 59.88 g (yield: 74%) of the product.

Synthesis of Sub 1-2

Sub 1-1-2 (59.88 g, 150.3 mmol), bis(pinacolato)diboron (57.27 g, 225.5 mmol), $PdCl_2$(dppf) (3.68 g, 4.5 mmol) and potassium acetate (44.26 g, 451.0 mmol) were placed in a round bottom flask and the mixture was dissolved in toluene (750 mL). Then, the solution was stirred for 3 hours at 130° C. When the reaction was completed, the reaction product was quenched by adding water and then water in the reaction product was removed. Then, the reaction product was filtered under reduced pressure. An organic layer was dried over $MgSO_4$ and concentrated. Then, impurities were removed from the concentrate by applying a silica gel column and recrystallization to obtain 46.96 g (yield: 86%) of the product.

Synthesis of Core 2-2

Sub 1-2 (10.0 g, 27.5 mmol), Core 1-2 (8.09 g, 35.8 mmol), $Pd(PPh_3)_4$ (0.95 g, 0.8 mmol) and potassium carbonate (11.42 g, 82.6 mmol) were placed in a round bottom flask and the mixture was dissolved in toluene (137 mL) and $H_2O$ (50 mL). Then, the solution was heated to 120° C. and stirred for 6 hours. When the reaction was completed, water in the reaction product was removed and an organic layer was concentrated. Then, impurities were removed from the concentrate by applying a silica gel column and recrystallization to obtain 10.51 g (yield: 75%) of the product.

(3) Synthesis of Core 2-4

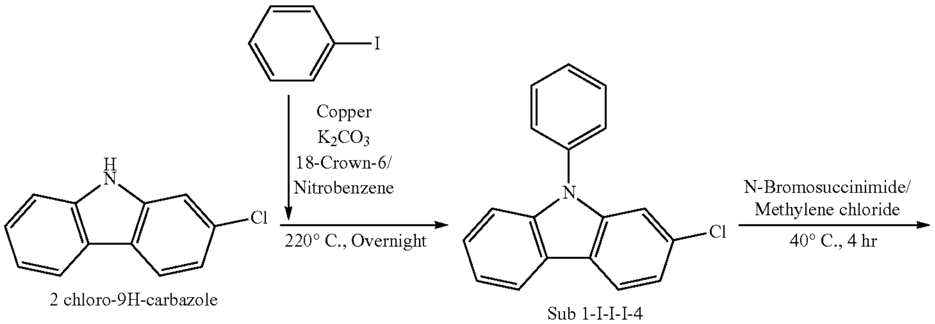

2 chloro-9H-carbazole

Sub 1-I-I-I-4

-continued

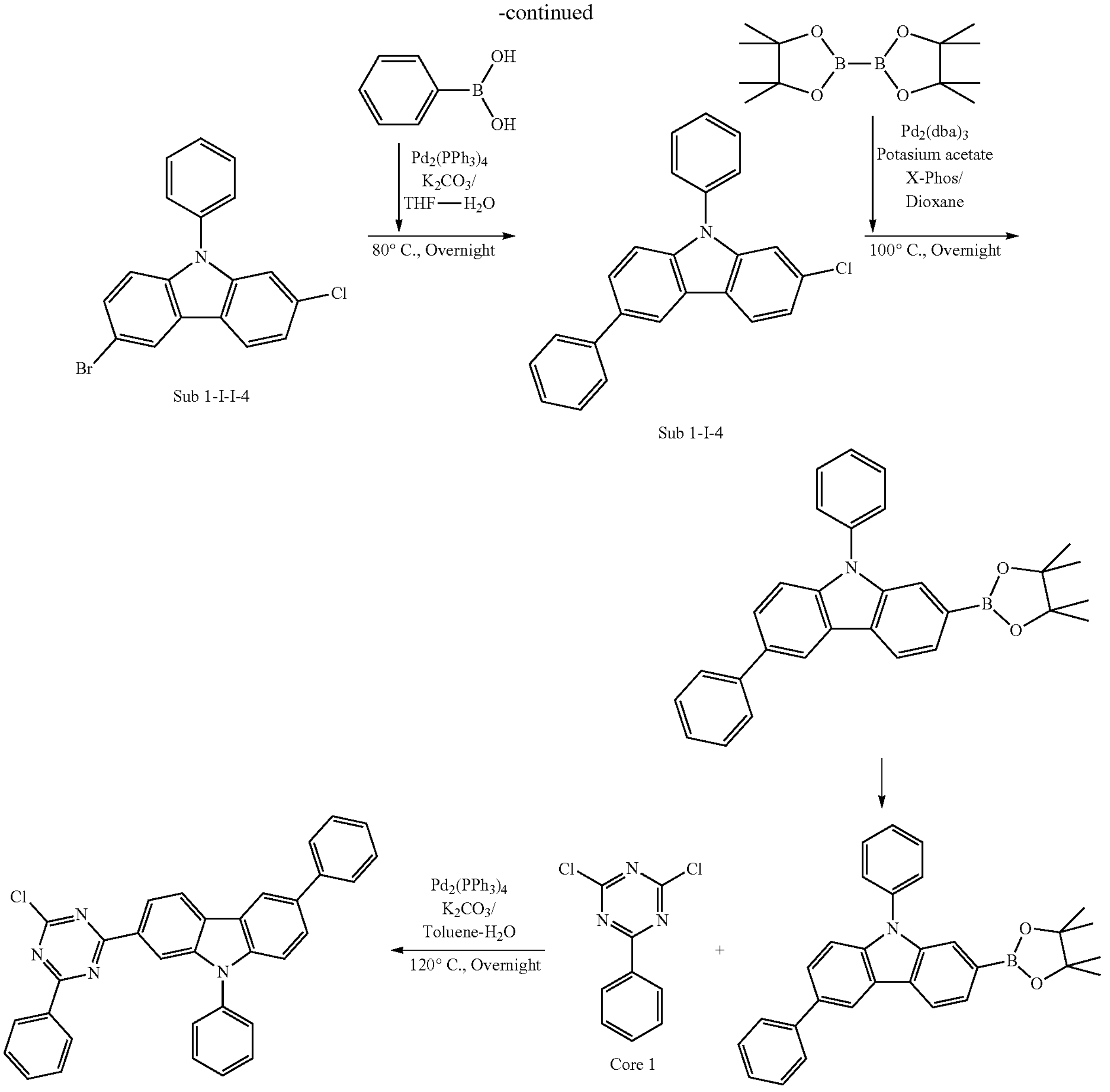

Sub 1-I-I-4

Sub 1-I-4

Core 1

Core 2-4

Sub 1-4

Synthesis of Sub 1-I-I-I-4

The reaction was carried out by using 2-chloro-9H-carbazole (100 g, 495.9 mmol), iodobenzene (505.85 g, 2,479.5 mmol), Copper (3.15 g, 49.6 mmol), 18-Crown-6 (8.94 g, 24.8 mmol), $K_2CO_3$ (205.62 g, 1,487.7 mmol) and nitrobenzene (2,500 mL) in the same manner as in the synthesis method of Sub 1-I-2 to obtain 84.02 g (yield: 61%) of the product.

Synthesis of Sub 1-I-I-4

Sub 1-I-I-I-4 (84.02 g, 302.5 mmol), N-bromosuccinimide (59.23 g, 332.8 mmol) and methylene chloride (1,500 mL) were placed in a round bottom flask. After raising the temperature of the mixture to 40° C., the mixture was stirred for 6 hours in a dissolved state. Then, the synthesis was carried out in the same manner as in the synthesis method of Sub 1-I-2 to obtain 98.18 g (yield: 91%) of the product.

Synthesis of Sub 1-I-4

Sub 1-I-I-4 (98.18 g, 275.3 mmol), phenyl boronic acid (36.92 g, 302.8 mmol), $Pd_2(PPh_3)_4$ (9.54 g, 8.3 mmol) and $K_2CO_3$ (114.14 g, 825.9 mmol) were placed in a round bottom flask and THF (1,400 mL) and $H_2O$ (700 mL) were added thereto. After the mixture was heated to 80° C., the mixture was stirred for 6 hours in a dissolved state. Then, the synthesis was carried out in the same manner as in the synthesis method of Sub 1-I-2 to obtain 85.72 g (yield: 88%) of the product.

Synthesis of Sub 1-4

Sub 1-I-4 (85.72 g, 242.2 mmol), bis(pinacolato)diboron (92.28 g, 363.4 mmol), $Pd_2(dba)_3$ (11.09 g, 12.1 mmol), potassium acetate (71.32 g, 726.7 mmol) and X-phos (11.55 g, 24.2 mmol) were placed in a round bottom flask and dioxane (1,200 mL) was added thereto. Then, the mixture was stirred for 6 hours at 100° C. When the reaction was completed, the reaction product was quenched by adding water and then water in the reaction product was removed. Then, the reaction product was filtered under reduced pressure. An organic layer was dried over $MgSO_4$ and concentrated to obtain 75.52 g (yield: 70%) of the product.

Synthesis of Core 2-4

Sub 1-4 (75.52 g, 169.6 mmol), Core 1-1 (49.83 g, 220.4 mmol), $Pd_2(PPh_3)_4$ (5.88 g, 5.1 mmol) and $K_2CO_3$ (70.31 g, 508.7 mmol) were placed in a round bottom flask and toluene (850 mL) and $H_2O$ (400 mL) were added thereto. After raising the temperature of the mixture to 80° C., the mixture was stirred for 6 hours in a dissolved state. When the reaction was completed, the reaction product was concentrated under reduced pressure and quenched with water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 53.51 g (yield: 62%) of the product.

(4) Synthesis Example of Core 2-6

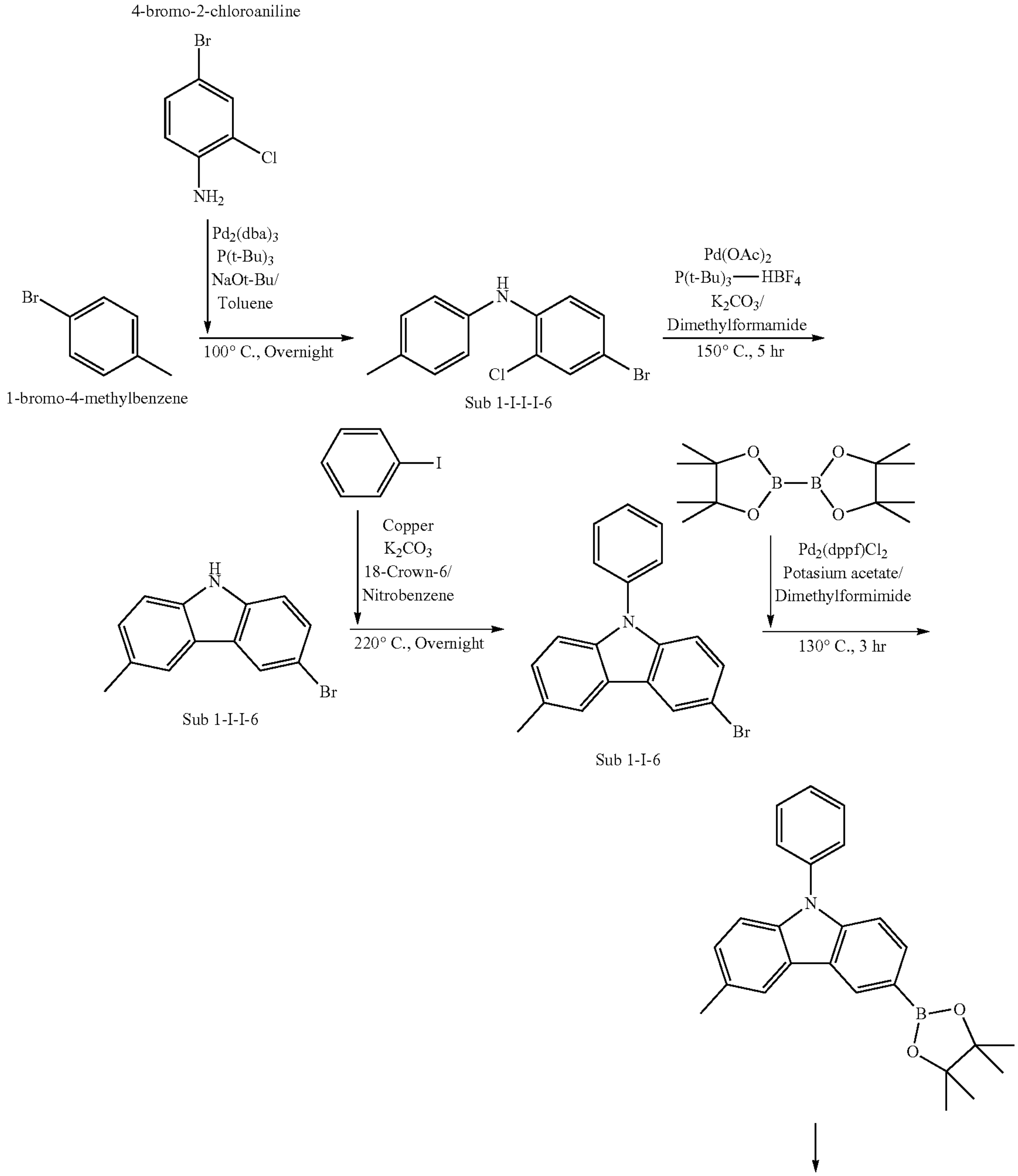

4-bromo-2-chloroaniline
1-bromo-4-methylbenzene
Sub 1-I-I-I-6
Sub 1-I-I-6
Sub 1-I-6

-continued

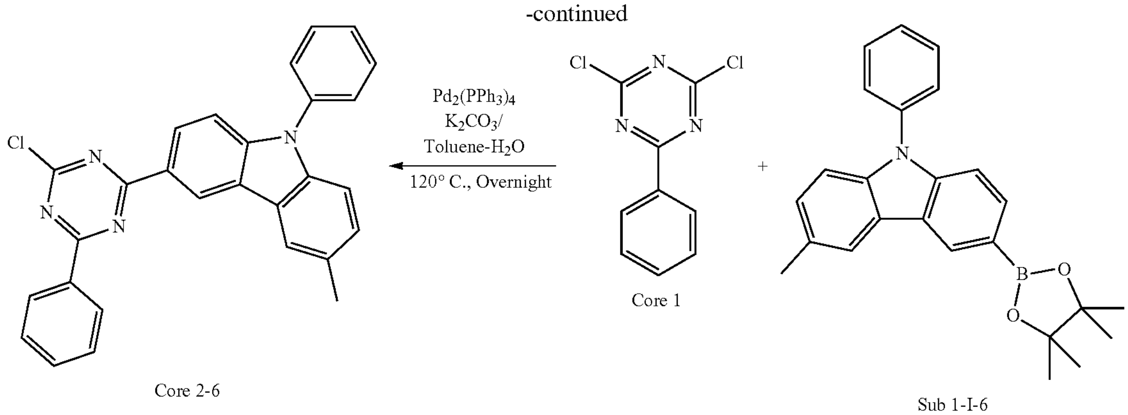

Core 2-6

Core 1

Sub 1-I-6

Synthesis of Sub-1-I-I-I-6

4-bromo-2-chloroaniline (100.0 g, 422.9 mmol), 1-bromo-4-methylbenzene (144.67 g, 845.8 mmol), $Pd_2(dba)_3$ (11.62 g, 12.7 mmol), $P(t-Bu)_3$ (6.85 ml, 33.8 mmol) and NaOt-Bu (121.94 g, 1,268.8 mmol) were placed in a round bottom flask and the mixture was dissolved in toluene (2,100 mL). Then, the solution was stirred at 110° C. When the reaction was completed, the reaction product was quenched by adding water and then water in the reaction product was removed. Then, the reaction product was filtered under reduced pressure. An organic layer was dried over $MgSO_4$ and concentrated. Then, impurities were removed from the concentrate by applying a silica gel column and recrystallization to obtain 92.82 g (yield: 74%) of the product.

Synthesis of Sub 1-I-I-6

Sub 1-I-I-I-6 (92.82 g, 313.0 mmol), $Pd(OAc)_2$ (1.41 g, 6.3 mmol), $P(t-Bu)_3$ $HBF_4$ (9.08 g, 31.3 mmol), $K_2CO_3$ (129.76 g, 938.9 mmol) and dimethylformamide (1,500 mL) were placed in a round bottom flask. After raising the temperature of the mixture to 150° C., the mixture was stirred for 5 hours in a dissolved state. When the reaction was completed, the reaction product was concentrated under reduced pressure and quenched by adding water. Then, the solid reaction product was obtained by filtering. Water was removed from the reaction product escaped as filtrate and the reaction product was filtered under reduced pressure. Thereafter, it was dried over $MgSO_4$ and concentrated. Impurities were removed from the concentrate by applying a silica gel column and recrystallization to obtain 65.94 g (yield: 81%) of the product.

Synthesis of Sub 1-I-6

Sub 1-I-I-6 (65.94 g, 253.5 mmol), iodobenzene (258.57 g, 1,267.4 mmol), Copper (1.61 g, 25.3 mmol), 18-crown-6 (4.57 g, 12.7 mmol) and $K_2CO_3$ (105.10 g, 760.5 mmol) were placed in a round bottom flask and nitrobenzene (1,200 mL) was added thereto. After raising the temperature of the mixture to 220° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 72.45 g (yield: 85%) of the product.

Synthesis of Sub 1-6

Sub 1-I-6 (72.45 g, 215.5 mmol), bis(pinacolato)diboron (60.19 g, 237.0 mmol), $PdCl_2(dppf)$ (5.28 g, 6.5 mmol), potassium acetate (63.44 g, 646.4 mmol) were placed in a round bottom flask and toluene (1,000 mL) was added thereto. The mixture was stirred for 3 hours at 100° C. When the reaction was completed, the reaction product was quenched by adding water and then water in the reaction product was removed. Then, the reaction product was filtered under reduced pressure. An organic layer was dried over $MgSO_4$ and concentrated to obtain 73.51 g (yield: 89%) of the product.

Synthesis of Core 2-6

Sub 1-6 (73.51 g, 191.8 mmol), Core 1-1 (56.36 g, 249.3 mmol), $Pd_2(PPh_3)_4$ (6.65 g, 5.8 mmol) and $K_2CO_3$ (79.52 g, 575.3 mmol) were placed in a round bottom flask and toluene (950 mL) and $H_2O$ (450 mL) were added thereto. After raising the temperature of the mixture to 80° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 59.14 g (yield: 69%) of the product.

(5) Synthesis Example of Core 2-7

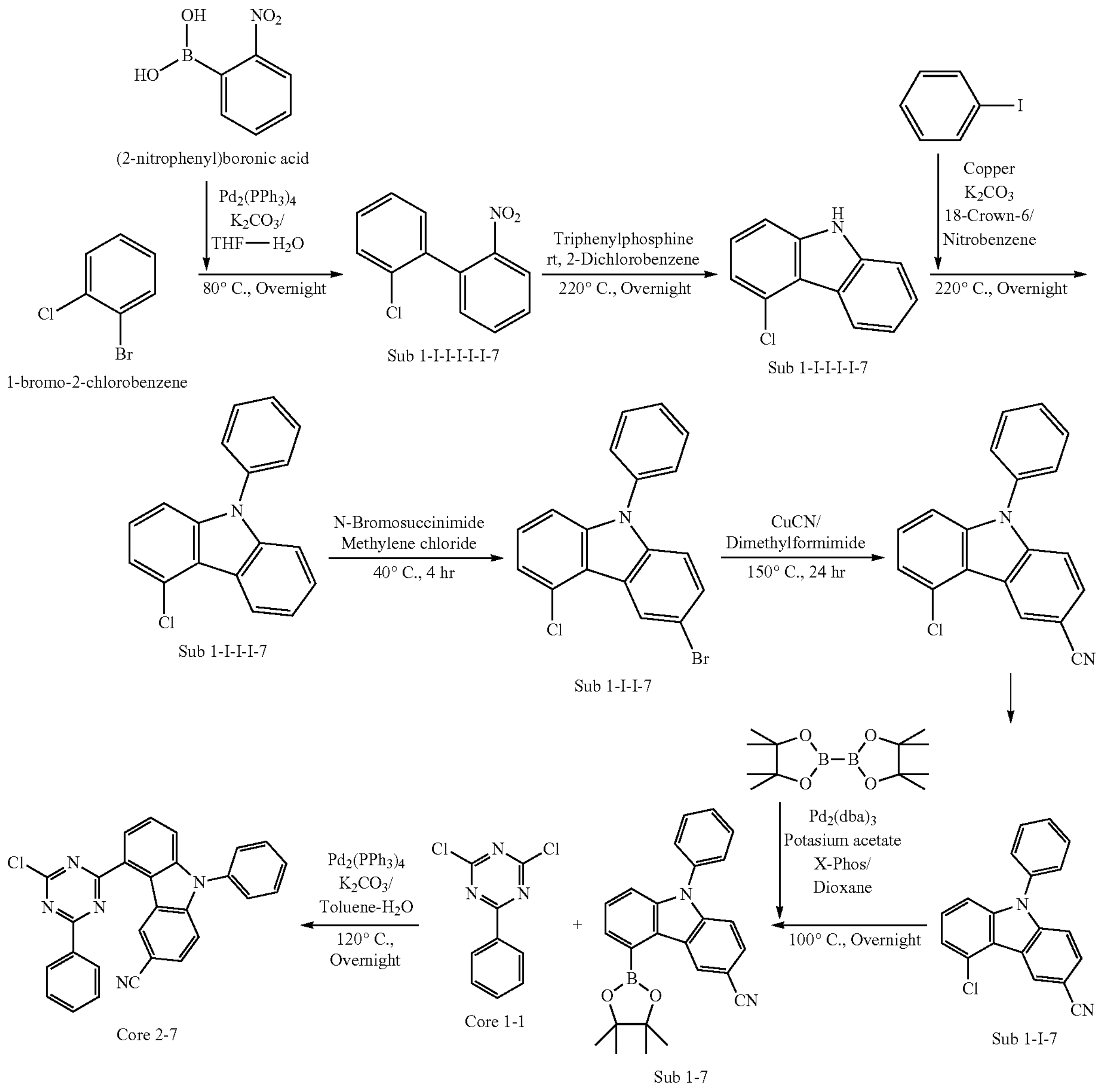

Synthesis of Sub 1-I-I-I-I-I-7

1-bromo-2-chlorobenzene (100.0 g, 522.3 mmol), (2-nitrophenyl)boronic acid (87.19 g, 522.3 mmol), $Pd_2(PPh_3)_4$ (18.11 g, 15.7 mmol) and $K_2CO_3$ (216.57 g, 1,567.0 mmol) were placed in a round bottom flask and tetrahydrofuran (2,500 mL) and $H_2O$ (1,250 mL) were added thereto. After raising the temperature of the mixture to 80° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 93.97 g (yield: 77%) of the product.

Synthesis of Sub 1-I-I-I-I-7

Sub 1-III-I-I-I-7 (93.97 g, 402.2 mmol), triphenylphosphine (316.47 g, 1,206.5 mmol) and 1,2-dichlorobenzene (2,000 mL) were placed in a round bottom flask. After raising the temperature of the mixture to 220° C., the mixture was stirred for 16 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 66.50 g (yield: 82%) of the product.

Synthesis of Sub 1-I-I-I-7

Sub 1-I-I-I-I-7 (66.50 g, 329.8 mmol), iodobenzene (336.39 g, 1,648.8 mmol), copper (2.10 g, 33.0 mmol), 18-crown-6 (5.94 g, 16.5 mmol) and $K_2CO_3$ (136.74 g, 989.3 mmol) were placed in a round bottom flask and nitrobenzene (1,500 mL) was added thereto. After raising the temperature of the mixture to 220° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 75.11 g (yield: 82%) of the product.

Synthesis of Sub 1-I-I-7

Sub 1-I-I-I-7 (75.11 g, 270.4 mmol) and N-bromosuccinimide (52.95 g, 297.5 mmol) were placed in a round bottom flask and methylene chloride (1,300 mL) was added thereto. After raising the temperature of the mixture to 40° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 51.12 g (yield: 53%) of the product.

Synthesis of Sub 1-I-7

Sub 1-I-I-7 (51.12 g, 143.3 mmol) and CuC (42.12 g, 186.3 mmol) were placed in a round bottom flask and the mixture was dissolved in dimethylformimide (700 mL). The solution was stirred for 24 hours at 150° C. and the solution was cooled to room temperature. After adding ammonia aqueous (60 mL) and water (60 mL) thereto, the mixture was extracted three times with $CH_2Cl_2$ (50 mL). The collected organic layer was dried over $MgSO_4$ and the residue was obtained by evaporation of the solvent. Then, Impurities were removed from the residue by applying a silica gel column and recrystallization to obtain 39.49 g (yield 91%) of the product.

Synthesis of Sub 1-7

Sub 1-I-7 (39.49 g, 130.4 mmol), bis(pinacolato)diboron (49.68 g, 195.7 mmol), $Pd_2(dba)_3$ (5.97 g, 6.5 mmol), potassium acetate (38.40 g, 391.3 mmol) and X-phos (6.22 g, 13.0 mmol) were placed in a round bottom flask and dioxane (650 mL) was added thereto. The mixture was stirred for 6 hours at 100° C. When the reaction was completed, the reaction product was quenched by adding water and water in the reaction product was removed. Then, the reaction product was filtered under reduced pressure. An organic layer was dried over $MgSO_4$ and concentrated to obtain 45.26 g (yield: 88%) of the product.

Synthesis of Core 2-7

Sub 1-7 (45.26 g, 114.8 mmol), Core 1-1 (33.73 g, 149.2 mmol), $Pd_2(PPh_3)_4$ (3.98 g, 3.4 mmol) and $K_2CO_3$ (47.60 g, 344.4 mmol) were placed in a round bottom flask and toluene (570 mL) and $H_2O$ (250 mL) were added thereto. After raising the temperature of the mixture to 80° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 43.10 g (yield: 82%) of the product.

(6) Synthesis Example of Core 2-8

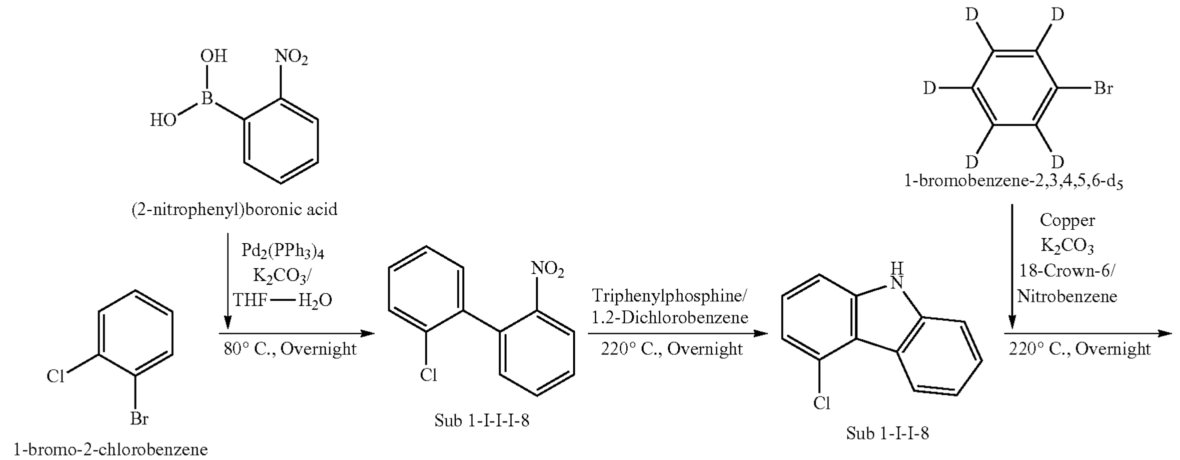

(2-nitrophenyl)boronic acid
1-bromo-2-chlorobenzene
Sub 1-I-I-I-8
Sub 1-I-I-8
1-bromobenzene-2,3,4,5,6-$d_5$ -continued

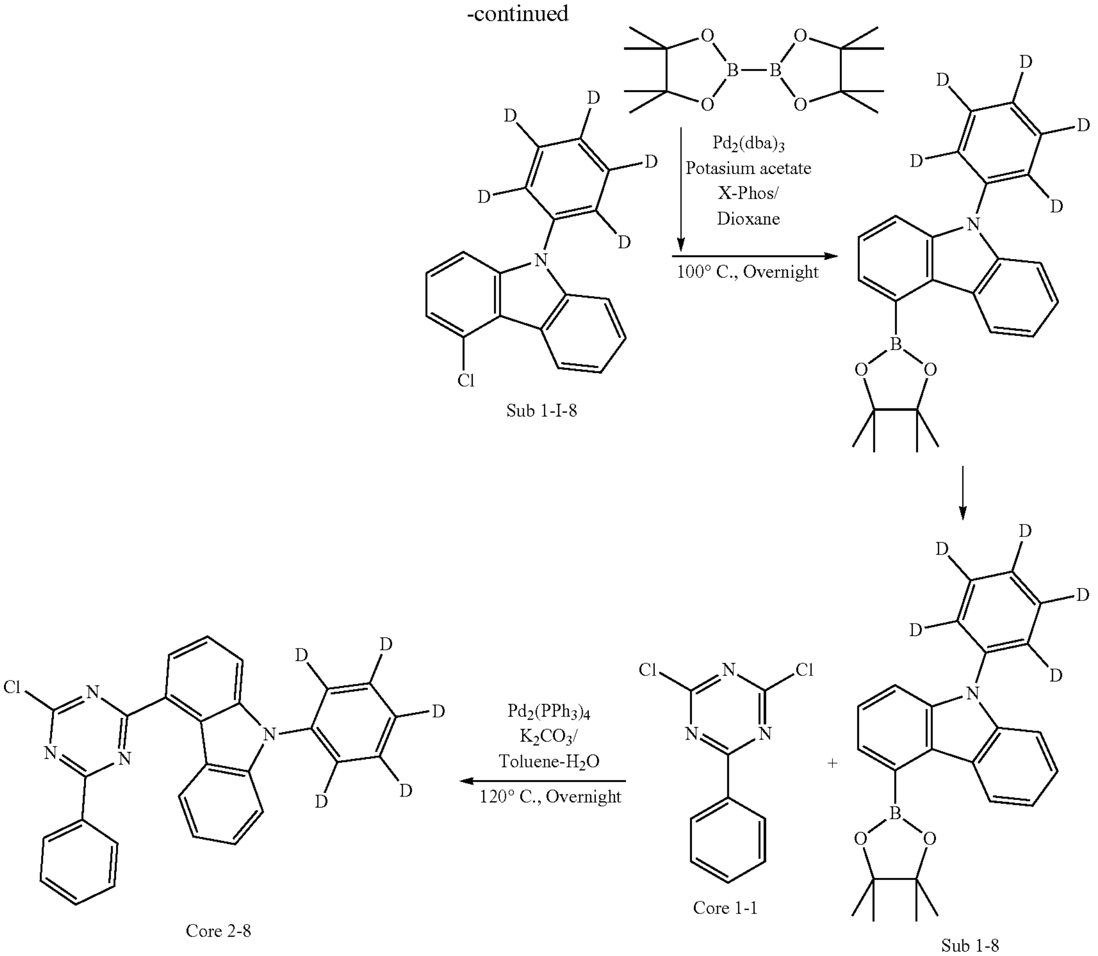

Sub 1-I-8

Sub 1-8

Core 1-1

Core 2-8

Synthesis of Sub 1-I-I-I-8

1-bromo-2-chlorobenzene (100.0 g, 522.3 mmol), (2-nitrophenyl)boronic acid (87.19 g, 522.3 mmol), $Pd_2(PPh_3)_4$ (18.11 g, 15.7 mmol) and $K_2CO_3$ (216.57 g, 1,567.0 mmol) were placed in a round bottom flask and tetrahydrofuran (2,500 mL) and $H_2O$ (1,250 mL) were added thereto. After raising the temperature of the mixture to 80° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 98.85 g (yield: 81%) of the product.

Synthesis of Sub 1-I-I-8

Sub 1-I-I-I-8 (98.85 g, 423.1 mmol), triphenylphosphine (332.90 g, 1,269.2 mmol) were placed in a round bottom flask and 1,2-dichlorobenzene (2,000 mL) was added thereto. After raising the temperature of the mixture to 220° C., the mixture was stirred for 16 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 72.52 g (yield: 85%) of the product.

Synthesis of Sub 1-I-8

Sub 1-I-I-8 (72.52 g, 359.6 mmol), 1-bromobenzene-2,3,4,5,6-$d_5$ (291.37 g, 1,798.2 mmol), Copper (2.29 g, 36.0 mmol), 18-Crown-6 (6.48 g, 18.0 mmol) and $K_2CO_3$ (149.11 g, 1,078.9 mmol) were placed in a round bottom flask and nitrobenzene (1,500 mL) was added thereto. After raising the temperature of the mixture to 220° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 85.43 g (yield: 84%) of the product.

Synthesis of Sub 1-8

Sub 1-I-8 (85.43 g, 302.1 mmol), bis(pinacolato)diboron (115.08 g, 453.2 mmol), $Pd_2(dba)_3$ (13.83 g, 15.1 mmol), potassium acetate (88.95 g, 906.3 mmol) and X-phos (14.40 g, 30.2 mmol) were placed in a round bottom flask and dioxane (1,500 mL) was added thereto. The mixture was stirred for 6 hours at 100° C. When the reaction was completed, the reaction product was quenched by adding water and then water in the reaction product was removed. Then, the reaction product was filtered under reduced pressure. An organic layer was over $MgSO_4$ and concentrated to obtain 102.90 g (yield: 91%) of the product.

Synthesis of Core 2-8

Sub 1-8 (102.90 g, 274.9 mmol), Core 1-1 (80.79 g, 357.4 mmol), $Pd_2(PPh_3)_4$ (9.53 g, 8.2 mmol) and $K_2CO_3$ (113.99 g, 824.7 mmol) were placed in a round bottom flask and toluene (1,300 mL) and $H_2O$ (600 mL) were added thereto. After raising the temperature of the mixture to 120° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 92.70 g (yield: 77%) of the product.

Compounds belonging to Core 2 may be the following compounds, but is not limited thereto, and Table 1 shows the FD-MS value of Compounds belonging to Core 2.

Core 2-1

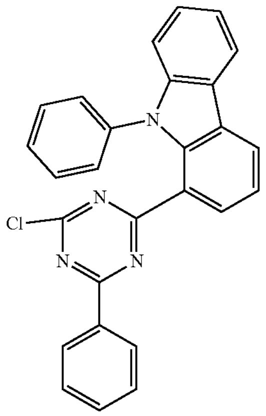

-continued

Core 2-2

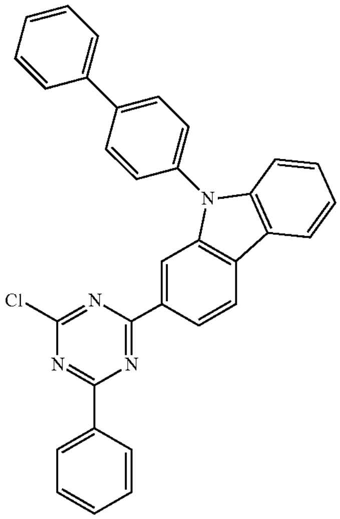

Core 2-3

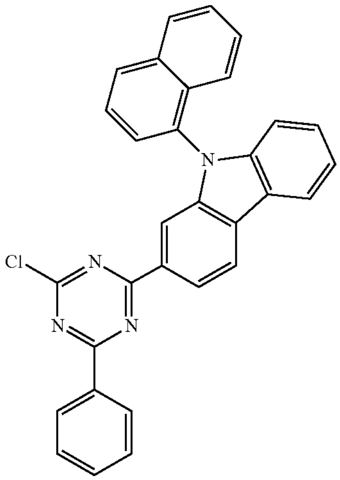

Core 2-4

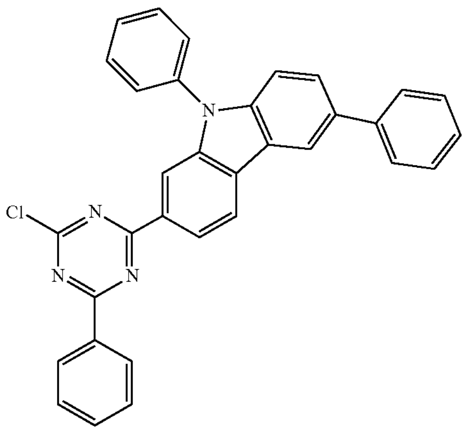

-continued
Core 2-5
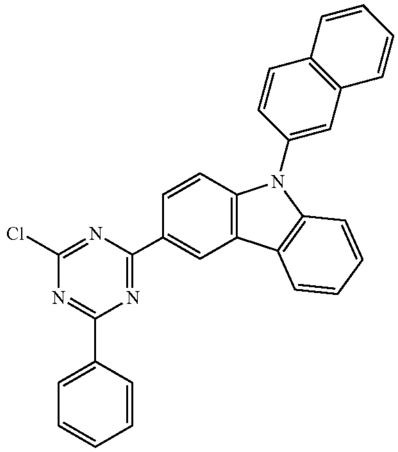
Core 2-6
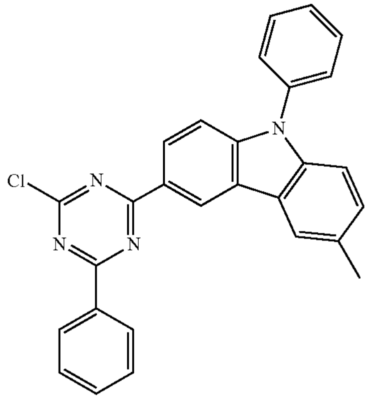
Core 2-7
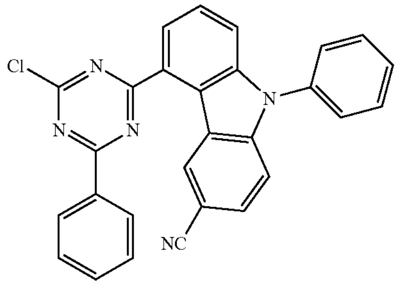
Core 2-8
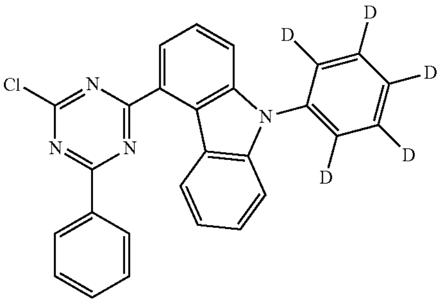
-continued
Core 2-9
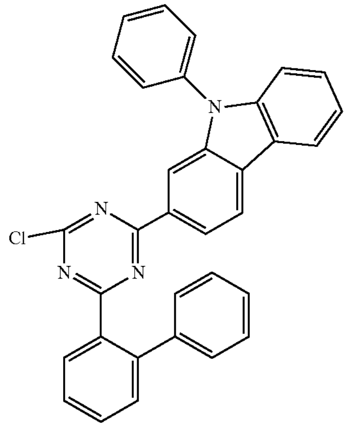
Core 2-10
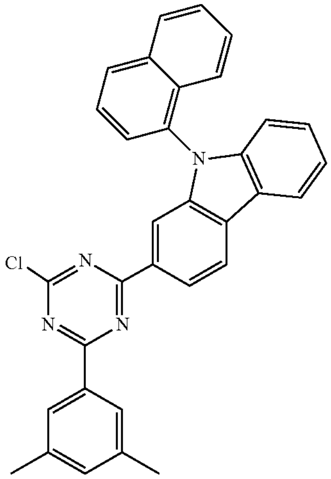
Core 2-11
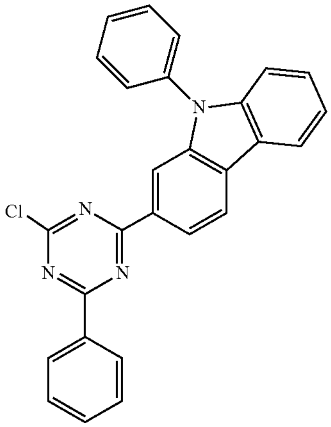

-continued
Core 2-12
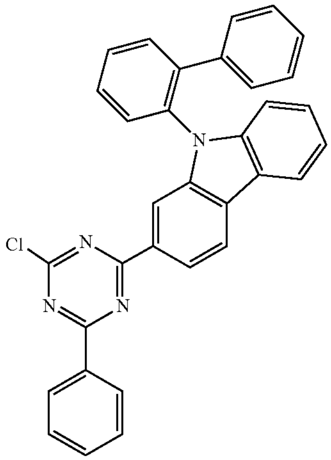
Core 2-13
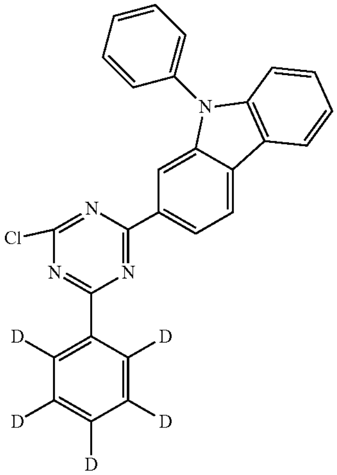
Core 2-14
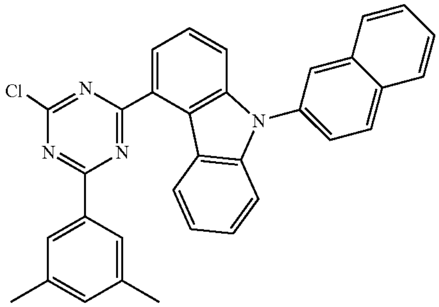
-continued
Core 2-15
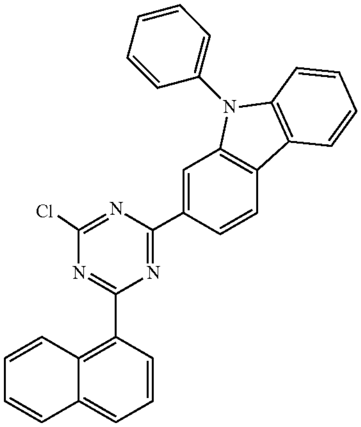
Core 2-16
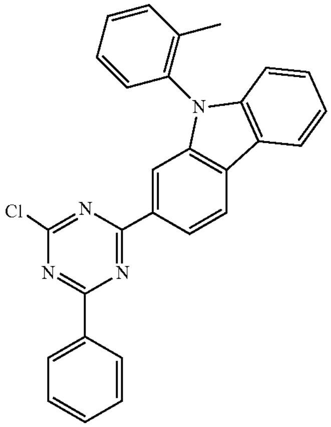
Core 2-17
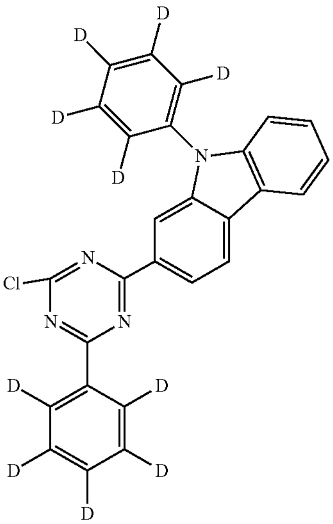

-continued
Core 2-18
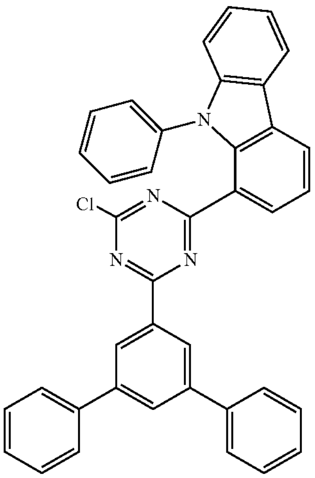
Core 2-19
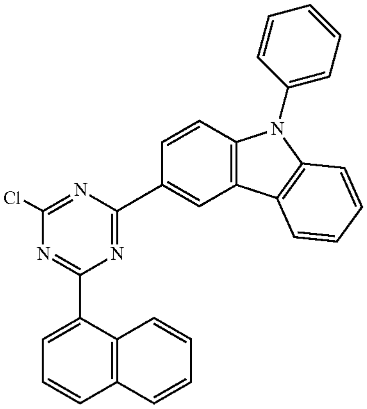
Core 2-20
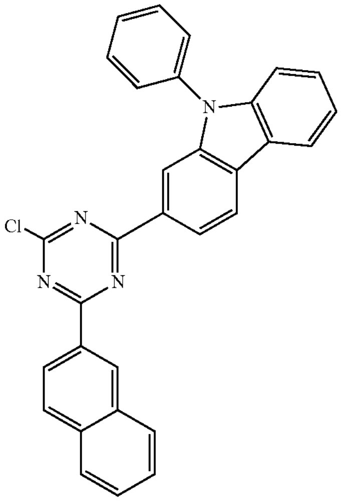
-continued
Core 2-21
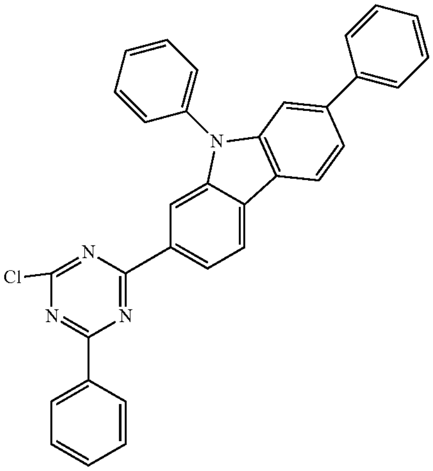
Core 2-22
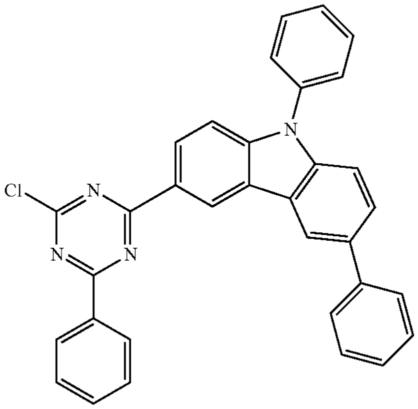
Core 2-23
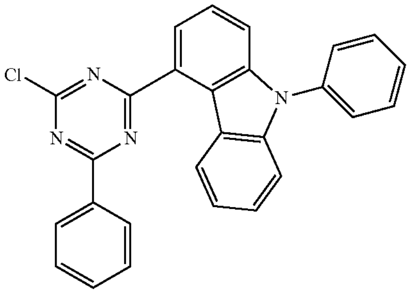
Core 2-24
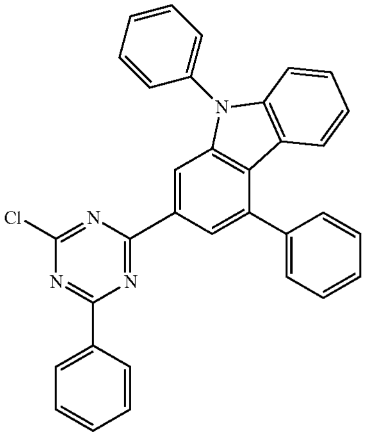

-continued
Core 2-25
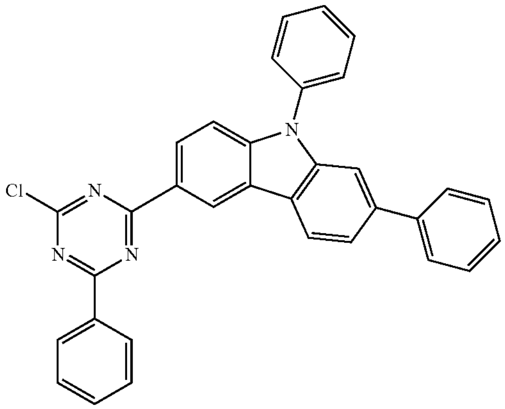
Core 2-26
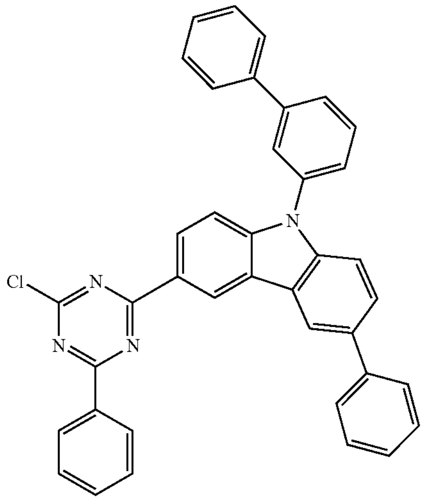
Core 2-27
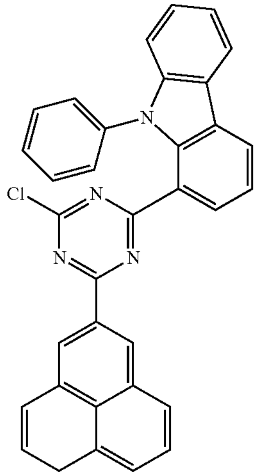
-continued
Core 2-28
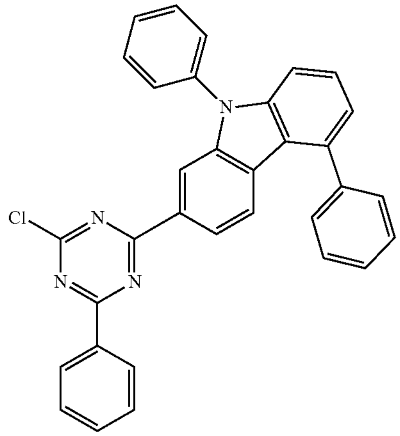
Core 2-29
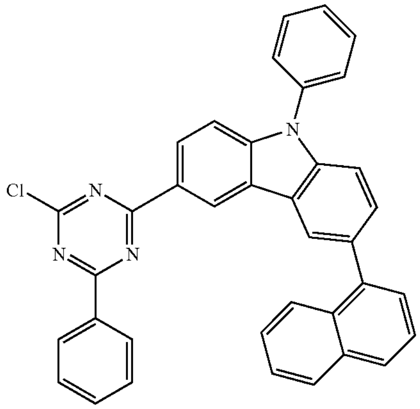
Core 2-30
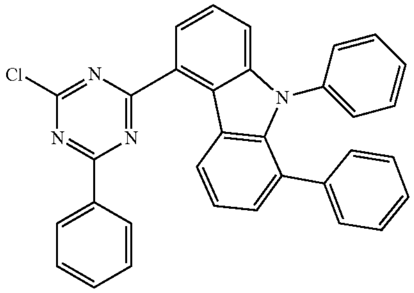
Core 2-31
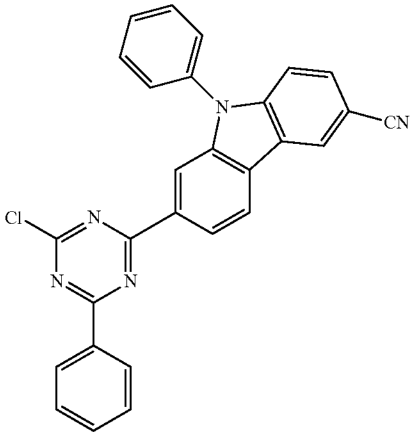

-continued
Core 2-32
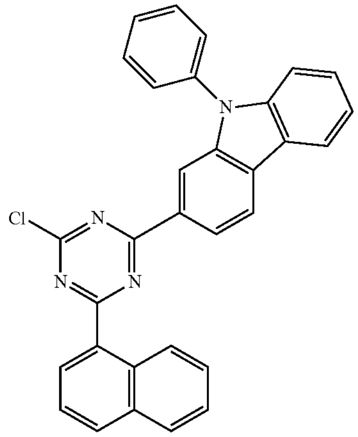
Core 2-33
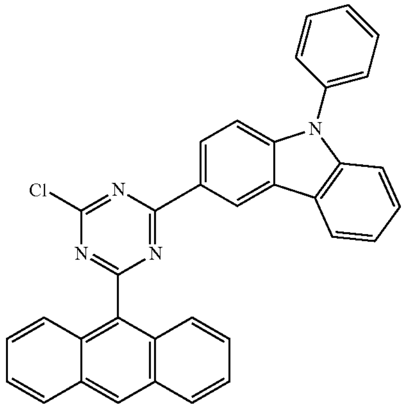
Core 2-34
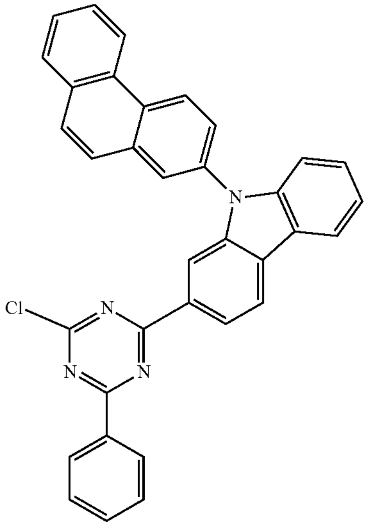
-continued
Core 2-35
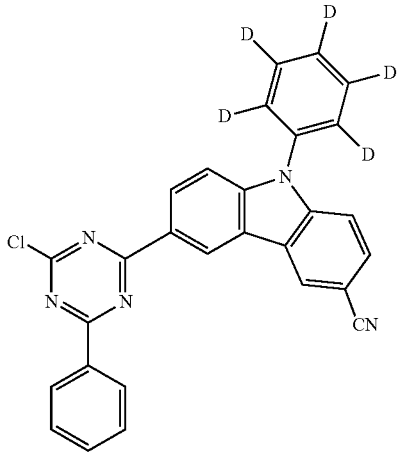
Core 2-36
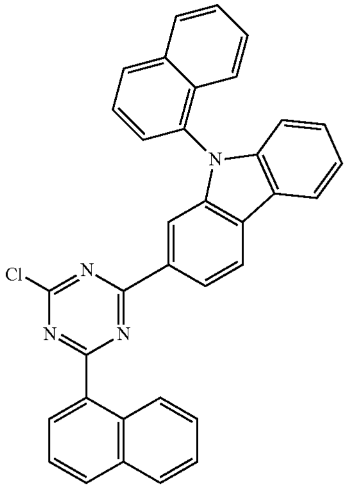
TABLE 1
| compound | FD-MS | compound | FD-MS |
|---|---|---|---|
| Core 2-1 | m/z = 432.11 ($C_{27}H_{17}ClN_4$ = 432.91) | Core 2-2 | m/z = 508.15 ($C_{33}H_{21}ClN_4$ = 509.01) |
| Core 2-3 | m/z = 482.13 ($C_{31}H_{19}ClN_4$ = 482.97) | Core 2-4 | m/z = 508.15 ($C_{33}H_{21}ClN_4$ = 509.01) |
| Core 2-5 | m/z = 482.13 ($C_{31}H_{19}ClN_4$ = 482.97) | Core 2-6 | m/z = 446.13 ($C_{28}H_{19}ClN_4$ = 446.94) |
| Core 2-7 | m/z = 457.11 ($C_{28}H_{16}ClN_5$ = 457.92) | Core 2-8 | m/z = 437.15 ($C_{27}H_{12}D_5ClN_4$ = 437.94) |
| Core 2-9 | m/z = 508.15 ($C_{33}H_{21}ClN_4$ = 509.01) | Core 2-10 | m/z = 510.16 ($C_{33}H_{23}ClN_4$ = 511.03) |
| Core 2-11 | m/z = 432.11 ($C_{27}H_{17}ClN_4$ = 432.91) | Core 2-12 | m/z = 508.15 ($C_{3}3H_{21}ClN_4$ = 509.01) |
| Core 2-13 | m/z = 437.15 ($C_{27}H_{12}D_5ClN_4$ = 437.94) | Core 2-14 | m/z = 510.16 ($C_{33}H_{23}ClN_4$ = 511.03) |

TABLE 1-continued

| compound | FD-MS | compound | FD-MS |
|---|---|---|---|
| Core 2-15 | m/z = 482.13 ($C_{31}H_{19}ClN_4$ = 482.97) | Core 2-16 | m/z = 446.13 ($C_{28}H_{19}ClN_4$ = 446.94) |
| Core 2-17 | m/z = 442.18 ($C_{27}H_7D_{10}ClN_4$ = 442.97) | Core 2-18 | m/z = 584.18 ($C_{39}H_{25}ClN_4$ = 585.11) |
| Core 2-19 | m/z = 482.13 ($C_{31}H_{19}ClN_4$ = 482.97) | Core 2-20 | m/z = 482.13 ($C_{31}H_{19}ClN_4$ = 482.97) |
| Core 2-21 | m/z = 508.15 ($C_{33}H_{21}ClN_4$ = 509.01) | Core 2-22 | m/z = 482.13 ($C_{31}H_{19}ClN_4$ = 482.97) |
| Core 2-23 | m/z = 432.11 ($C_{27}H_{17}ClN_4$ = 432.91) | Core 2-24 | m/z = 508.15 ($C_{33}H_{21}ClN_4$ = 509.01) |
| Core 2-25 | m/z = 508.15 ($C_{33}H_{21}ClN_4$ = 509.01) | Core 2-26 | m/z = 584.18 ($C_{39}H_{25}ClN_4$ = 585.11) |
| Core 2-27 | m/z = 520.15 ($C_{34}H_{21}ClN_4$ = 521.02) | Core 2-28 | m/z = 508.15 ($C_{33}H_{21}ClN_4$ = 509.01) |
| Core 2-29 | m/z = 558.16 ($C_{37}H_{23}ClN_4$ = 559.07) | Core 2-30 | m/z = 508.15 ($C_{33}H_{21}ClN_4$ = 509.01) |
| Core 2-31 | m/z = 457.11 ($C_{28}H_{16}ClN_5$ = 457.92) | Core 2-32 | m/z = 482.13 ($C_{31}H_{18}ClN_4$ = 482.97) |
| Core 2-33 | m/z = 532.15 ($C_{35}H_{21}ClN_5$ = 533.03) | Core 2-34 | m/z = 532.15 ($C_{35}H_{21}ClN_4$ = 533.03) |
| Core 2-35 | m/z = 462.14 ($C_{28}H_{11}D_5ClN_5$ = 462.95) | Core 2-36 | m/z = 532.15($C_{35}H_{21}ClN_4$ = 533.03) |

II. Synthesis of Sub 2

Sub 2 of Scheme 1 and 2 can be synthesized by the reaction routes of Reaction Schemes 11 to 15, but there is no limitation thereto.

Synthesis examples of specific compounds belonging to Sub 2 are as follows.

1. Synthesis Example of Sub 2-2

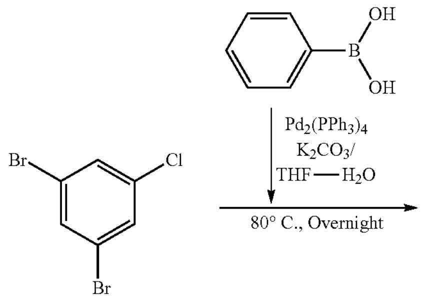

1,3-dibromo-5-chlorobenzene

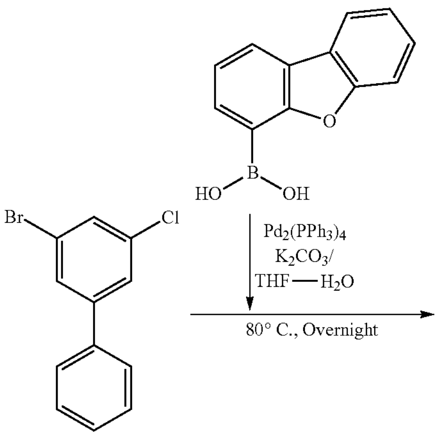

Sub 2-1-2

-continued

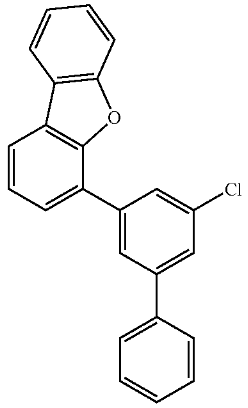

Sub 2-2

(1) Synthesis of Sub 2-1-2

Phenyl boronic acid (100 g, 599.1 mmol), $Pd_2(PPh_3)_4$ (20.77 g, 18.0 mmol), and $K_2CO_3$ (248.39 g, 1,797.2 mmol) were added to 1,3-dibromo-5-chlorobenzene (323.91 g, 1,198.1 mmol) being a starting material and tetrahydrofuran (3,000 mL) and $H_2O$ (1,500 mL) were added thereto. After raising the temperature of the mixture to 80° C., the mixture was stirred for 6 hours in a dissolved state. Upon completion of the reaction, the reaction product was concentrated under reduced pressure and quenched with water. The solid reaction product was obtained by filtering, and water was removed from the reaction product escaped as filtrate and filtered under reduced pressure. Thereafter, it was dried over $MgSO_4$ and concentrated. Impurities were removed from the concentrate by applying a silica gel column and recrystallization to obtain 110.59 g (yield: 69%) of the product.

(2) Synthesis of Sub 2-2

Tetrahydrofuran (1,300 mL) and $H_2O$ (650 mL) were added to the mixture of dibenzo[b,d]furan-4-ylboronic acid (58.42 g, 275.6 mmol), $Pd_2(PPh_3)_4$ (9.55 g, 8.3 mmol) and $K_2CO_3$ (114.25 g, 826.7 mmol). After raising the temperature of the mixture to 80° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 79.64 g (yield: 81%) of the product.

2. Synthesis Example of Sub 2-7

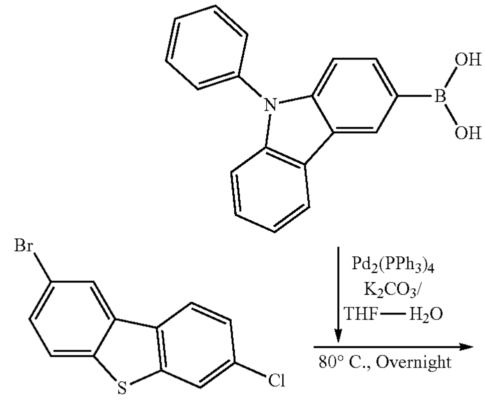

2-bromo-7-chlorodibenzo[b,d]thiophene

-continued

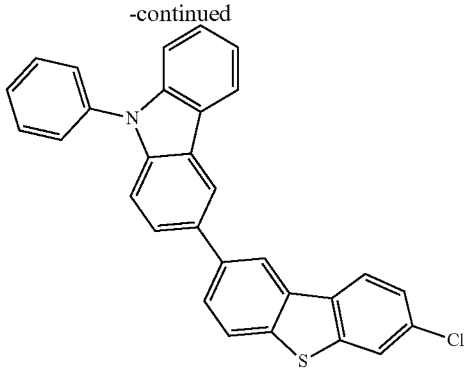

Sub 2-7

(9-phenyl-9H-carbazol-3-yl)boronic acid (106.13 g, 369.6 mmol), $Pd_2(PPh_3)_4$ (11.65 g, 10.1 mmol) and $K_2CO_3$ (139.33 g, 1,008.1 mmol) were added to 2-bromo-7-chlorodibenzo[b,d]thiophene (100.0 g, 336.0 mmol) and tetrahydrofuran (1,600 mL) and $H_2O$ (800 mL) thereto. After raising the temperature of the mixture to 80° C., the mixture was stirred for 6 hours in a dissolved state. When the reaction was completed, the reaction product was concentrated under reduced pressure and quenched by adding water. Then, the solid reaction product was obtained by filtering, and water was removed from the reaction product escaped as filtrate and then the reaction product was filtered under reduced pressure. Thereafter, it was dried over $MgSO_4$ and concentrated. Impurities were removed from the concentrate by applying a silica gel column and recrystallization to obtain 119.02 g (yield: 77%) of the product.

3. Synthesis Example of Sub 2-8

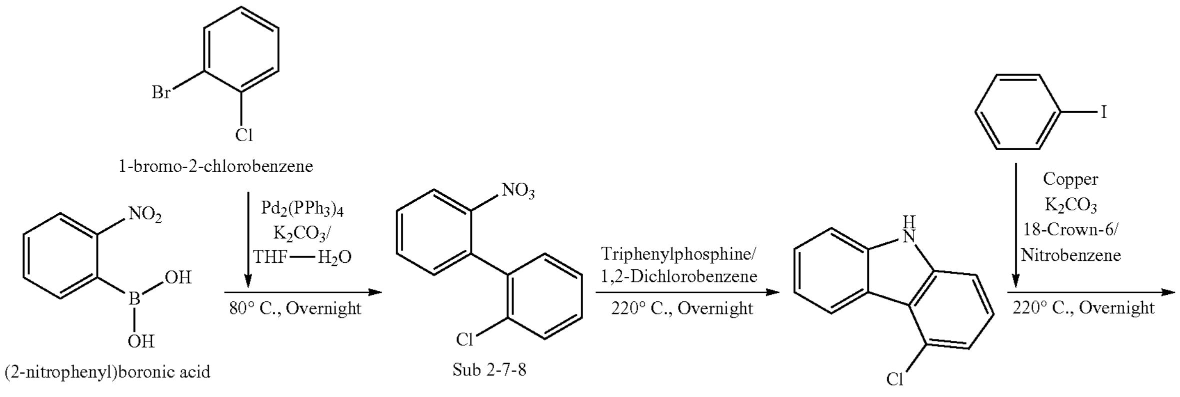

1-bromo-2-chlorobenzene (2-nitrophenyl)boronic acid

Sub 2-7-8

Sub 2-6-8

-continued

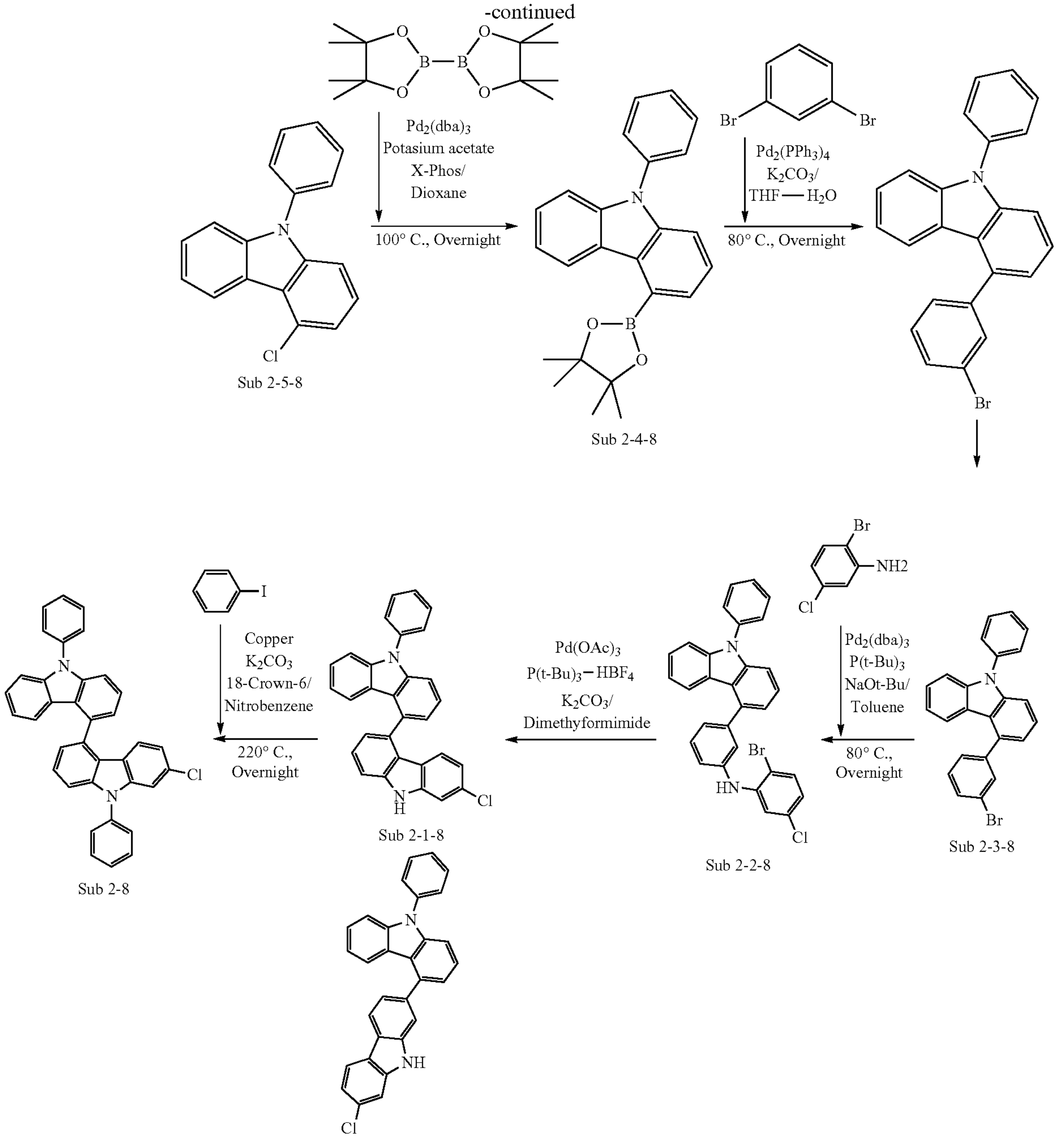

(1) Synthesis of Sub 2-7-8

(2-nitrophenyl)boronic acid (100.0 g, 599.1 mmol), 1-bromo-3-chlorobenzene (172.03 g, 898.6 mmol), $Pd_2(PPh_3)_4$ (20.77 g, 18.0 mmol) and $K_2CO_3$ (248.39 g, 1,797.2 mmol) were placed into a round bottom flask and THF (3,000 mL) and $H_2O$ (1,500 mL) were added thereto. After raising the temperature of the mixture to 80° C., the mixture was stirred for 24 hours. When the reaction was completed, water in the reaction product was removed and the reaction product was filtered under reduced pressure. After that, the filtrate was dried over $MgSO_4$ and concentrated. Impurities were removed from the concentrate by applying a silica gel column and recrystallization to obtain 121.77 g (yield: 87%) of the product.

(2) Synthesis of Sub 2-6-8

Sub 2-7-8 (92.48 g, 458.6 mmol) and triphenylphosphine (410.09 g, 1,563.5 mmol) were placed into a round bottom flask and 1,2-dichlorobenzene (2,500 mL) was added thereto. After raising the temperature of the mixture to 80° C., the mixture was stirred for 24 hours. When the reaction was completed, the reaction product was concentrated under reduced pressure, quenched by adding toluene and water and water in the reaction product was removed. After that, the reaction product was filtered under reduced pressure, dried over $MgSO_4$ and concentrated. Impurities were removed from the concentrate by applying a silica gel column and recrystallization to obtain 92.48 g (yield: 88%) of the product.

(3) Synthesis of Sub 2-5-8

Sub 2-6-8 (92.48 g, 458.6 mmol), iodobenzene (467.81 g, 2,293.1 mmol), $K_2CO_3$ (190.16 g, 1,375.8 mmol), copper (2.91 g, 45.9 mmol) and 18-crown-6 (8.26 g, 22.9 mmol) were placed into a round bottom flask and nitrobenzene (2,300 mL) was added thereto. After raising the temperature of the mixture to 220° C., the mixture was stirred for 24 hours. When the reaction was completed, the reaction product was filtered by silica gel filter and quenched by adding water. Then, water in the reaction product was removed, and the reaction product was filtered under reduced pressure. After that, the filtrate was dried over $MgSO_4$ and concentrated. Impurities were removed from the concentrate by applying a silica gel column and recrystallization to obtain 108.94 g (yield: 84%) of the product.

(4) Synthesis of Sub 2-4-8

Sub 2-5-8 (108.94 g, 385.2 mmol), bis(pinacolato)diboron (146.74 g, 577.9 mmol), $Pd_2(dba)_3$ (17.64 g, 19.3 mmol), potassium acetate (113.42 g, 1,155.7 mmol) and X-phos (18.37 g, 38.5 mmol) were placed in a round bottom flask and dioxane (2,000 mL) was added thereto. Then, the mixture was stirred for 6 hours at 100° C. When the reaction was completed, the reaction product was quenched by adding water. After that, water in the reaction product was removed and the reaction product was filtered under reduced pressure. Then, an organic layer was dried over $MgSO_4$ and concentrated to obtain 115.36 g (yield: 80%) of the product.

(5) Synthesis of Sub 2-3-8

Sub 2-4-8 (102.90 g, 274.9 mmol), 1,3-dibromobenzene (84.31 g, 357.4 mmol), $Pd_2(PPh_3)_4$ (9.53 g, 8.2 mmol) and $K_2CO_3$ (113.99 g, 824.7 mmol) were placed in a round bottom flask and THF (1,300 mL) and $H_2O$ (650 mL) were added thereto. After raising the temperature of the mixture to 80° C., the mixture was stirred for 24 hours. When the reaction was completed, water in the reaction product was removed and the reaction product was filtered under reduced pressure. After that, the filtrate was dried over $MgSO_4$ and concentrated. Impurities were removed from the concentrate by applying a silica gel column and recrystallization to obtain 79.93 g (yield: 73%) of the product.

(6) Synthesis of Sub 2-2-8

Sub 2-3-8 (79.93 g, 200.7 mmol), 2-bromo-5-chloroaniline (53.86 g, 260.9 mmol), $Pd_2(dba)_3$ (5.51 g, 6.0 mmol), NaOt-Bu (57.86 g, 602.0 mmol) and $P(t\text{-}Bu)_3$ (3.25 g, 16.1 mmol) were placed into a round bottom flask and toluene (1,000 mL) was added thereto. After raising the temperature of the mixture to 80° C., the mixture was stirred for 24 hours. When the reaction was completed, water in the reaction product was removed and the reaction product was filtered under reduced pressure. After that, the filtrate was dried over $MgSO_4$ and concentrated. Impurities were removed from the concentrate by applying a silica gel column and recrystallization to obtain 88.31 g (yield: 84%) of the product.

(7) Synthesis of Sub 2-1-8

Sub 2-2-8 (88.31 g, 168.6 mmol), $Pd(OAc)_2$ (0.76 g, 3.4 mmol), $K_2CO_3$ (69.90 g, 505.7 mmol) and $P(t\text{-}Bu)_3\text{-}HBF_4$ (4.89 g, 16.9 mmol) were placed into a round bottom flask and dimethylformimide (800 mL) was added thereto. After raising the temperature of the mixture to 150° C., the mixture was stirred for 5 hours. When the reaction was completed, water in the reaction product was removed and the reaction product was filtered under reduced pressure. After that, the filtrate was dried over $MgSO_4$ and concentrated. Impurities were removed from the concentrate by applying a silica gel column and recrystallization to obtain 25.39 g (yield: 34%) of the product.

(8) Synthesis of Sub 2-8

Sub 2-1-8 (25.39 g, 48.5 mmol), iodobenzene (12.85 g, 63.0 mmol), $K_2CO_3$ (20.10 g, 145.4 mmol), copper (0.31 g, 4.8 mmol) and 18-crown-6 (0.87 g, 2.4 mmol) were placed into a round bottom flask and nitrobenzene (250 mL) was added thereto. After raising the temperature of the mixture to 220° C., the mixture was stirred for 24 hours. When the reaction was completed, the reaction product was filtered by silica gel filter and quenched by adding water. After that, water in the reaction product was removed and the reaction product was filtered under reduced pressure. The filtrate was dried over $MgSO_4$ and concentrated. Impurities were removed from the concentrate by applying a silica gel column and recrystallization to obtain 22.64 g (yield: 90%) of the product.

4. Synthesis Example of Sub 2-16

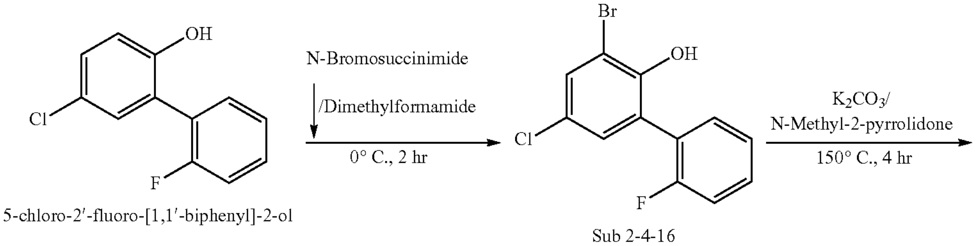

5-chloro-2′-fluoro-[1,1′-biphenyl]-2-ol

Sub 2-4-16

-continued

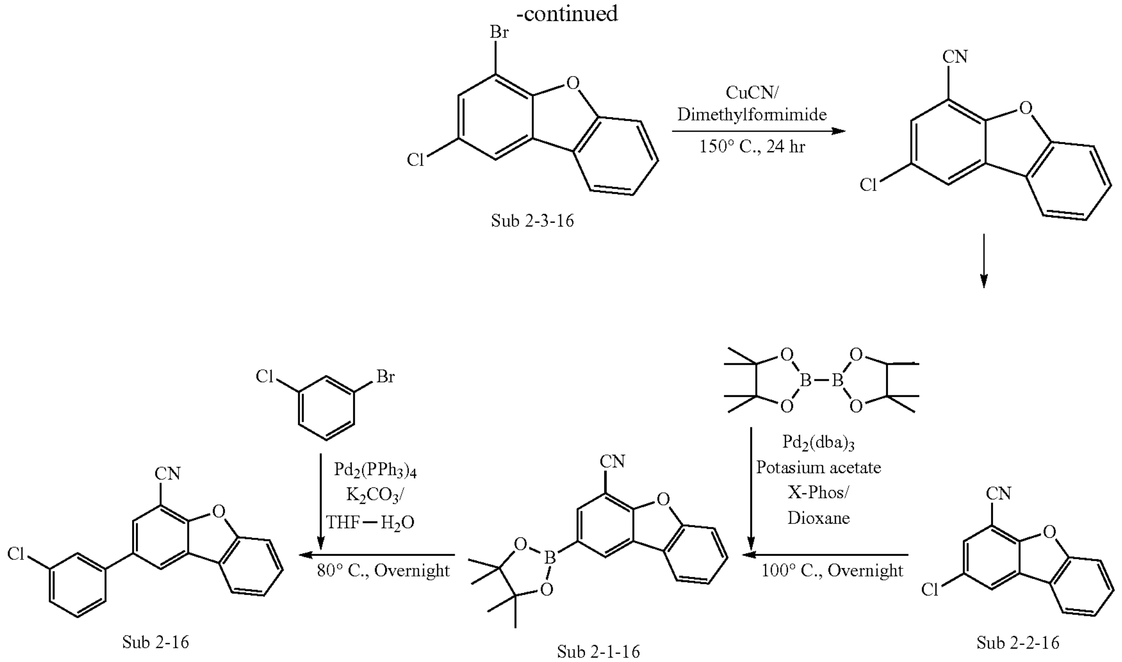

Sub 2-3-16

Sub 2-16

Sub 2-1-16

Sub 2-2-16

(1) Synthesis of Sub 2-4-16

5-chloro-2'-fluoro-[1,1'-biphenyl]-2-ol (100.0 g, 449.2 mmol), N-bromosuccinimide (87.94 g, 494.1 mmol) and methylene chloride (2,200 mL) were placed in a round bottom flask. After raising the temperature of the mixture to 40° C., the mixture was stirred for 24 hours in dissolved state. When the reaction was completed, the reaction product was concentrated under reduced pressure and quenched by adding water. After that, water in the reaction product was removed and the reaction product was filtered under reduced pressure. The filtrate was dried over $MgSO_4$ and concentrated. Then, impurities were removed from the concentrate by applying a silica gel column and recrystallization to obtain 119.23 g (yield: 88%) of the product.

(2) Synthesis of Sub 2-3-16

Sub 2-4-16 (119.23 g, 395.3 mmol) and $K_2CO_3$ (163.89 g, 1185.3 mmol) were placed in a round bottom flask and N-Methyl-2-pyrrolidone (1,900 mL) was added thereto. After raising the temperature of the mixture to 150° C., the mixture was stirred for 5 hours in dissolved state. When the reaction was completed, the reaction product was concentrated under reduced pressure and quenched by adding water. After that, water in the reaction product was removed and the reaction product was filtered under reduced pressure. The filtrate was dried over $MgSO_4$ and concentrated. Then, impurities were removed from the concentrate by applying a silica gel column and recrystallization to obtain 44.51 g (yield: 40%) of the product.

(3) Synthesis of Sub 2-2-16

Sub 2-3-16 (44.51 g, 158.1 mmol) and CuCN (46.46 g, 205.5 mmol) were placed into a round bottom flask and dimethylformimide (790 mL) was added thereto. After raising the temperature of the mixture to 150° C., the mixture was stirred for 5 hours in dissolved state. When the reaction was completed, the reaction product was filtered by silica gel filter and quenched by adding water. Then, water in the reaction product was removed, and the reaction product was filtered under reduced pressure. After that, the filtrate was dried over $MgSO_4$ and concentrated. Impurities were removed from the concentrate by applying a silica gel column and recrystallization to obtain 34.19 g (yield: 95%) of the product.

(4) Synthesis of Sub 2-1-16

Sub 2-2-16 (34.19 g, 150.2 mmol), bis(pinacolato)diboron (57.21 g, 225.3 mmol), $Pd_2(dba)_3$ (6.88 g, 7.5 mmol), potassium acetate (44.22 g, 450.6 mmol) and X-phos (7.16 g, 15.0 mmol) were placed in a round bottom flask and dioxane (750 mL) was added thereto. Then, the mixture was stirred for 6 hours at 100° C. When the reaction was completed, the reaction product was quenched by adding water and water in the reaction product was removed. After that, the reaction product was filtered under reduced pressure. Then, the organic layer was dried over $MgSO_4$ and concentrated to obtain 40.74 g (yield: 85%) of the product.

(5) Synthesis of Sub 2-16

Sub 2-1-16 (40.74 g, 127.6 mmol), 1-bromo-3-chlorobenzene (36.66 g, 191.5 mmol), $Pd_2(PPh_3)_4$ (4.42 g, 3.8 mmol) and $K_2CO_3$ (52.92 g, 382.9 mmol) were placed into a round bottom flask and THF (600 mL) and $H_2O$ (300 mL) were added thereto. After raising the temperature of the mixture to 80° C., the mixture was stirred for 24 hours in dissolved state. When the reaction was completed, water in the reaction product was removed and the reaction product was filtered under reduced pressure. After that, the filtrate was dried over $MgSO_4$ and concentrated. Impurities were removed from the concentrate by applying a silica gel column and recrystallization to obtain 34.12 g (yield: 88%) of the product.

5. Synthesis Example of Sub 2-27

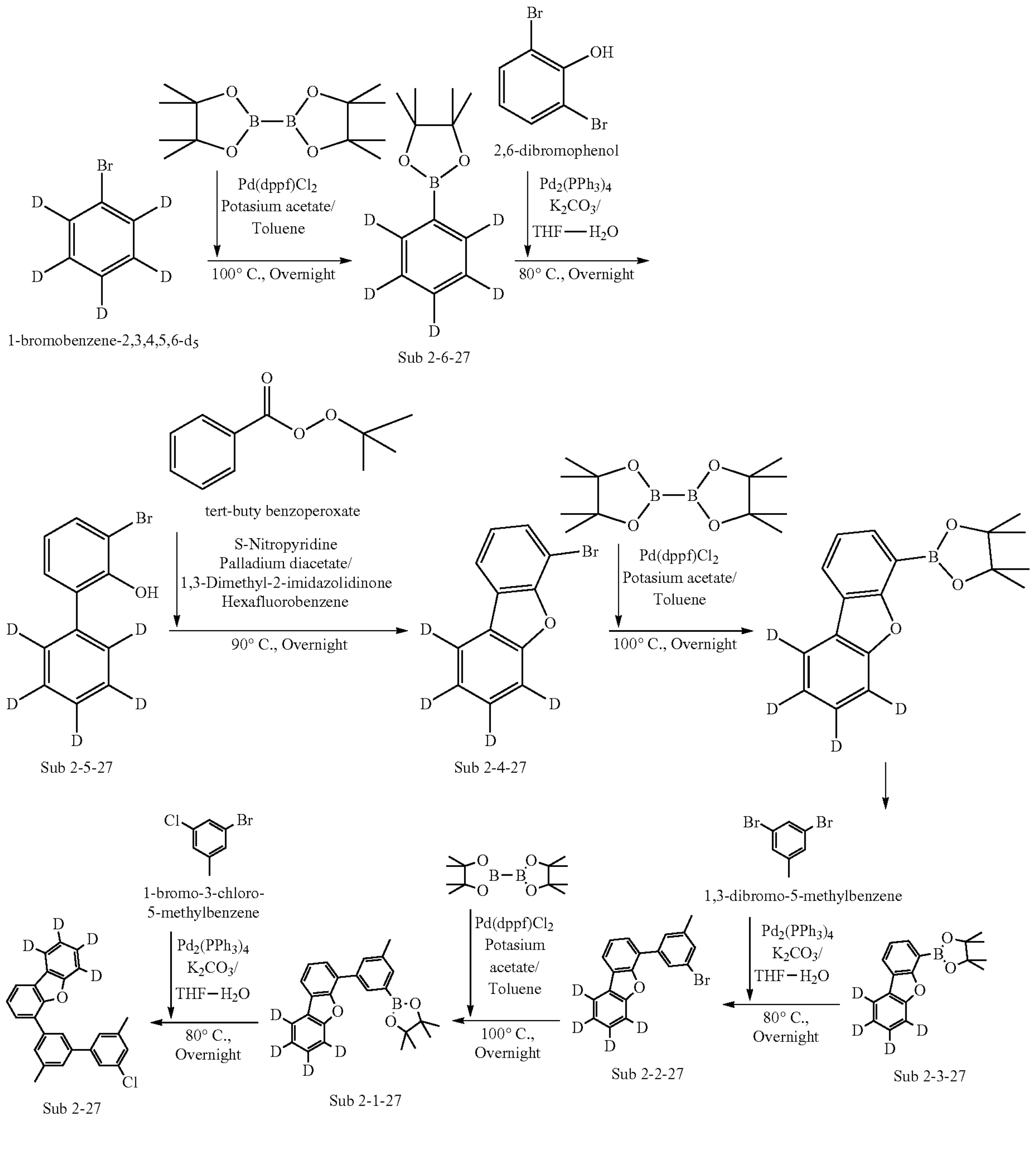

(1) Synthesis of Sub 2-6-27

1-bromonezene-2,3,4,5,6-$d_5$ (150 g, 925.7 mmol), bis(pinacolato)diboron (352.61 g, 1,388.5 mmol), Pd(dppf)$Cl_2$ (22.68 g, 27.8 mmol) and potassium acetate (272.54 g, 2,777.1 mmol) were placed in a round bottom flask and toluene (4,500 mL) was added thereto. Then, the mixture was stirred for 6 hours at 100° C. When the reaction was completed, the reaction product was quenched by adding water and water in the reaction product was removed. After that, the reaction product was filtered under reduced pressure. Then, an organic layer was dried over $MgSO_4$ and concentrated to obtain 176.15 g (yield: 91%) of the product.

(2) Synthesis of Sub 2-5-27

Sub 2-6-27 (176.15 g, 842.4 mmol), 2,6-dibromophnol (318.31 g, 1,263.6 mmol), $Pd_2(PPh_3)_4$ (29.20 g, 25.3 mmol) and $K_2CO_3$ (349.28 g, 2,527.1 mmol) were placed in a round bottom flask and THF (4,000 mL) and $H_2O$ (2,000 mL) were added thereto. After raising the temperature of the mixture to 80□, the mixture was stirred for 24 hours. When the reaction was completed, water in the reaction product was removed and the reaction product was filtered under reduced pressure. The filtrate was dried over $MgSO_4$ and concentrated. Thereafter, impurities were removed from the concentrate by applying a silica gel column and recrystallization to obtain 152.0 g (yield: 71%) of the product.

(3) Synthesis of Sub 2-4-27

Sub 2-5-27 (152.0 g, 598.1 mmol), tert-butyl benzoperoxoate (232.34 g, 1,196.2 mmol), 3-nitropyridine(209.13 g, 897.1 mmol) and palladium diacetate (8.06 g, 35.9 mmol) were placed in a round bottom flask and 1,3-dimethyl-2-imidazolidinone (1,500 ml) and hexafluorobenzene (1,500 ml) were added thereto. When the reaction was completed, water in the reaction product was removed and the reaction product was filtered under reduced pressure. The filtrate was dried over $MgSO_4$ and concentrated. Thereafter, impurities were removed from the concentrate by applying a silica gel column and recrystallization to obtain 75.10 g (yield: 50%) of the product.

(4) Synthesis of Sub 2-3-27

Sub 2-4-27 (75.10 g, 299.1 mmol), bis(pinacolato)diboron (113.92 g, 448.6 mmol), $Pd(dppf)Cl_2$ (7.33 g, 9.0 mmol) and potassium acetate (88.05 g, 897.2 mmol) were placed in a round bottom flask and toluene (1,500 mL) was added thereto. Then, the mixture was stirred for 6 hours at 100° C. When the reaction was completed, the reaction product was quenched by adding water and water in the reaction product was removed. After that, the reaction product was filtered under reduced pressure. Then, an organic layer was dried over $MgSO_4$ and concentrated to obtain 79.36 g (yield: 89%) of the product.

(5) Synthesis of Sub 2-2-27

Sub 2-3-27 (79.36 g, 266.1 mmol), 1,3-dibromo-5-methylbenzene (101.38 g, 399.2 mmol), $Pd_2(PPh_3)_4$ (9.23 g, 8.0 mmol) and $K_2CO_3$ (110.35 g, 798.4 mmol) were placed in a round bottom flask and THF (1,300 mL) and $H_2O$ (650 mL) were added thereto. After raising the temperature of the mixture to 80□, the mixture was stirred for 24 hours. When the reaction was completed, water in the reaction product was removed and the reaction product was filtered under reduced pressure. After that, the filtrate was dried over $MgSO_4$ and concentrated. Thereafter, impurities were removed from the concentrate by applying a silica gel column and recrystallization to obtain 69.93 g (yield: 77%) of the product.

(6) Synthesis of Sub 2-1-27

Sub 2-2-27 (69.93 g, 204.9 mmol), bis(pinacolato)diboron (78.06 g, 307.4 mmol), $Pd(dppf)Cl_2$ (5.02 g, 6.1 mmol) and potassium acetate (60.34 g, 614.8 mmol) were placed in a round bottom flask and toluene (1,000 mL) was added thereto. Then, the mixture was stirred for 6 hours at 100° C. When the reaction was completed, the reaction product was quenched by adding water and water in the reaction product was removed. After that, the reaction product was filtered under reduced pressure. Then, an organic layer was dried over $MgSO_4$ and concentrated to obtain 55.70 g (yield: 70%) of the product.

(7) Synthesis of Sub 2-27

Sub 2-1-27 (55.70 g, 143.4 mmol), 1,3-dibromo-5-methylbenzene (44.21 g, 215.2 mmol), $Pd_2(PPh_3)_4$ (4.97 g, 4.3 mmol) and $K_2CO_3$ (59.48 g, 430.3 mmol) were placed in a round bottom flask and THF (700 mL) and $H_2O$ (350 mL) were added thereto. After raising the temperature of the mixture to 80□, the mixture was stirred for 24 hours. When the reaction was completed, water in the reaction product was removed and the reaction product was filtered under reduced pressure. After that, the filtrate was dried over $MgSO_4$ and concentrated. Thereafter, impurities were removed from the concentrate by applying a silica gel column and recrystallization to obtain 38.29 g (yield: 69%) of the product.

Compounds belonging to Sub 1 may be the following compounds, but is not limited thereto, and Table 2 shows the FD-MS value of the following compounds.

Sub 2-1

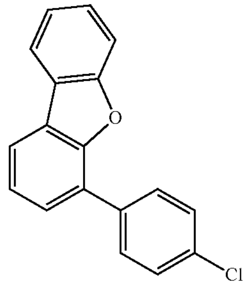

Sub 2-2

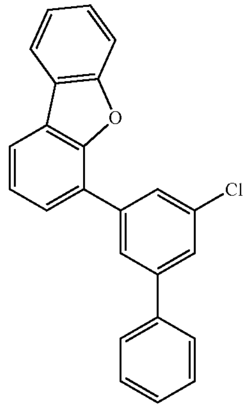

Sub 2-3

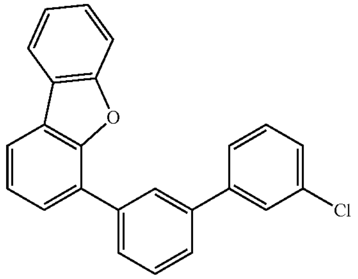

Sub 2-4
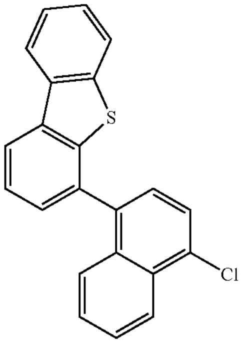
Sub 2-5
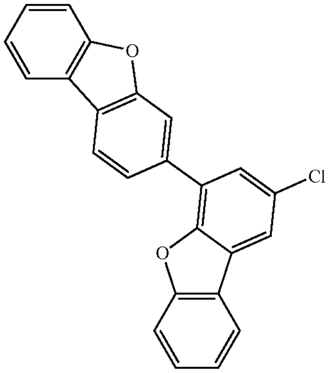
Sub 2-6
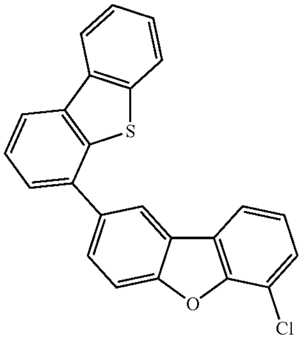
Sub 2-7
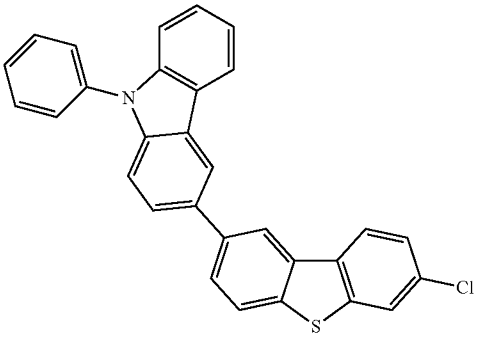
Sub 2-8
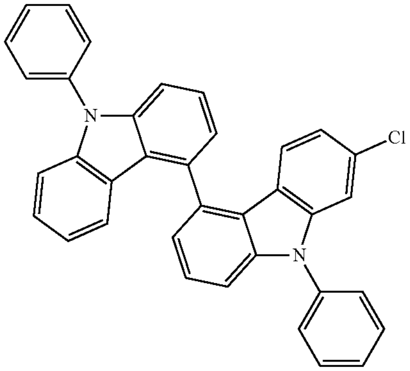
Sub 2-9
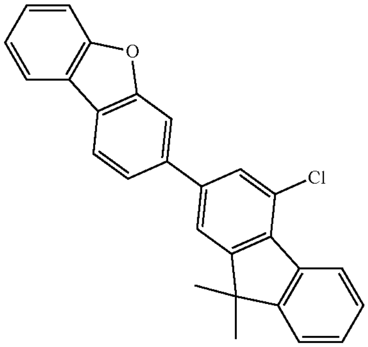
Sub 2-10
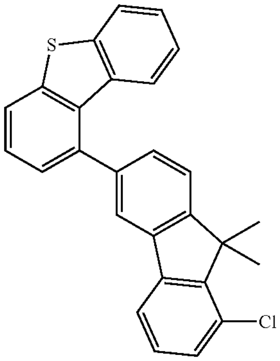
Sub 2-11
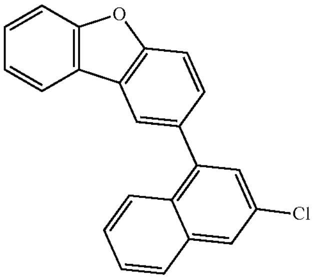

-continued
Sub 2-12
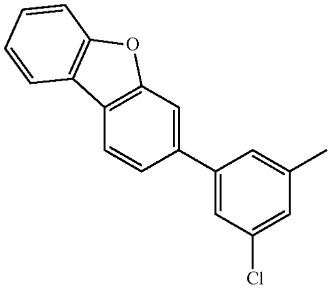
Sub 2-13
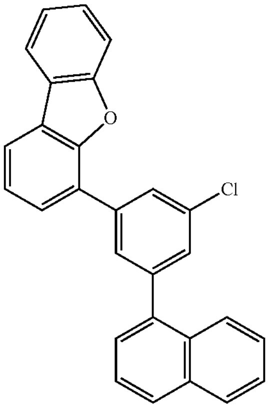
Sub 2-14
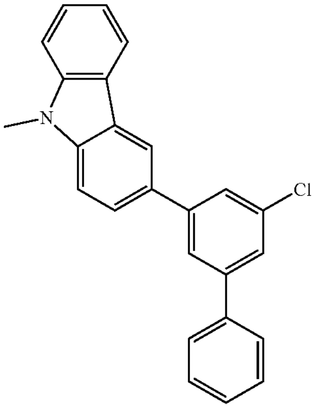
Sub 2-15
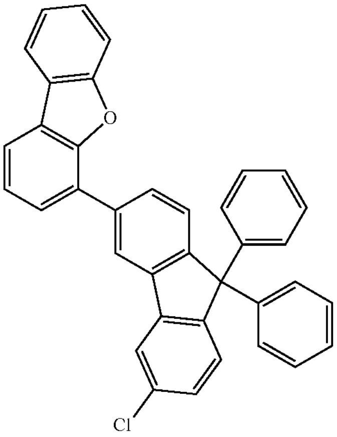
-continued
Sub 2-16
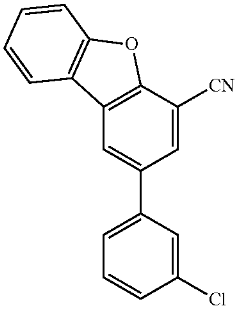
Sub 2-17
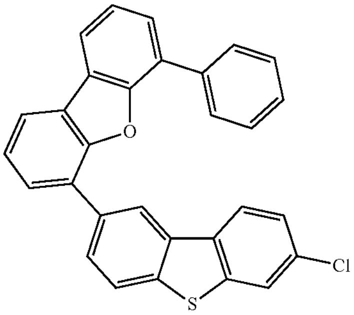
Sub 2-18
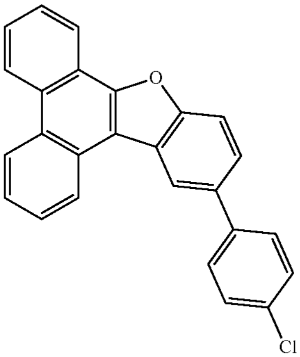
Sub 2-19
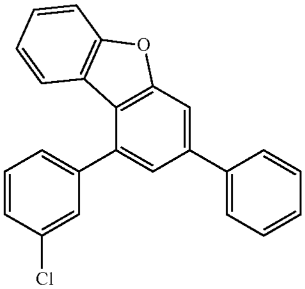
Sub 2-20
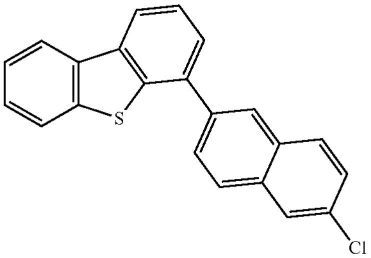

-continued
Sub 2-21
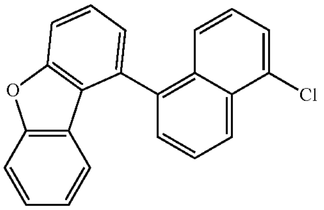
Sub 2-22
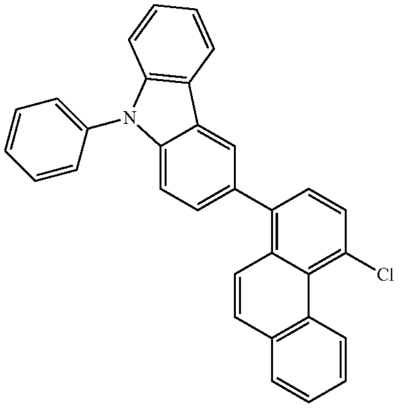
Sub 2-23
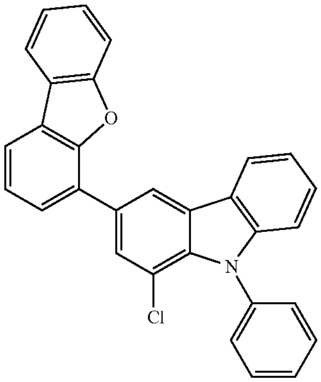
Sub 2-24
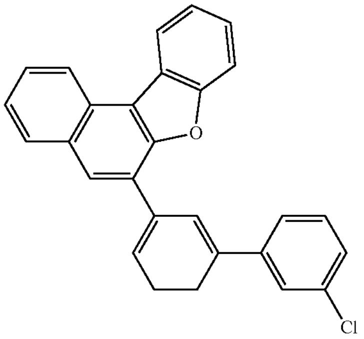
-continued
Sub 2-25
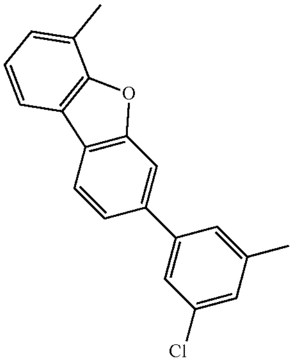
Sub 2-26
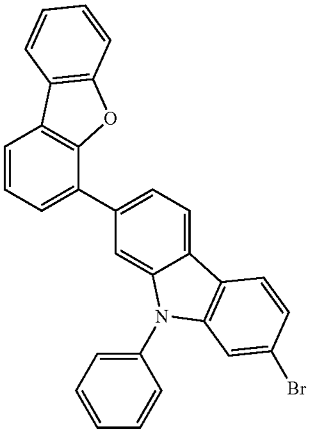
Sub 2-27
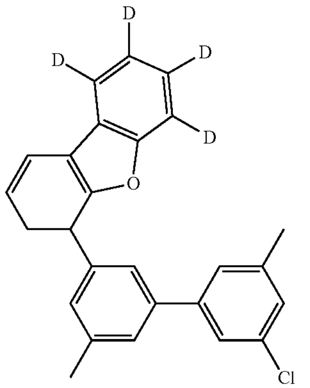
Sub 2-28
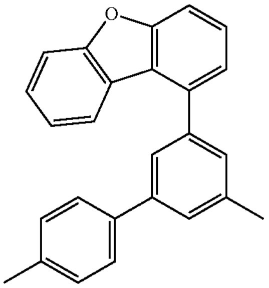

-continued
Sub 2-29
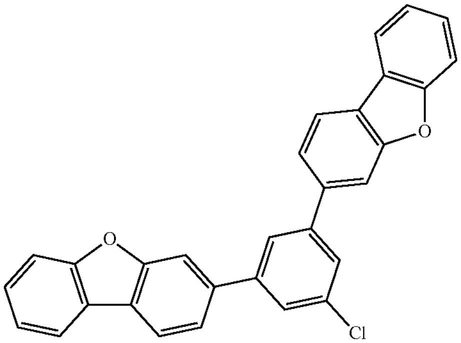
Sub 2-30
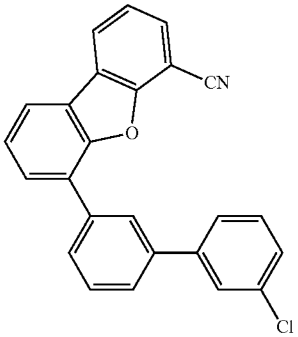
Sub 2-31
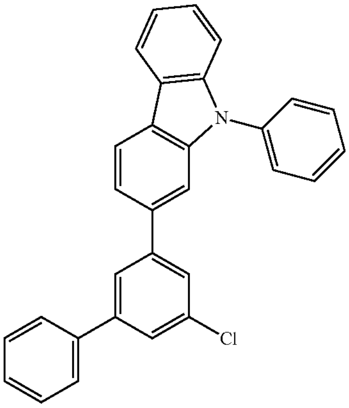
Sub 2-32
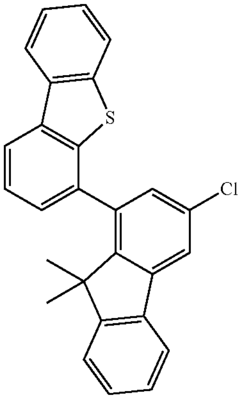
-continued
Sub 2-33
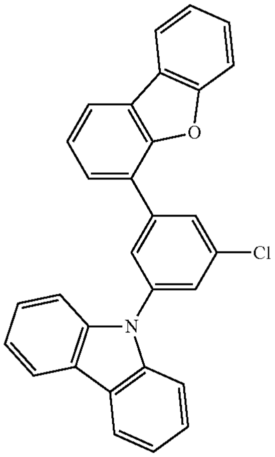
Sub 2-34
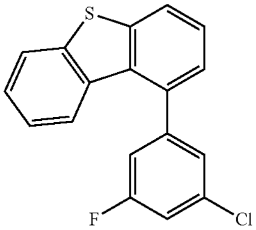
Sub 2-35
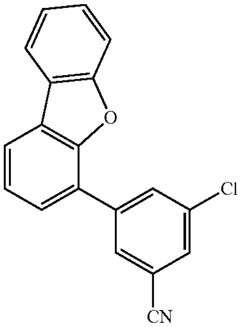
Sub 2-36
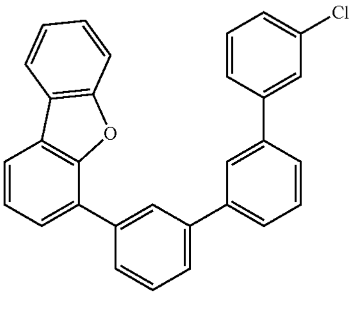

-continued
Sub 2-37
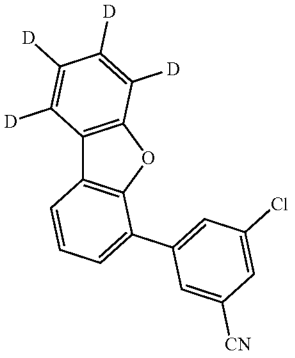
Sub 2-38
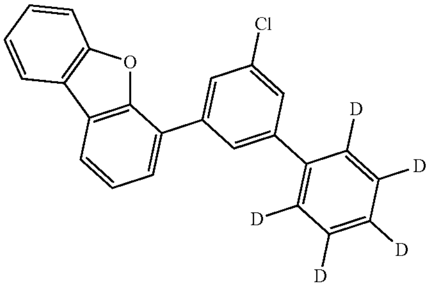
Sub 2-39
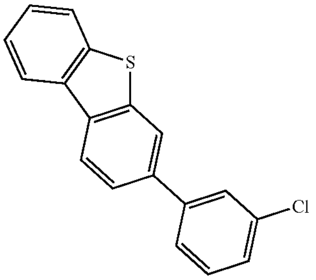
-continued
Sub 2-40
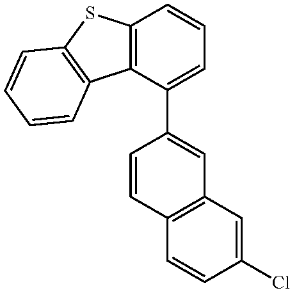
Sub 2-41
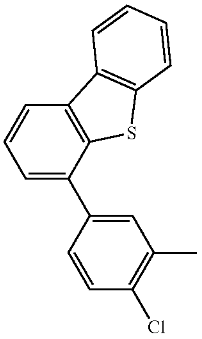
Sub 2-42
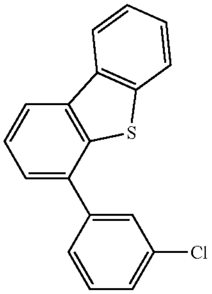
TABLE 2
| compound | FD-MS | compound | FD-MS |
|---|---|---|---|
| Sub 2-2 | m/z = 354.08 ($C_{24}H_{15}ClO$ = 354.83) | Sub 2-7 | m/z = 459.08 ($C_{30}H_{18}ClNS$ = 459.99) |
| Sub 2-8 | m/z = 518.15 ($C_{36}H_{23}ClN_2$ = 519.04) | Sub 2-16 | m/z = 303.05 ($C_{19}H_{10}ClNO$ = 303.75) |
| Sub 2-27 | m/z = 386.14 ($C_{26}H_{15}D_4ClO$ = 386.91) | Sub 2-29 | m/z = 444.09 ($C_{30}H_{17}ClO_2$ = 444.91) |
| Sub 2-33 | m/z = 443.11 ($C_{30}H_{18}ClNO$ = 443.93) | Sub 2-37 | m/z = 307.07 ($C_{19}H_6D_4ClNO$ = 307.77) |

III. Synthesis of Final Compound

1. Synthesis Example of P 1-2

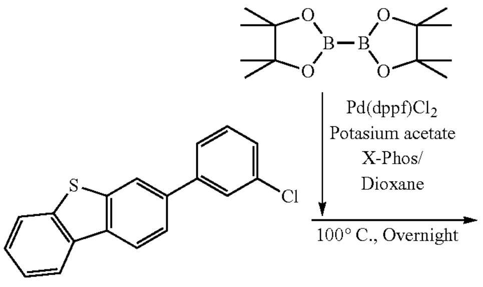

Sub 2-39

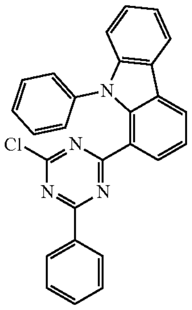

Core 2-1

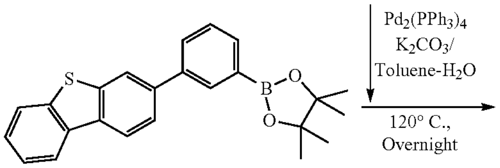

Sub 2-39-B

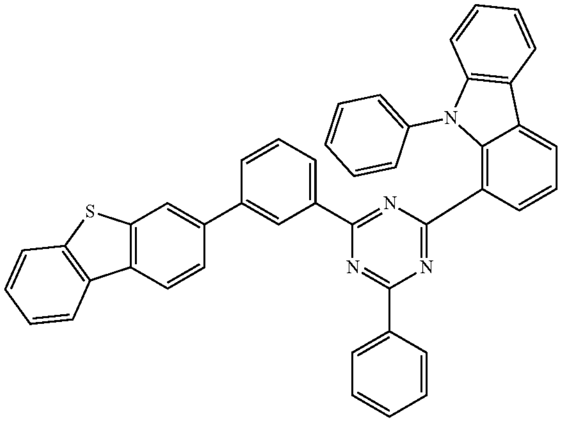

P 1-2

(1) Synthesis of Sub 2-39-B

Sub 2-39 (5.0 g, 17.0 mmol), bis(pinacolato)diboron (6.46 g, 25.4 mmol), $Pd_2(dba)_3$ (0.78 g, 0.8 mmol), potassium acetate (4.99 g, 50.9 mmol) and X-phos (0.81 g, 1.7 mmol) were placed in a round bottom flask and dioxane (100 mL) was added thereto. The mixture was stirred for 6 hours at 100° C. When the reaction was completed, the reaction product was quenched by adding water and then water in the reaction product was removed. Then, the reaction product was filtered under reduced pressure. An organic layer was dried over $MgSO_4$ and concentrated to obtain 5.50 g (yield: 84%) of the product.

(2) Synthesis of P 1-2

Sub 2-39-B (5.50 g, 14.2 mmol), Core 2-1 (3.20 g, 14.2 mmol), $Pd_2(PPh_3)_4$ (0.49 g, 0.4 mmol) and $K_2CO_3$ (5.90 g, 42.7 mmol) were placed in a round bottom flask and THF (100 mL) and $H_2O$ (50 mL) were added thereto. After raising the temperature of the mixture to 120□, the mixture was stirred for 24 hours. When the reaction was completed, water in the reaction product was removed and the reaction product was filtered under reduced pressure. After that, the filtrate was dried over $MgSO_4$ and concentrated. Thereafter, impurities were removed from the concentrate by applying a silica gel column and recrystallization to obtain 7.20 g (yield: 77%) of the product.

2. Synthesis Example of P 2-8

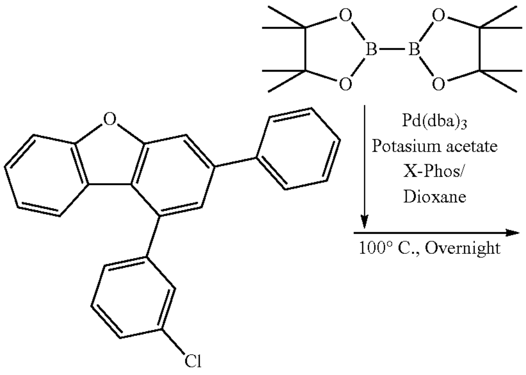

Sub 2-19

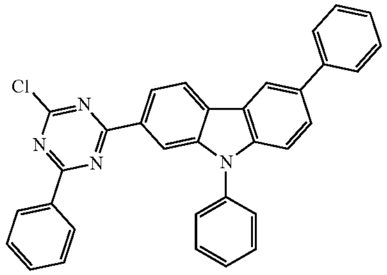

Core 2-4

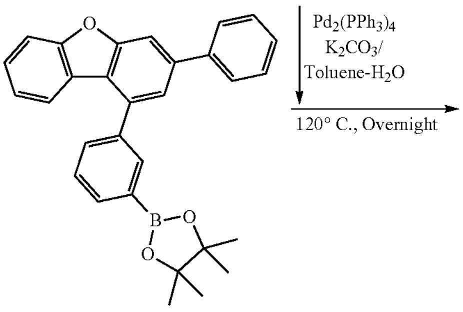

Sub 2-19-B

-continued

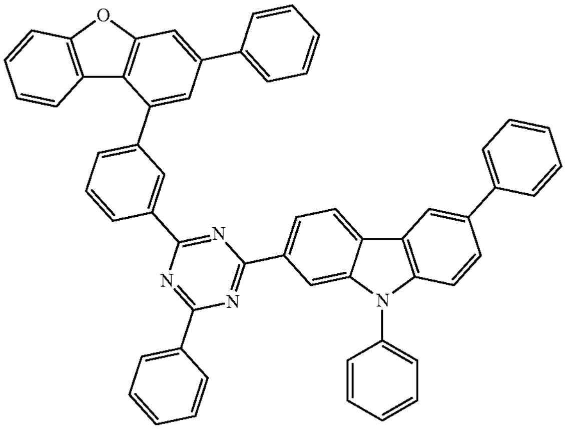

P 2-8

(1) Synthesis of Sub 2-19-B

The synthesis was performed by using Sub 2-19 (5.0 g, 14.1 mmol), bis(pinacolato)diboron (5.37 g, 21.1 mmol), $Pd_2(dba)_3$ (0.65 g, 0.7 mmol), potassium acetate (4.15 g, 42.3 mmol), X-phos (0.67 g, 1.4 mmol) and dioxane (100 mL) in the same manner as in the synthesis method of Sub 2-39-B to obtain 5.53 g (yield: 88%) of the product.

(2) Synthesis of P 2-8

The synthesis was performed by using Sub 2-19-B (5.50 g, 14.2 mmol), Core 2-4 (3.20 g, 14.2 mmol), $Pd_2(PPh_3)_4$ (0.49 g, 0.4 mmol), $K_2CO_3$ (5.90 g, 42.7 mmol), THF (100 mL) and $H_2O$ (50 mL) in the same manner as in the synthesis method of P 1-2 to obtain 6.88 g (yield: 70%) of the product.

5. Synthesis Example of P 3-23

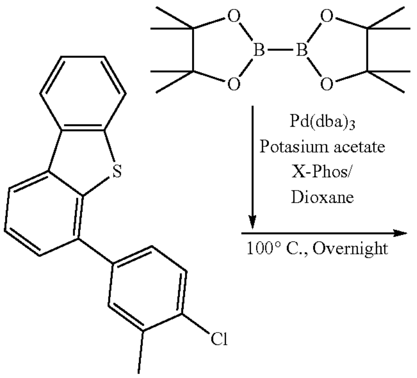

Sub 2-41

-continued

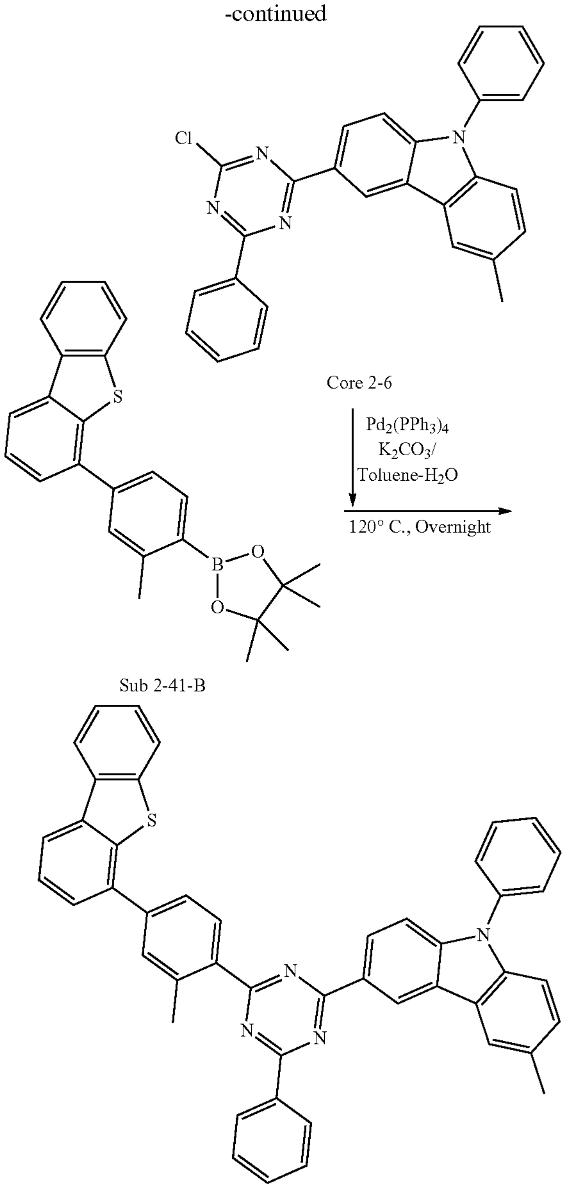

Core 2-6

Sub 2-41-B

P 3-23

(1) Synthesis of Sub 2-41-B

The synthesis was performed by using Sub 2-41 (5.0 g, 16.2 mmol), bis(pinacolato)diboron (6.17 g, 24.3 mmol), $Pd_2(dba)_3$ (0.73 g, 0.8 mmol), potassium acetate (4.77 g, 48.6 mmol), X-phos (0.77 g, 1.6 mmol) and dioxane (100 mL) in the same manner as in the synthesis method of Sub 2-39-B to obtain 5.90 g (yield: 91%) of the product.

(2) Synthesis of P 3-23

The synthesis was performed by using Sub 2-41-B (5.90 g, 14.7 mmol), Core 2-6 (6.59 g, 14.7 mmol), $Pd_2(PPh_3)_4$ (0.51 g, 0.4 mmol), $K_2CO_3$ (6.11 g, 44.2 mmol), THF (100 mL) and $H_2O$ (50 mL) in the same manner as in the synthesis method of P 1-2 to obtain 8.07 g (yield: 80%) of the product.

6. Synthesis Example of P 4-30

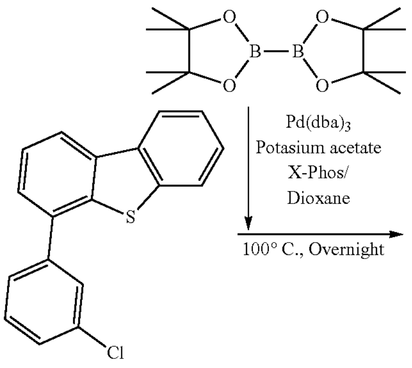

Sub 2-42

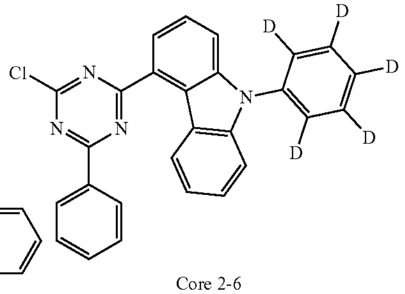

Core 2-6

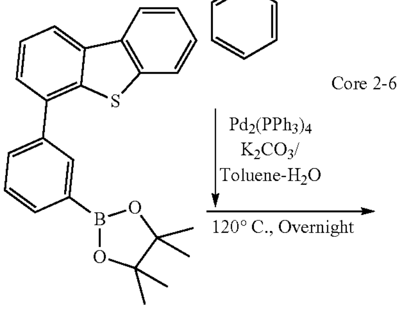

Sub 2-42

-continued

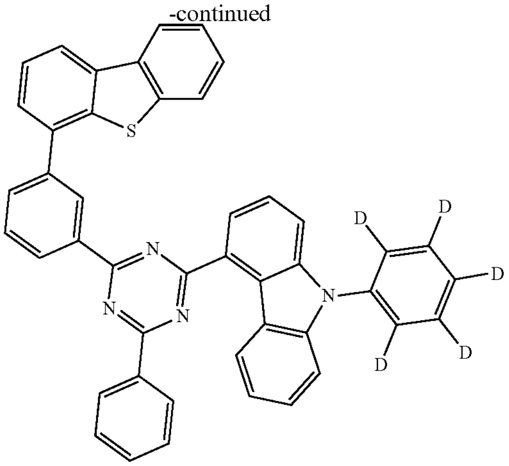

P 4-30

(1) Synthesis of Sub 2-42-B

The synthesis was performed by using Sub 2-42 (5.0 g, 17.0 mmol), bis(pinacolato)diboron (6.46 g, 25.4 mmol), $Pd_2(dba)_3$ (0.78 g, 0.8 mmol), potassium acetate (4.99 g, 50.9 mmol), X-phos (0.81 g, 1.7 mmol) and dioxane (100 mL) in the same manner as in the synthesis method of Sub 2-39-B to obtain 6.03 g (yield: 92%) of the product.

(2) Synthesis of P 4-30

The synthesis was performed by using Sub 2-42-B (6.03 g, 15.6 mmol), Core 2-8 (6.84 g, 15.6 mmol), $Pd_2(PPh_3)_4$ (0.54 g, 0.5 mmol), $K_2CO_3$ (6.47 g, 46.8 mmol), THF (100 mL) and $H_2O$ (50 mL) in the same manner as in the synthesis method of P 1-2 to obtain 8.37 g (yield: 81%) of the product.

The FD-MS values of compounds P 1-1 to P 4-30 of the present invention prepared according to the above synthesis examples are shown in Table 3 below.

TABLE 3

| compound | FD-MS | compound | FD-MS |
|---|---|---|---|
| P 1-1 | m/z = 640.23 ($C_{45}H_{28}N_4O$ = 640.75) | P 1-2 | m/z = 656.20 ($C_{45}H_{28}N_4S$ = 656.81) |
| P 1-3 | m/z = 715.27 ($C_{51}H_{33}N_5$ = 715.86) | P 1-4 | m/z = 716.26 ($C_{51}H_{32}N_5O$ = 716.84) |
| P 1-5 | m/z = 732.23 ($C_{51}H_{32}N_4S$ = 732.91) | P 1-6 | m/z = 791.30 ($C_{57}H_{37}N_5$ = 791.96) |
| P 1-7 | m/z = 716.26 ($C_{51}H_{32}N_4O$ = 716.84) | P 1-8 | m/z = 706.22 ($C_{49}H_{30}N_4S$ = 706.87) |
| P 1-9 | m/z = 765.29 ($C_{55}H_{35}N_5$ = 765.92) | P 1-10 | m/z = 730.24 ($C_{51}H_{30}N_4O_2$ = 730.83) |
| P 1-11 | m/z = 746.21 ($C_{51}H_{30}N_4OS$ = 746.89) | P 1-12 | m/z = 821.26 ($C_{57}H_{35}N_5S$ = 822.00) |
| P 1-13 | m/z = 880.33 ($C_{63}H_{40}N_6$ = 881.06) | P 1-14 | m/z = 756.29 ($C_{54}H_{36}N_4O$ = 756.91) |
| P 1-15 | m/z = 772.27 ($C_{54}H_{36}N_4S$ = 772.97) | P 1-16 | m/z = 640.23 ($C_{45}H_{28}N_4O$ = 640.75) |
| P 1-17 | m/z = 832.27 ($C_{59}H_{36}N_4S$ = 833.03) | P 1-18 | m/z = 766.27 ($C_{55}H_{34}N_4O$ = 766.90) |
| P 1-19 | m/z = 730.27 ($C_{52}H_{34}N_4O$ = 730.87) | P 1-20 | m/z = 808.27($C_{57}H_{36}N_4S$ = 809.00) |
| P 1-21 | m/z = 866.25 ($C_{59}H_{38}N_4S_2$ = 867.10) | P 1-22 | m/z = 797.32 ($C_{57}H_{31}D_5N_4O$ = 797.97) |
| P 1-23 | m/z = 766.27 ($C_{55}H_{34}N_4O$ = 766.90) | P 1-24 | m/z = 729.29 ($C_{52}H_{35}N_5$ = 729.89) |
| P 1-25 | m/z = 880.32 ($C_{64}H_{40}N_4O$ = 881.05) | P 1-26 | m/z = 796.23 ($C_{55}H_{32}N_4OS$ = 796.95) |
| P 1-27 | m/z = 665.22 ($C_{46}H_{27}N_5O$ = 665.76) | P 1-28 | m/z = 670.22 ($C_{46}H_{30}N_4S$ = 670.83) |
| P 1-29 | m/z = 791.30 ($C_{57}H_{37}N_5$ = 791.96) | P 1-30 | m/z = 822.25 ($C_{57}H_{34}N_4OS$ = 822.99) |
| P 2-1 | m/z = 656.20 ($C_{45}H_{28}N_4S$ = 656.81) | P 2-2 | m/z = 808.27 ($C_{57}H_{36}N_4S$ = 809.00) |
| P 2-3 | m/z = 816.29 ($C_{59}H_{36}N_4O$ = 816.96) | P 2-4 | m/z = 782.25 ($C_{55}H_{34}N_4S$ = 782.97) |
| P 2-5 | m/z = 766.27 ($C_{55}H_{34}N_4O$ = 766.90) | P 2-6 | m/z = 706.22 ($C_{49}H_{30}N_4S$ = 706.87) |
| P 2-7 | m/z = 861.32 ($C_{51}H_{31}N_4D_5O_2$ = 862.02) | P 2-8 | m/z = 792.29 ($C_{57}H_{36}N_4O$ = 792.94) |
| P 2-9 | m/z = 805.28 ($C_{57}H_{35}N_5O$ = 805.94) | P 2-10 | m/z = 690.24 ($C_{49}H_{30}N_4O$ = 690.81) |
| P 2-11 | m/z716.26 ($C_{51}H_{32}N_4O$ = 716.84) | P 2-12 | m/z = 732.23 ($C_{51}H_{32}N_4S$ = 732.91) |
| P 2-13 | m/z = 715.27 ($C_{51}H_{33}N_5$ = 715.86) | P 2-14 | m/z = 706.22 ($C_{49}H_{30}N_4S$ = 706.87) |
| P 2-15 | m/z = 740.26 ($C_{53}H_{32}N_4O$ = 740.87) | P 2-16 | m/z = 806.30 ($C_{58}H_{38}N_4O$ = 806.97) |
| P 2-17 | m/z = 805.28 ($C_{57}H_{35}N_5O$ = 805.94) | P 2-18 | m/z = 772.27 ($C_{54}H_{36}N_4S$ = 772.97) |
| P 2-19 | m/z = 865.32 ($C_{63}H_{39}N_5$ = 866.04) | P 2-20 | m/z = 855.30 ($C_{61}H_{37}N_5O$ = 856.00) |
| P 2-21 | m/z = 716.26 ($C_{51}H_{32}N_4O$ = 716.84) | P 2-22 | m/z = 668.26 ($C_{47}H_{32}N_4O$ = 688.80) |
| P 2-23 | m/z = 746.25 ($C_{52}H_{34}N_4S$ = 746.93) | P 2-24 | m/z = 805.28 ($C_{57}H_{35}N_5O$ = 805.94) |

TABLE 3-continued

| compound | FD-MS | compound | FD-MS |
|---|---|---|---|
| P 2-25 | m/z = 748.31 ($C_{53}H_{32}N_4D_4O$ = 748.92) | P 2-26 | m/z = 746.25 ($C_{52}H_{34}N_4S$ = 746.93) |
| P 2-27 | m/z = 684.23 ($C_{47}H_{32}N_4S$ = 684.86) | P 2-28 | m/z = 740.26 ($C_{53}H_{32}N_4O$ = 740.87) |
| P 2-29 | m/z = 806.27 ($C_{57}H_{34}N_4O_2$ = 806.93) | P 2-30 | m/z = 841.32 ($C_{61}H_{39}N_5$ = 842.02) |
| P 3-1 | m/z = 656.20 ($C_{45}H_{28}N_4S$ = 656.81) | P 3-2 | m/z = 716.26 ($C_{51}H_{32}N_4O$ = 716.84) |
| P 3-3 | m/z = 808.27 ($C_{57}H_{36}N_4S$ = 809.00) | P 3-4 | m/z = 716.26 ($C_{51}H_{32}N_4O$ = 716.84) |
| P 3-5 | m/z = 640.23 ($C_{45}H_{28}N_4O$ = 640.75) | P 3-6 | m/z = 732.23 ($C_{51}H_{32}N_4S$ = 732.91) |
| P 3-7 | m/z = 732.23 ($C_{51}H_{32}N_4S$ = 732.91) | P 3-8 | m/z = 690.24 ($C_{49}H_{30}N_4O$ = 690.81) |
| P 3-9 | m/z = 706.22 ($C_{49}H_{30}N_4S$ = 706.87) | P 3-10 | m/z = 756.23 ($C_{53}H_{32}N_4S$ = 756.93) |
| P 3-11 | m/z = 746.21 ($C_{51}H_{30}N_4OS$ = 746.89) | P 3-12 | m/z = 670.22 ($C_{46}H_{30}N_4S$ = 670.83) |
| P 3-13 | m/z = 741.25 ($C_{52}H_{31}N_5O$ = 741.85) | P 3-14 | m/z = 791.30 ($C_{57}H_{37}N_5$ = 791.96) |
| P 3-15 | m/z = 838.22 ($C_{57}H_{34}N_4S_2$ = 839.05) | P 3-16 | m/z = 716.26 ($C_{51}H_{32}N_4O$ = 716.84) |
| P 3-17 | m/z = 746.21 ($C_{51}H_{30}N_4OS$ = 746.89) | P 3-18 | m/z = 730.24 ($C_{51}H_{30}N_4O_2$ = 730.83) |
| P 3-19 | m/z = 756.29 ($C_{54}H_{36}N_4O$ = 756.91) | P 3-20 | m/z = 791.30 ($C_{57}H_{37}N_5$ = 791.96) |
| P 3-21 | m/z = 772.27 ($C_{54}H_{36}N_4S$ = 772.97) | P 3-22 | m/z = 756.29 ($C_{54}H_{36}N_4O$ = 756.91) |
| P 3-23 | m/z = 684.23 ($C_{47}H_{32}N_4S$ = 684.86) | P 3-24 | m/z = 706.22 ($C_{49}H_{30}N_4S$ = 706.87) |
| P 3-25 | m/z = 841.32 ($C_{61}H_{39}N_5$ = 842.02) | P 3-26 | m/z = 746.25 ($C_{52}H_{34}N_4S$ = 746.93) |
| P 3-27 | m/z = 791.30 ($C_{57}H_{37}N_5$ = 791.96) | P 3-28 | m/z = 762.19 ($C_{51}H_{30}N_4S_2$ = 762.95) |
| P 3-29 | m/z = 715.27 ($C_{51}H_{33}N_5$ = 715.86) | P 3-30 | m/z = 732.23 ($C_{51}H_{32}N_4S$ = 732.91) |
| P 4-1 | m/z = 656.20 ($C_{45}H_{28}N_4S$ = 656.81) | P 4-2 | m/z = 842.30 ($C_{61}H_{38}N_4O$ = 843.00) |
| P 4-3 | m/z = 732.23 ($C_{51}H_{32}N_4S$ = 732.91) | P 4-4 | m/z = 715.27 ($C_{51}H_{33}N_5$ = 715.86) |
| P 4-5 | m/z = 716.26 ($C_{51}H_{32}N_4O$ = 716.84) | P 4-6 | m/z = 808.27 ($C_{57}H_{36}N_4S$ = 809.00) |
| P 4-7 | m/z = 640.23 ($C_{45}H_{28}N_4O$ = 640.75) | P 4-8 | m/z = 716.26 ($C_{51}H_{32}N_4O$ = 716.84) |
| P 4-9 | m/z = 690.24 ($C_{49}H_{30}N_4O$ = 690.81) | P 4-10 | m/z = 670.22 ($C_{46}H_{30}N_4S$ = 670.83) |
| P 4-11 | m/z = 805.28 ($C_{57}H_{35}N_5O$ = 805.94) | P 4-12 | m/z = 690.24 ($C_{49}H_{30}N_4O$ = 690.81) |
| P 4-13 | m/z = 765.29 ($C_{55}H_{35}N_5$ = 765.92) | P 4-14 | m/z = 674.19 ($C_{45}H_{27}FN_4S$ = 674.80) |
| P 4-15 | m/z = 665.22 ($C_{46}H_{27}N_5O$ = 665.76) | P 4-16 | m/z = 681.20 ($C_{46}H_{27}N_5S$ = 681.82) |
| P 4-17 | m/z = 681.20 ($C_{46}H_{27}N_5S$ = 681.82) | P 4-18 | m/z = 746.21 ($C_{51}H_{30}N_4OS$ = 746.89) |
| P 4-19 | m/z = 822.28 ($C_{58}H_{38}N_4S$ = 823.03) | P 4-20 | m/z = 766.27 ($C_{55}H_{34}N_4O$ = 766.90) |
| P 4-21 | m/z = 706.22 ($C_{49}H_{30}N_4S$ = 706.87) | P 4-22 | m/z = 755.23 ($C_{52}H_{29}N_5O_2$ = 755.84) |
| P 4-23 | m/z = 757.23 ($C_{52}H_{31}N_5S$ = 757.92) | P 4-24 | m/z = 842.30 ($C_{61}H_{38}N_4O$ = 843.00) |
| P 4-25 | m/z = 805.28 ($C_{57}H_{35}N_5O$ = 805.94) | P 4-26 | m/z = 729.29 ($C_{52}H_{35}N_5$ = 729.89) |
| P 4-27 | m/z = 669.25 ($C_{46}H_{23}D_4N_5O$ = 669.78) | P 4-28 | m/z = 808.27 ($C_{57}H_{36}N_4S$ = 809.00) |
| P 4-29 | m/z = 721.29 ($C_{51}H_{27}D_5N_4O$ = 721.87) | P 4-30 | m/z = 661.23 ($C_{45}H_{23}D_5N_4S$ = 661.84) |

Fabrication and Evaluation of Organic Electric Element

[Example 1] Green PLED (Host)

$N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on an ITO layer (anode) formed on a glass substrate to form a hole injection layer with a thickness of 60 nm. Thereafter, 4,4-bis[N-(1-naphthalenyl)-N-phenylamino]biphenyl (hereinafter, "NPB") on the hole injection layer was vacuum-deposited to a thickness of 60 nm to form a hole transport layer.

Next, on the hole transport layer, the compound P 1-1 of the present invention as a host material and [tris(2-phenylpyridine)-iridium] (hereinafter, "$(Ir(PPy)_3)$") as a dopant material in a weight ratio of 95:5 were deposited on the hole transport layer to form a light emitting layer with a thickness of 30 nm.

Next, (1,1'-biphenyl-4-olato)bis(2-methyl-8-quinolinolato)aluminum (hereinafter, "BAlq") was vacuum-deposited to a thickness of 10 nm on the light emitting layer to form a hole blocking layer, and tris(8-quinolinolato)aluminum (hereinafter, "$Alq_3$") was vacuum-deposited to a thickness of 40 nm on the hole blocking layer to form a an electron transport layer.

Thereafter, LiF was deposited to a thickness of 0.2 nm to form an electron injection layer on the electron transport layer, and then Al was deposited to a thickness of 150 nm to form a cathode on the electron injection layer.

[Example 2] to [Example 25]

The organic electroluminescent elements were manufactured in the same manner as described in Example 1 except that compounds of the present invention described in the following Table 4 instead of compound P 1-1 of the present invention were used as host material of the light emitting layer.

[Comparative Example 1] to [Comparative Example 3]

The organic electroluminescent elements were manufactured in the same manner as described in Example 1 except that one of the following Comparative Compound A to D instead of compound P 1-1 of the present invention was used as host material of the light emitting layer.

<Comp. Compd A>

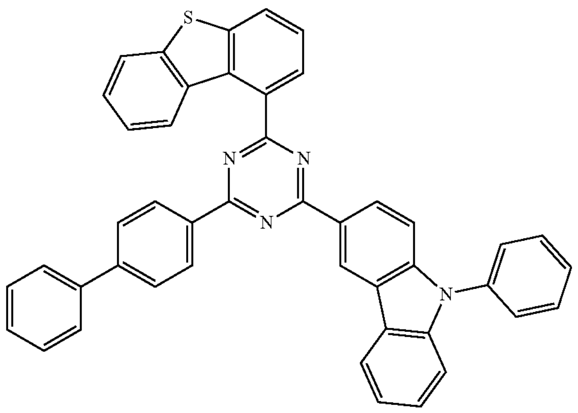

-continued

<Comp.Compd B>

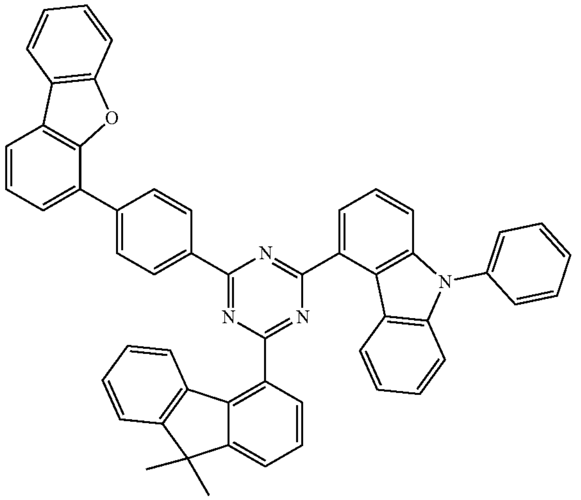

<Comp.Compd C>

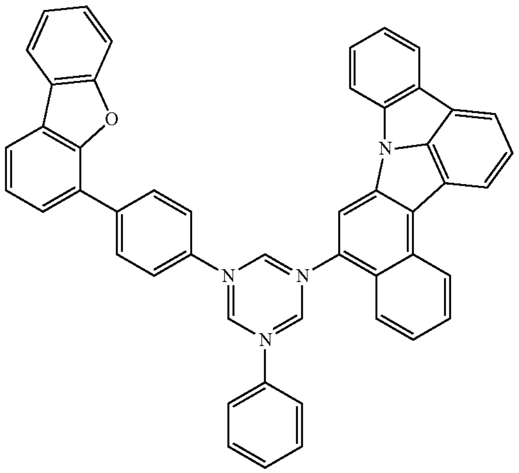

-continued

<Comp.CompdD>

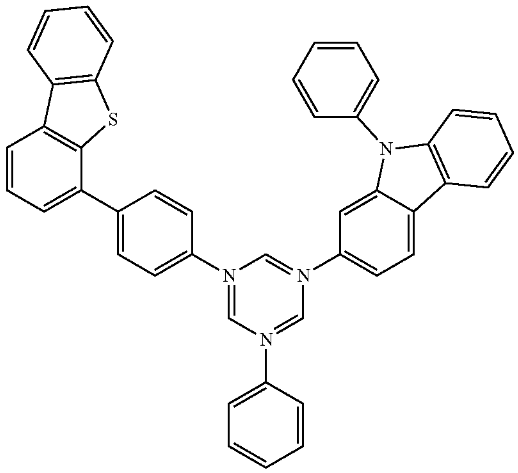

Electroluminescence (EL) characteristics were measured with PR-650 (Photo research) by applying a forward bias DC voltage to the organic electroluminescent elements prepared in Examples 1 to 25 of the present invention and Comparative Examples 1 to 4. The T95 life time was measured using a life time measuring apparatus manufactured by me science Inc. at reference brightness of 5000 cd/$m^2$. The measurement results are shown in Table 4.

TABLE 4

| | compound | Voltage (V) | Current Density ($mA/cm^2$) | Brightness ($cd/m^2$) | Efficiency (cd/A) | Lifetime T(95) | CIE x | CIE y |
|---|---|---|---|---|---|---|---|---|
| comp.Ex(1) | comp.Com A | 5.5 | 21.7 | 5000.0 | 23.0 | 60.8 | 0.34 | 0.62 |
| comp.Ex(2) | comp.Com B | 5.3 | 18.2 | 5000.0 | 27.4 | 67.1 | 0.33 | 0.64 |
| comp.Ex(3) | comp.Com C | 5.7 | 19.9 | 5000.0 | 25.1 | 65.7 | 0.31 | 0.65 |
| comp.Ex(4) | comp.Com D | 5.8 | 20.6 | 5000.0 | 24.3 | 63.2 | 0.30 | 0.62 |
| Ex.(1) | P 1-1 | 5.0 | 15.1 | 5000.0 | 33.0 | 92.2 | 0.30 | 0.62 |
| Ex.(2) | P 1-6 | 4.9 | 14.9 | 5000.0 | 33.6 | 93.2 | 0.33 | 0.65 |
| Ex.(3) | P 1-11 | 4.8 | 15.1 | 5000.0 | 33.2 | 91.5 | 0.33 | 0.64 |
| Ex.(4) | P 1-16 | 4.9 | 14.4 | 5000.0 | 34.7 | 93.2 | 0.33 | 0.62 |
| Ex.(5) | P 1-19 | 4.8 | 14.5 | 5000.0 | 34.4 | 90.1 | 0.31 | 0.64 |
| Ex.(6) | P 1-22 | 4.7 | 13.9 | 5000.0 | 36.1 | 90.8 | 0.31 | 0.64 |
| Ex.(7) | P 1-25 | 4.8 | 14.5 | 5000.0 | 34.5 | 91.6 | 0.34 | 0.64 |
| Ex.(8) | P 1-30 | 4.7 | 13.7 | 5000.0 | 36.4 | 92.3 | 0.34 | 0.60 |
| Ex.(9) | P 2-2 | 4.5 | 11.7 | 5000.0 | 42.9 | 97.6 | 0.33 | 0.60 |
| Ex.(10) | P 2-8 | 4.5 | 11.9 | 5000.0 | 42.1 | 99.1 | 0.35 | 0.62 |
| Ex.(11) | P 2-11 | 4.4 | 12.5 | 5000.0 | 40.1 | 99.6 | 0.34 | 0.64 |
| Ex.(12) | P 2-15 | 4.5 | 12.5 | 5000.0 | 40.0 | 103.4 | 0.31 | 0.61 |
| Ex.(13) | P 2-18 | 4.7 | 13.9 | 5000.0 | 36.1 | 97.9 | 0.34 | 0.63 |
| Ex.(14) | P 2-24 | 4.5 | 12.5 | 5000.0 | 39.9 | 96.5 | 0.32 | 0.61 |
| Ex.(15) | P 2-25 | 4.7 | 12.5 | 5000.0 | 39.8 | 96.4 | 0.32 | 0.62 |
| Ex.(16) | P 2-29 | 4.5 | 12.7 | 5000.0 | 39.3 | 96.9 | 0.33 | 0.63 |
| Ex.(17) | P 3-1 | 4.7 | 13.4 | 5000.0 | 37.4 | 98.6 | 0.33 | 0.62 |
| Ex.(18) | P 3-7 | 4.7 | 13.2 | 5000.0 | 37.8 | 98.7 | 0.32 | 0.62 |

TABLE 4-continued

| | compound | Voltage (V) | Current Density (mA/cm²) | Brightness (cd/m²) | Efficiency (cd/A) | Lifetime T(95) | CIE x | CIE y |
|---|---|---|---|---|---|---|---|---|
| Ex.(19) | P 3-16 | 4.5 | 12.2 | 5000.0 | 41.1 | 97.1 | 0.31 | 0.63 |
| Ex.(20) | P 3-17 | 4.6 | 12.9 | 5000.0 | 38.6 | 98.9 | 0.30 | 0.64 |
| Ex.(21) | P 4-4 | 5.0 | 14.6 | 5000.0 | 34.2 | 94.2 | 0.34 | 0.61 |
| Ex.(22) | P 4-6 | 4.9 | 14.5 | 5000.0 | 34.4 | 92.4 | 0.31 | 0.62 |
| Ex.(23) | P 4-15 | 4.9 | 14.7 | 5000.0 | 33.9 | 93.1 | 0.33 | 0.62 |
| Ex.(24) | P 4-24 | 4.8 | 14.4 | 5000.0 | 34.7 | 91.6 | 0.35 | 0.62 |
| Ex.(25) | P 4-28 | 4.7 | 13.8 | 5000.0 | 36.3 | 91.0 | 0.32 | 0.62 |

From the results of Table 4, it is can be seen that the driving, efficiency and lifespan are significantly improved where the material for an organic electric element of the present invention was used as a phosphorescent host for an organic electric element.

Comparative Compound A to Comparative Compound D are similar to compound of the present invention in that triazine is the core and dibenzothiophene (or dibenzofuran) is substituted, but each has structural differences. Comparative compound A differs in that there is no linking group between the triazine core and dibenzothiophene (or dibenzofuran), whereas the compound of the present invention always has a linking group L.

In addition, Comparative Compound B differs in that the moiety corresponding to $Ar^1$ in Formula 1 of the present invention is 9,9-dimethylfluorene, whereas $Ar^1$ of the present invention is necessarily a $C_6$-$C_{12}$ aryl group. In addition, Comparative Compound C and Comparative Compound D are different from the compounds of the present invention in that $R^3$ and $R^4$ in Formula 1 of the present invention form a ring with an adjacent group, respectively.

Table 5 shows the physical properties of Compound P 3-1 of the present invention and Comparative Compounds A to D.

It can be seen that Comparative Compound C and Comparative Compound D also differ in physical properties such as HOMO, LUMO, $T_1$ and band gab from Compound P 3-1 of the present invention, wherein Comparative Compound C and Comparative Compound D correspond to the case where a carbazole moiety is fused by combining $R^3$ or $R^4$ with an adjacent group to form a ring.

The difference in physical properties caused by this structural difference acts as a major factor in improving the performance of the device when depositing materials during device manufacturing. Therefore, it causes that where compound of the present invention is used as host, the driving voltage of element is lowered by 0.3-1.4 eV, the efficiency is improved by 44-87%, and the lifespan is improved by 48-70% compared to the case of using one of the Comparative Compound A to D.

This suggests that the physical properties of the compound vary depending on the presence or absence of a linking group, the type of substituent, and the presence or absence of fused carbazole, and the difference in physical properties may result in significant changes in the driving voltage, efficiency and lifespan of the device. Accordingly, it can be seen that according to the present invention, a remarkable effect that cannot be expected in the conventional compound occurs by varying a linking group, a substituent, fusion and so on.

TABLE 5

| | The present invention P 3-1 | comp. Com A | comp. Com B | comp. Com C | comp. Com D |
|---|---|---|---|---|---|
| G. HOMO (eV) | −5.44 | −5.36 | −5.34 | −5.63 | −5.32 |
| G. LUMO (eV) | −1.68 | −1.78 | −1.82 | −1.99 | −1.90 |
| G.T1 | 2.82 | 2.69 | 2.63 | 2.67 | 2.27 |
| G. Band gab | 3.75 | 3.58 | 3.51 | 3.64 | 3.41 |

Comparing the physical property values of Comparative Compound A and Compound P 3-1 of the present invention in Table 5, it can be seen that Compound P 3-1 of the present invention has a deeper HOMO and a higher LUMO than Comparative Compound A, and thus Compound P 3-1 has wide band gab and its $T_1$ is also elevated. In other words, it can be seen that the presence of the connector L causes a difference in physical properties.

In addition, Comparing the physical property values of Comparative Compound B and Compound P 3-1 of the present invention, it can be seen that compound of the present invention which is substituted with a general $C_6$-$C_{12}$ aryl group has a deeper HOMO and a higher LUMO than Comparative Compound to which a specific substituent such as fluorene is bonded, and thus compound of the present invention has wide band gab and its $T_1$ is also elevated.

Although the exemplary embodiments of the present invention have been described for illustrative purposes, those skilled in the art to which the present invention pertains will be capable of various modifications without departing from the essential characteristics of the present invention. Therefore, the embodiment disclosed herein is intended to illustrate the scope of the technical idea of the present invention, and the spirit and scope of the present invention are not limited by the embodiments. The scope of the present invention shall be construed on the basis of the accompanying claims, and it shall be construed that all of the technical ideas included within the scope equivalent to the claims belong to the present invention.

The invention claimed is:

1. A compound of Formula 1:

<Formula 1>

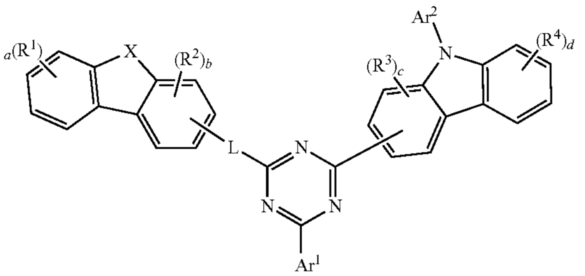

wherein:

X is O or S, $R^1$ to $R^4$ are each independently selected from the group consisting of hydrogen, deuterium, halogen, a cyano group, a $C_6$-$C_{60}$ aryl group, a fluorenyl group, a $C_2$-$C_{60}$ heterocyclic group containing at least one heteroatom of O, N, S, Si, and P, a $C_1$-$C_{50}$ alkyl group, with the proviso that: at least one of $R^1$ and $R^2$ is in plural and adjacent $R^1$ groups and/or adjacent $R^2$ groups form a $C_6$-$C_{14}$ aromatic hydrocarbon ring together, a and d are each an integer of 0 to 4, b and c are each an integer of 0 to 3, a+b+c+d is an integer of 1 or more, and where they are each an integer of 2 or more, each of a plurality of $R^1$s, each of a plurality of $R^2$s, each of a plurality of $R^3$s, each of a plurality of $R^4$s is the same or different from each other, $Ar^1$ is a $C_6$-$C_{12}$ aryl group, $Ar^2$ is selected from the group consisting of a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group and a $C_1$-$C_{50}$ alkyl group, L is selected from Formula a1 to Formula a12, Formulas a25 to a35, and Formula a37:

<Formula a1>

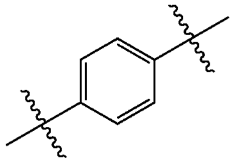

<Formula a2>

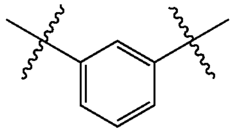

<Formula a3>

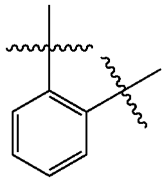

-continued

<Formula a4>

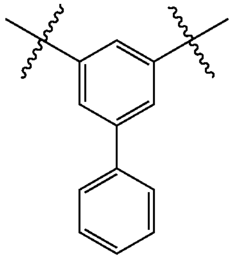

<Formula a5>

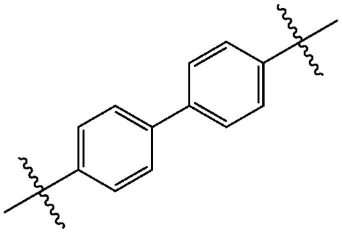

<Formula a6>

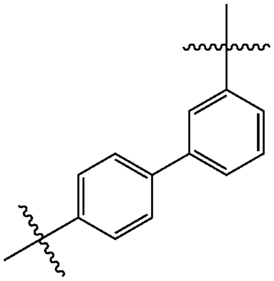

<Formula a7>

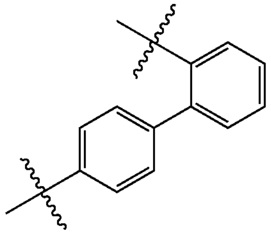

<Formula a8>

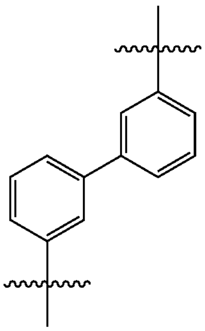

-continued
<Formula a9>
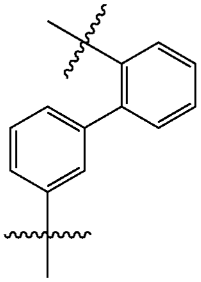
<Formula a10>
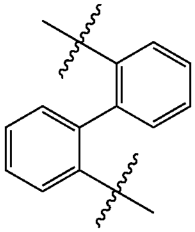
<Formula a11>
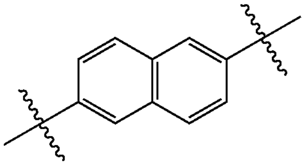
<Formula a12>
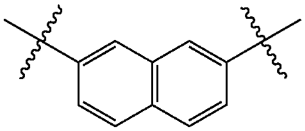
<Formula a25>
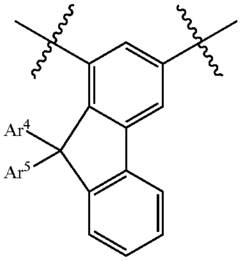
<Formula a26>
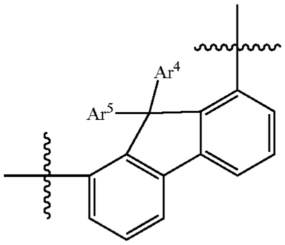
<Formula a27>
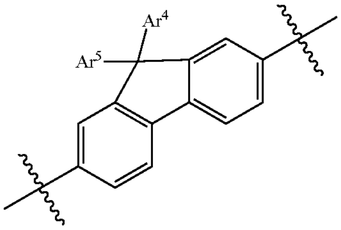
-continued
<Formula a28>
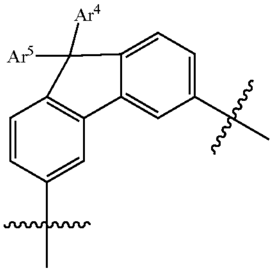
<Formula a29>
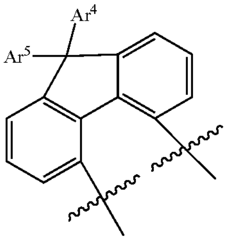
<Formula a30>
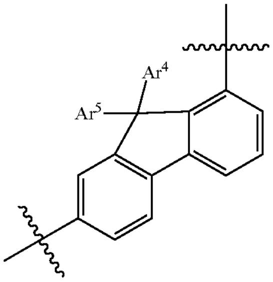
<Formula a31>
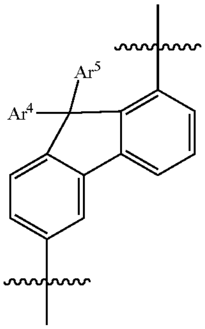
<Formula a32>
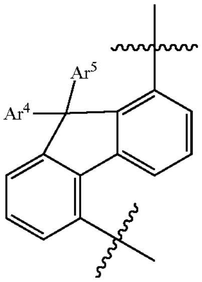

-continued

<Formula a33>

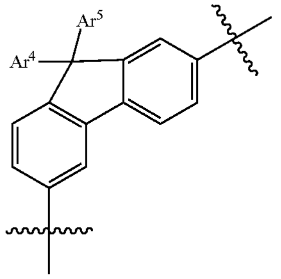

<Formula a34>

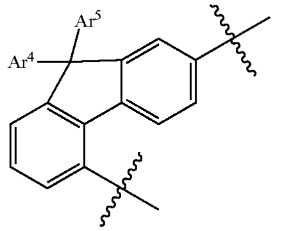

<Formula a35>

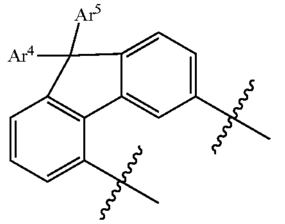

<Formula a37>

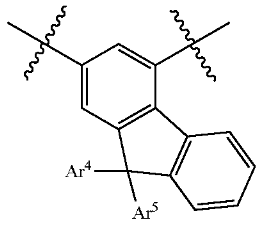

, wherein $Ar^4$ and $Ar^5$ are selected from the group consisting of hydrogen, a $C_6$-$C_{60}$ aryl group, a fluorenyl group, a $C_2$-$C_{60}$ heterocyclic group containing at least one heteroatom of O, N, S, Si, and P, a $C_3$-$C_{60}$ aliphatic ring group, a $C_1$-$C_{50}$ alkyl group and a combination thereof.

2. The compound of claim 1, wherein Formula 1 is represented by one of Formula 2 to Formula 5:

<Formula 2>

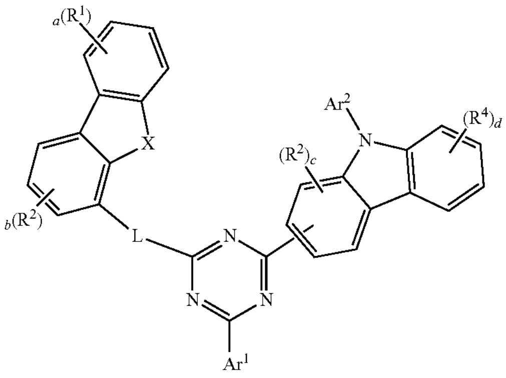

-continued

<Formula 3>

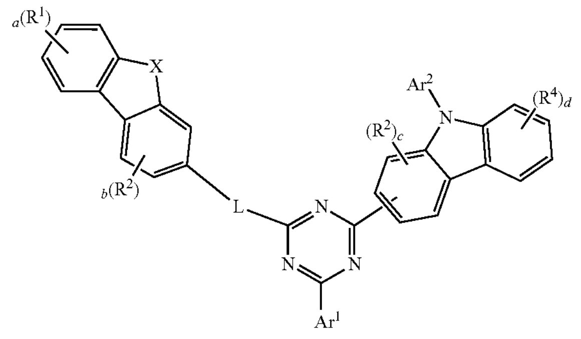

<Formula 4>

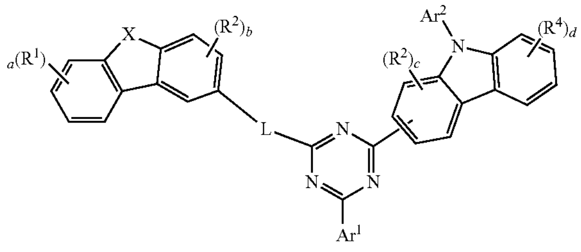

<Formula 5>

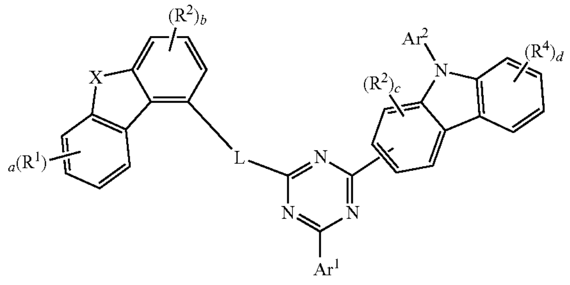

wherein X, $R^1$ to $R^4$, a to d, $Ar^1$, $Ar^2$ and L are the same as defined in claim 1.

3. The compound of claim 1, wherein Formula 1 is represented by one of Formula 6 to Formula 9:

<Formula 6>

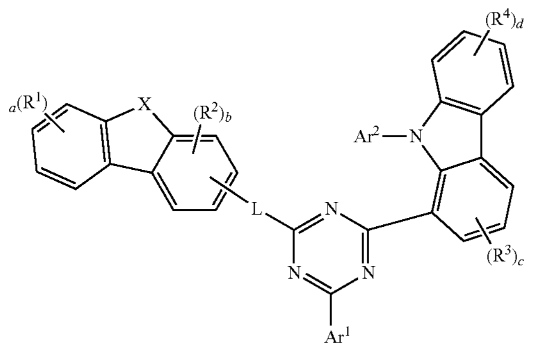

-continued

<Formula 7>

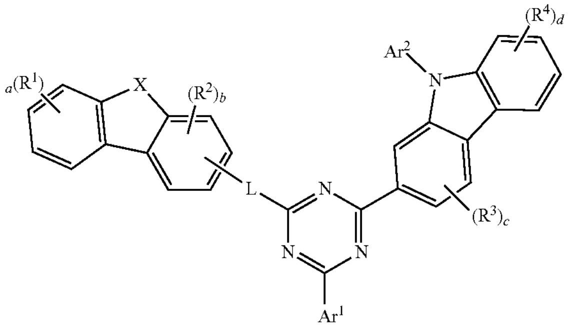

<Formula 8>

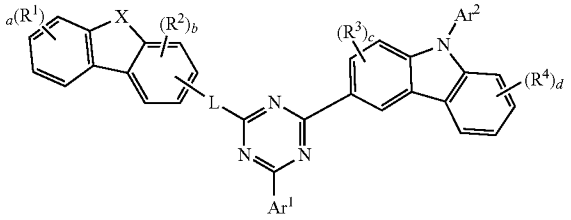

<Formula 9>

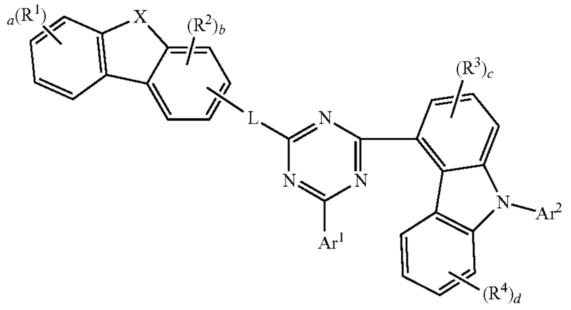

wherein X, $R^1$ to $R^4$, a to d, $Ar^1$, $Ar^2$ and L are the same as defined in claim 1.

4. An organic electric element comprising a first electrode, a second electrode, and an organic material layer formed between the first electrode and the second electrode, wherein the organic material layer comprises a single compound or two or more compounds represented by Formula 1 of claim 1.

5. The organic electric element of claim 4, wherein the organic material layer comprises at least one of a hole injection layer, a hole transport layer, an emission-auxiliary layer, a light emitting layer, an electron transport-auxiliary layer, an electron transport layer and an electron injection layer.

6. The organic electric element of claim 5, wherein the compound is comprised in the light emitting layer.

7. The organic electric element of claim 4, wherein the organic material layer is formed by spin coating, nozzle printing, inkjet printing, slot coating, dip coating or roll-to-roll.

8. An electronic device comprising a display device and a control unit for driving the display device, wherein the display device comprises the organic electric element of claim 4.

9. The electronic device of claim 8, wherein the organic electric element is selected from the group consisting of an organic electroluminescent element, an organic solar cell, an organic photo conductor, an organic transistor, an element for monochromatic illumination and element for quantum dot display.

* * * * *